US011643470B2

(12) United States Patent
You et al.

(10) Patent No.: US 11,643,470 B2
(45) Date of Patent: May 9, 2023

(54) PD-L1 AND OX40 BINDING PROTEINS FOR CANCER REGULATION

(71) Applicant: AP Biosciences, Inc., Taipei (TW)

(72) Inventors: Jhong-Jhe You, Taipei (TW); Ching-Hsuan Hsu, Taoyuan (TW); Po-Lin Huang, Taipei (TW); Hung-Tsai Kan, New Taipei (TW); Ting-Yi Chang, New Taipei (TW); Hsin-Ta Hsieh, Taipei (TW); Jeng-Horng Her, San Jose, CA (US)

(73) Assignee: AP Biosciences, Inc., Taipei (TW)

( * ) Notice: Subject to any disclaimer, the term of this patent is extended or adjusted under 35 U.S.C. 154(b) by 30 days.

(21) Appl. No.: 16/871,799

(22) Filed: May 11, 2020

(65) Prior Publication Data

US 2020/0270357 A1 Aug. 27, 2020

Related U.S. Application Data

(63) Continuation of application No. PCT/US2018/067868, filed on Dec. 28, 2018.

(60) Provisional application No. 62/611,543, filed on Dec. 29, 2017.

(51) Int. Cl.

*C07K 16/28* (2006.01)
*A61P 35/00* (2006.01)
*A61K 39/00* (2006.01)

(52) U.S. Cl.

CPC .......... *C07K 16/2878* (2013.01); *A61P 35/00* (2018.01); *C07K 16/2827* (2013.01); *A61K 2039/505* (2013.01); *C07K 2317/31* (2013.01); *C07K 2317/52* (2013.01); *C07K 2317/55* (2013.01); *C07K 2317/622* (2013.01)

(58) Field of Classification Search

None

See application file for complete search history.

(56) References Cited

U.S. PATENT DOCUMENTS 5,541,297 A 7/1996 Hansen et al.
7,550,140 B2 6/2009 Bakker et al.
7,943,743 B2 5/2011 Korman et al.
7,960,515 B2 6/2011 Min et al.
9,006,399 B2 4/2015 Liu et al.

(Continued)

FOREIGN PATENT DOCUMENTS

CN 104080809 A 10/2014
CN 104470949 A 3/2015

(Continued)

OTHER PUBLICATIONS

Reeck, "Homology in proteins and nucleic acids" a terminology muddle and a way out of it, Cell, 50:667, Aug. 28, 1987.*

(Continued)

*Primary Examiner* — Claire Kaufman
(74) *Attorney, Agent, or Firm* — The Webb Law Firm

(57) ABSTRACT

Provided are monospecific and bispecific proteins that bind specifically to OX40 and/or PD-L1. Exemplary proteins release the inhibition through PD-L1 and stimulate T cell through OX40. Exemplary polyvalent proteins comprise at least one OX40 binding site and at least one PD-L1 binding site. In certain embodiments, the binding sites may be linked through an immunoglobulin constant region. Anti-OX40 and anti-PD-L1 antibodies are also provided.

27 Claims, 33 Drawing Sheets

Specification includes a Sequence Listing.

(56) References Cited

U.S. PATENT DOCUMENTS

| | | | | |
|---|---|---|---|---|
| 9,175,082 | B2 | 11/2015 | Zhou et al. | |
| 9,475,880 | B2 | 10/2016 | Simons et al. | |
| 9,856,320 | B2 | 1/2018 | Cogswell et al. | |
| 10,058,609 | B2 * | 8/2018 | Zhou | C07K 16/28 |
| 10,457,732 | B2 | 10/2019 | Kasturirangan et al. | |
| 11,117,972 | B2 | 9/2021 | Eckelman et al. | |
| 2015/0307617 | A1 | 10/2015 | Du et al. | |
| 2016/0166685 | A1 | 6/2016 | Cheung et al. | |
| 2017/0198051 | A1 | 7/2017 | Eckelman et al. | |
| 2017/0275362 | A1 | 9/2017 | Brentjens et al. | |
| 2017/0281765 | A1 | 10/2017 | Zhou et al. | |
| 2018/0147271 | A1 | 5/2018 | Morgan et al. | |
| 2018/0327504 | A1 | 11/2018 | Al-Shamkhani et al. | |
| 2018/0346571 | A1 | 12/2018 | Gurney et al. | |
| 2019/0112380 | A1 | 4/2019 | Chaudhary | |
| 2020/0299389 | A1 | 9/2020 | Her et al. | |

FOREIGN PATENT DOCUMENTS

| | | | | |
|---|---|---|---|---|
| CN | 104736168 | A | 6/2015 | |
| CN | 106103486 | A | 11/2016 | |
| CN | 106999583 | A | 8/2017 | |
| CN | 107074953 | A | 8/2017 | |
| JP | 2008544755 | A | 12/2008 | |
| JP | 2011505836 | A | 3/2011 | |
| JP | 2013538057 | A | 10/2013 | |
| JP | 2014527814 | A | 10/2014 | |
| JP | 2015519375 | A | 7/2015 | |
| JP | 2017514461 | A | 6/2017 | |
| WO | 03106498 | A2 | 12/2003 | |
| WO | 2013038191 | A2 | 3/2013 | |
| WO | 2013181634 | A2 | 12/2013 | |
| WO | 2016090337 | A1 | 6/2016 | |
| WO | 2016187216 | A1 | 11/2016 | |
| WO | 2017068181 | A1 | 4/2017 | |
| WO | 2017087547 | A1 | 5/2017 | |
| WO | WO-2017096120 | A1 * | 6/2017 | A61K 39/39558 |
| WO | 2017123673 | A2 | 7/2017 | |
| WO | 2017172981 | A2 | 10/2017 | |
| WO | 2017193032 | A2 | 11/2017 | |
| WO | 2019168947 | A1 | 9/2019 | |
| WO | 2019184909 | A1 | 10/2019 | |

OTHER PUBLICATIONS

Pearson, W.R., An introduction to sequence similarity ("Homology") searching, Curr. Prot. Bioinformatics, 42:3.1.1-3.1.8, Jun. 2013.*

Kranz et al., Restricted reassociation of heavy and light chains from hapten-specific monoclonal antibodies, Proc. Natl. Acad. Sci. USA, 78(9):5807-5811, Spet. 1981.*

Nezlin, RS, Biochemistry of Antibodies, Plenum Press:New York, p. 160, 1970.*

MacCallum et al., Antibody-atnigen interactions: Contac analysis and binding site topolography, J. Mol. Miol. 262:732-745, 1996.*

Lamminmaki et al., Crystal structure of a recombinant anti-estradiol Fab fragment in compelxt with 17B-estradiol, J. Biol. Chem. 276 (39):36687-94, 2001.*

Chen et al., Enhancement and destruction of antibody function by somatic mutation: unequal occurrence is controlled by V gene combinatorial associationsEMBO J. 14 (12): 2784-2794, 1995.*

Dondelinger et al., Understanding the Significance and Implications of Antibody Numbering and Antigen-Binding Surface/Residue Definition Front. Immunol. 9:2278, doi.org/10.3389/fimmu.2018.02278, Oct. 16, 2018.*

Alves Costa Silva et al., "New pathways in immune stimulation: targeting OX40," ESMO Open, 2020, pp. 1-8, vol. 5, article No. e000573.

Bell et al., "OX40 signaling in head and neck squamous cell carcinoma: Overcoming immunosuppression in the tumor microenvironment," Oral Oncology, 2016, pp. 1-10, vol. 52.

Ramser et al., "High OX40 expression in recurrent ovarian carcinoma is indicative for response to repeated chemotherapy," BMC Cancer, 2018, pp. 1-9, vol. 18, article No. 425.

Yokouchi et al., "Anti-OX40 monoclonal antibody therapy in combination with radiotherapy results in therapeutic antitumor immunity to murine lung cancer," Cancer Sci, 2008, pp. 361-367, vol. 99:2.

"Atezolizumab", Wikipedia, pp. 1-5, retrieved from https://en.wikipedia.org/wiki/Atezolizumab on May 4, 2021.

Azevedo et al., "First-line atezolizumab monotherapy in patients with advanced BRAFV600 wild-type melanoma", Pigment Cell & Melanoma Research, 2021. [Abstract].

Bahleda et al.,"Long-Term Safety and Clinical Outcomes of Atezolizumab in Head and Neck Cancer: Phase Ia Trial Results", Annals of Oncology, Sep. 2017, pp. 373, vol. 28:5. [Abstract].

Geoerger et al., "Atezolizumab for children and young adults with previously treated solid tumours, non-Hodgkin lymphoma, and Hodgkin lymphoma (iMATRIX): a multicentre phase 1-2 study", The Lancet Oncology, 2019, pp. 134-144, vol. 21:1.

"Highlights of Prescribing Information: Tecentriq (atezolizumab) injection, for intravenous use", U.S. Food and Drug Administration, 2016, pp. 1-38.

Lafon et al., "Atezolizumab for the treatment of renal cell carcinoma", Expert Opinion on Biological Therapy, 2020, pp. 679-686, vol. 20:7.

Petrylak et al., "Safety and Clinical Activity of Atezolizumab in Patients with Metastatic Castration-Resistant Prostate Cancer: A Phase I Study", Clinical Cancer Research, 2021, pp. 3360-3369, vol. 27:12.

Rico et al., "Atezolizumab for the treatment of colorectal cancer: the latest evidence and clinical potential", Expert Opinion on Biological Therapy, 2018, pp. 449-457, vol. 18:4.

Bargou et al., "Tumor Regression in Cancer Patients by Very Low Doses of a T Cell-Engaging Antibody", Science, 2008, pp. 974-977, vol. 321, No. 5891.

Bretscher et al., "A Theory of Self-Nonself Discrimination", Science, 1970, pp. 1042-1049, vol. 169, No. 3950.

Bretscher, "A two-step, two-signal model for the primary activation of precursor helper T cells", Proceedings of the National Academy of Sciences of the United States of America, 1999, pp. 185-190, vol. 96, No. 1.

Chames et al., "Bispecific antibodies for cancer therapy: The light at the end of the tunnel?", mAbs, 2009, pp. 539-547, vol. 1, No. 6.

Croft, "Costimulation of T cells by OX40, 4-1 BB, and CD27", Cytokine & Growth Factor Reviews, 2003, pp. 265-273, vol. 14, Nos. 3-4.

Demarest et al., "Antibody therapeutics, antibody engineering, and the merits of protein stability", Current Opinion in Drug Discovery & Development, 2008, pp. 675-687, vol. 11, No. 5.

Fridman et al., "The immune contexture in human tumours: impact on clinical outcome", Nature Reviews, Cancer, 2012, pp. 298-306, vol. 12, No. 4.

Goldenberg et al., "Cancer imaging and therapy with bispecific antibody pretargeting", Update on Cancer Therapeutics, 2007, pp. 19-31, vol. 2, No. 1.

Heiss et al., "The trifunctional antibody catumaxomab for the treatment of malignant ascites due to epithelial cancer: results of a prospective randomized phase II/III trial", International Journal of Cancer, 2010, pp. 2209-2221, vol. 127, No. 9.

Hollander, "Bispecific antibodies for cancer therapy", Immunotherapy, 2009, pp. 211-222, vol. 1, No. 2.

Jenkins et al., "Antigen Presentation by Chemically Modified Splenocytes Induces Antigen-Specific T Cell Unresponsiveness in Vitro and in Vivo", Journal of Experimental Medicine, 1987, pp. 302-319, vol. 165, No. 2.

Karpovsky et al., "Production of target-specific effector cells using hetero-cross-linked aggregates containing anti-target cell and anti-Fc gamma receptor antibodies", Journal of Experimental Medicine, 1984, pp. 1686-1701, vol. 160, No. 6.

King et al., "A new Hu-PBL model for the study of human islet alloreactivity based on NOD-scid mice bearing a targeted mutation in the IL-2 receptor gamma chain gene", Clinical Immunology, 2008, pp. 303-314, vol. 126, No. 3.

(56) References Cited

OTHER PUBLICATIONS

Lafferty et al., "A New Analysis of Allogeneic Interactions", The Australian Journal of Experimental Biology and Medical Science, 1975, pp. 27-42, vol. 53, Pt. 1.
Larkin et al., "Combined Nivolumab and Ipilimumab or Monotherapy in Untreated Melanoma", The New England Journal of Medicine, 2015, pp. 23-34, vol. 373, No. 1.
Lenschow et al., "CD28/B7 System of T Cell Costimulation", Annual Review of Immunology, 1996, pp. 233-258, vol. 14.
Liang et al., "PD-L1 and PD-L2 have distinct roles in regulating host immunity to cutaneous leishmaniasis", European Journal of Immunology, 2006, pp. 58-64, vol. 36, No. 1.
Linch et al., "OX40 agonists and combination immunotherapy: putting the pedal to the metal", Frontiers in Oncology, 2015, 14 pages, vol. 5, Article No. 34.
Lu et al., "A Fully Human Recombinant IgG-like Bispecific Antibody to Both the Epidermal Growth Factor Receptor and the Insulin-like Growth Factor Receptor for Enhanced Antitumor Activity", The Journal of Biological Chemistry, 2005, pp. 19665-19672, vol. 280, No. 20.
Müller et al., "Improved Pharmacokinetics of Recombinant Bispecific Antibody Molecules by Fusion to Human Serum Albumin", The Journal of Biological Chemistry, 2007, pp. 12650-12660, vol. 282, No. 17.
Pardoll, "The blockade of immune checkpoints in cancer immunotherapy", Nature Review, Cancer, 2012, pp. 252-264, vol. 12, No. 4.
Paterson et al., "Antigens of Activated Rat T Lymphocytes Including a Molecule of 50,000 Mr Detected Only on CD4 Positive T Blasts", Molecular Immunology, 1987, pp. 1281-1290, vol. 24, No. 12.
Perez et al., "Specific targeting of cytotoxic T cells by anti-T3 linked to anti-target cell antibody", Nature, 1985, pp. 354-356, vol. 316, No. 6026.
Ridgway et al., "'Knobs-into-holes' engineering of antibody CH3 domains for heavy chain heterodimerization", Protein Engineering, 1996, pp. 617-621, vol. 9, No. 7.
Staerz et al., "Hybrid antibodies can target sites for attack by T cells", Nature, 1985, pp. 628-631, vol. 314, No. 6012.
Sznol et al., "Antagonist Antibodies to PD-1 and B7-H1 (PD-L1) in the Treatment of Advanced Human Cancer", Clinical Cancer Research, 2013, pp. 1021-1034, vol. 19, No. 5.
Thakur et al., "Cancer therapy with bispecific antibodies: Clinical experience", Current Opinion in Molecular Therapeutics, 2010, pp. 340-349, vol. 12, No. 3.
Topalian et al., "Survival, Durable Tumor Remission, and Long-Term Safety in Patients With Advanced Melanoma Receiving Nivolumab", Journal of Clinical Oncology, 2014, pp. 1020-1030, vol. 32, No. 10.
Watts, "TNF/TNFR Family Members in Costimulation of T Cell Responses", Annual Review of Immunology, 2005, pp. 23-68, vol. 23.
Weinberg et al., "Target Organ-Specific Up-Regulation of the MRC OX-40 Marker and Selective Production of Th1 Lymphokine mRNA by Encephalitogenic T Helper Cells Isolated from the Spinal Cord of Rats with Experimental Autoimmune Encephalomyelitis", Journal of Immunology, 1994, pp. 4712-4721, vol. 152, No. 9.
Bulliard et al., "OX40 engagement depletes intratumoral Tregs via activating FcyRs, leading to antitumor efficacy", Immunology and Cell Biology, 2014, pp. 475-480, vol. 92.
Lee et al. "Molecular mechanism of PD-1/PD-L1 blockade via anti-PD-L1 antibodies atezolizumab and durvalumab", Scientific Reports, pp. 1-12, vol. 7.
Yarilin, "The Principles of Immunology", Moscow: Meditsina, 1999, pp. 169-174, vol. 608.
Rudikoff et al., "Single amino acid substitution altering antigen-binding specificity," 1982, Proc Natl Acad Sci. USA, vol. 79, pp. 1979-1983.
Tamura et al., "Structural Correlates of an Anticarcinoma Antibody: Identification of Specificity-Determining Residues (SDRs) and Development of a Minimally Immunogenic Antibody Variant by Retention of SDRs Only," 2000, J Immunol., vol. 164, pp. 1432-1441.
Tingsong, "Advances in Treatment of Gastric Cancer", Tongji University Press, May 31, 2017, p. 144.
Zhang et al., "Fc Engineering Approaches to Enhance the Agonism and Effector Functions of an Anti-OX40 Antibody", Journal of Biological Chemistry, 2016, pp. 27134-27146, vol. 291(53).
Weinberg et al., "Anti-OX40 (CD134) administration to nonhuman primates: immunostimulatory effects and toxicokinetic study", Journal of Immunotherapy, Nov.-Dec. 2006, pp. 575-585, vol. 29(6).
Guo et al., "PD-1 Blockade and OX40 Triggering Synergistically Protects against Tumor Growth in a Murine Model of Ovarian Cancer", PLOS ONE, Feb. 27, 2014, vol. 9(2).
Granier et al., "Mechanisms of action and rationale for the use of checkpoint inhibitors in cancer", ESMO Open, 2017.
Shrimali et al., "Concurrent PD-1 Blockade Negates the Effects of OX40 Agonist Antibody in Combination Immunotherapy through Inducing T-cell Apoptosis", Cancer Immunology Research, 2017, pp. 755-766, vol. 5.
Hui et al., "Research on an anti-human OX40 eliciting monoclonal antibody and preliminary study on its biological ability", Modern Immunology, May 31, 2010, pp. 195-201, vol. 30(3), English-language Abstract.
Wei et al., "Comprehensive therapeutic strategies regarding immune checkpoint", Chin J Clin Oncol, Aug. 15, 2017, pp. 782-786, vol. 44(15), English-language Abstract.
Ping et al., "Research progress of new target OX40 in tumor immunotherapy", Chinese Journal of Microbiology and Immunology, Mar. 31, 2017, pp. 240-244, vol. 37(3), English-language Abstract.
Geng et al., "Advances in the application of bispecific antibody drugs", Progress in Biotechnology, Nov. 25, 2015, pp. 420-424, vol. 5(6), English-language Abstract.

* cited by examiner

Anti-PD-L1-OX40 Ab-V5

PD-L1 AND OX40 BINDING PROTEINS FOR CANCER REGULATION

CROSS-REFERENCE TO RELATED APPLICATIONS

This application is a continuation of International Application No. PCT/US2018/067868 filed Dec. 28, 2018, and claims priority to U.S. Provisional Patent Application No. 62/611,543 filed Dec. 29, 2017, the disclosures of which are hereby incorporated by reference in their entirety.

The Sequence Listing associated with this application is filed in electronic format via EFS-Web and is hereby incorporated by reference into the specification in its entirety. The name of the text file containing the Sequence Listing is 2002012_ST25.txt. The size of the text file is 125,973 bytes, and the text file was created on May 7, 2020.

BACKGROUND

Field of Invention

The present invention relates to an antibody. More particularly, the present invention relates to the antibody for cancer therapy.

Description of Related Art

The two major types of lymphocytes in humans are T (thymus-derived) and B (bone marrow derived. These cells are derived from hematopoietic stem cells in the bone marrow and fetal liver that have committed to the lymphoid development pathway. The progeny of these stem cells follow divergent pathways to mature into either B or T lymphocytes. Human B-lymphocyte development takes place entirely within the bone marrow. T cells, on the other hand, develop from immature precursors that leave the marrow and travel through the bloodstream to the thymus, where they proliferate and differentiate into mature T lymphocytes.

T cells

T-cells are the most abundant (about 75% of blood lymphocytes) and potent immune killer cells. The role of effector T-cells in the anti-tumor immune response is strongly supported by in vitro studies and the observation that a high infiltration of CD8+ T cells in several types of tumors correlates with a favorable clinical prognostic (Fridman et al., 2012). The activation of effector naive T-cells requires at least three complementary signals: (i) TCR-CD3/Ag-MHC interaction with the assistance of co-receptors (CD4 or CD8); (ii) binding of co-stimulatory molecules such as CD80 or CD86 to CD28, CD40/CD40 L; and (iii) accessory molecules such as cytokines.

Co-stimulation or the provision of two distinct signals to T-cells is a widely accepted model of lymphocyte activation of resting T lymphocytes by antigen-presenting cells (APCs) (Lafferty and Cunningham, 1975). This model further provides for the discrimination of self from non-self and immune tolerance (Bretscher and Cohn, 1970; Bretscher, 1999; Jenkins and Schwartz, 1987). The primary signal, or antigen specific signal, is transduced through the T-cell receptor (TCR) following recognition of foreign antigen peptide presented in the context of the major histocompatibility-complex (MHC). The second or co-stimulatory signal is delivered to T-cells by co-stimulatory molecules expressed on antigen-presenting cells (APCs), and induce T-cells to promote clonal expansion, cytokine secretion and effector function (Lenschow et al., 1996). In the absence of costimulation, T-cells can become refractory to antigen stimulation, do not mount an effective immune response, and further may result in exhaustion or tolerance to foreign antigens.

Immune Checkpoint Protein: PD-L1 and OX40

Immune checkpoints refer to a group of inhibitory and stimulatory pathways mostly initiated by ligand-receptor interaction hardwiring the immune system, specifically T-cell mediated immunity, to maintain self-tolerance and modulate the duration and amplitude of physiological responses in peripheral tissues in order to minimize collateral tissue damages normally (Pardoll, 2012). Tumor cells co-opt certain checkpoint pathways as a major mechanism of immune resistance. For example, programmed cell death protein 1 ligand, PD-L1, is commonly up-regulated on tumor cell surface of human cancers. The interaction of PD-L1 with its receptor, PD-1, expressed on tumor infiltrated lymphocytes (TILs), specifically on T cells, inhibits local T cell-mediated response to escape the immune surveillance (Liang et al., 2006; Sznol and Chen, 2013). Thus, the inhibition of immunosuppressive signals on cancer cells, or direct agonistic stimulation of T cells, results in and/or induces a strong sustained anti-tumor immune response. Recent clinical studies strongly suggested blockage of immune checkpoint proteins via antibody or modulated by soluble ligands or receptors are the most promising approaches to activating therapeutic antitumor immunity (Topalian et al., 2014). Currently, anti-PD-1 and anti-CTLA-4 (cytotoxic T-lymphocyte-associated antigen-4) antibodies have been approved by FDA to treat diseases such as melanomas.

Another co-stimulator molecule is the OX40 receptor (CD134), a member of the TNFR superfamily, which is membrane-bound and is expressed primarily on activated CD4+ T cells (Paterson et al., 1987). Signaling through the OX40 receptor (hereinafter "OX40") is costimulatory to effector T cells and causes proliferation of T-cells (Watts, 2005; Weinberg et al., 1994). Studies of OX40 suggest that its major role is to dictate the number of effector T-cells that accumulate in primary immune responses, and consequently to govern the number of memory T-cells that subsequently develop and survive (Croft, 2003). A number in vitro studies have been shown that OX40 provides a costimulatory signal resulting, in enhanced T cell proliferation and cytokine production.

Bi-Specific/Bi-Functional Antibody

The idea of using bispecific antibodies to efficiently retarget effector immune cells toward tumor cells emerged in the 1980s (Karpovsky et al., 1984; Perez et al., 1985; Staerz et al., 1985). Bispecific scaffolds are generally classified in two major groups with different pharmacokinetic properties, based on the absence or presence of an Fc fragment, IgG-like molecules and small recombinant bispecific formats, most of them deriving from single chain variable fragment (scFv). Through their compact size, antibody fragments usually penetrate tumors more efficiently than IgG-like molecules but this benefit is mitigated by a short serum half-life (few hours) limiting their overall tumor uptake and residence time (Goldenberg et al., 2007). By contrast, the presence of an Fc fragment, which binds to the neonatal Fc receptors, provides a long serum half-life (>10 days) to the IgG-like formats, favoring tumor uptake and retention, but limits tumor penetration.

Recent studies have highlighted the therapeutic efficacy of immunotherapy, a class of cancer treatments that utilize the patient's own immune system to destroy cancerous cells.

Within a tumor the presence of a family of negative regulatory molecules, collectively known as "checkpoint inhibitors," can inhibit T cell function to suppress anti-tumor immunity. Checkpoint inhibitors, such as CTLA-4 and PD-1, attenuate T cell proliferation and cytokine production. Targeted blockade of CTLA-4 or PD-1 with antagonist monoclonal antibodies (mAbs) releases the "brakes" on T cells to boost anti-tumor immunity. Generating optimal "killer" CD8 T cell responses also requires T cell receptor activation plus co-stimulation, which can be provided through ligation of tumor necrosis factor receptor family members, including OX40 (CD134) and 4-1 BB (CD137). OX40 is of particular interest as treatment with an activating (agonist) anti-OX40 mAb augments T cell differentiation and cytolytic function leading to enhanced anti-tumor immunity against a variety of tumors. When used as single agents, these drugs can induce potent clinical and immunologic responses in patients with metastatic disease (Linch et al., 2015).

SUMMARY

The present disclosure designed to investigate the bispecific antibody with immunomodulatory aiming for the treatment of patient with cancers, such as prostate cancer, lung cancer, NSCLC, melanoma, lymphoma, breast cancer, head and neck cancer, RCC, or ovarian cancer were examined.

The present disclosure provides an antibody or an antigen-binding portion thereof binding to OX40 (CD134), comprising: a heavy chain variable region comprising an amino acid sequence of at least about 80% sequence homology to the amino acid sequence selected from the group consisting of SEQ ID NO: 6, SEQ ID NO: 8, amino acid 128-246 of SEQ ID NO: 10, and amino acid 124-241 SEQ ID NO: 13; and a light chain variable region comprising an amino acid sequence of at least about 80% homology to the amino acid sequence selected from the group consisting of amino acid 1-108 of SEQ ID NO: 5, 1-108 of SEQ ID NO: 7, 1-112 of SEQ ID NO: 10, and 1-108 of SEQ ID NO: 13.

In one embodiment, the antibody or the antigen-binding portion thereof is a single chain variable fragment (scFv) sequence selected from the group consisting of SEQ ID NO: 10, 11, 12, and 13.

In one embodiment, the antibody or the antigen-binding portion thereof is a bispecific antibody.

In one embodiment, the bispecific antibody comprises an immune checkpoint protein binding site.

In one embodiment, the immune checkpoint protein binding site comprises a programmed cell death protein 1 ligand (PD-L1) binding site, PD-1 binding site, epidermal growth factor receptor (EGFR) binding site, human epidermal growth factor receptor 2 (HER2) binding site, cytotoxic T-lymphocyte-associated antigen 4 (CTLA-4) binding site, or lymphocyte activation gene 3 (LAG3) binding site.

The present disclosure also provides an antibody or an antigen-binding portion thereof binding to PD-L1, comprising: a heavy chain variable domain comprising an amino acid sequence of at least about 80% sequence homology to the amino acid sequence selected from the group consisting of SEQ ID NO: 2 and SEQ ID NO: 4; and a light chain variable domain comprising an amino acid sequence of at least about 80% homology to the amino acid sequence selected from the group consisting of amino acid 1-111 of SEQ ID NO: 1 and 1-110 of SEQ ID NO: 3.

The present disclosure also provides a bispecific antibody comprising at least one of polypeptide chain, wherein the polypeptide chain comprises an OX40 binding site and a PD-L1 binding site. The OX40 binding site comprises a heavy chain variable region comprising an amino acid sequence of at least about 80% sequence homology to the amino acid sequence selected from the group consisting of SEQ ID NO: 6, SEQ ID NO: 8, amino acid 128-246 of SEQ ID NO: 10, and amino acid 124-241 SEQ ID NO: 13; and a light chain variable region comprising an amino acid sequence of at least about 80% homology to the amino acid sequence selected from the group consisting of amino acid 1-108 of SEQ ID NO: 5, 1-108 of SEQ ID NO: 7, 1-112 of SEQ ID NO: 10 and 1-108 of SEQ ID NO: 13. The PD-L1 binding site comprises a heavy chain variable domain comprising an amino acid sequence of at least about 80% sequence homology to the amino acid sequence selected from the group consisting of SEQ ID NO: 2 and SEQ ID NO: 4; and a light chain variable domain comprising an amino acid sequence of at least about 80% homology to the amino acid sequence selected from the group consisting of amino acid 1-111 of SEQ ID NO: 1 and 1-110 of SEQ ID NO: 3.

In one embodiment, the polypeptide chain further comprises a Fc domain, a Fab fragment, and a scFv. The Fab fragment is connected to the N-terminus of the Fc domain, and the Fab fragment comprises the PD-L1 binding site. The scFv is connected to the C-terminus of the Fc domain, and the scFv comprises the OX40 binding site.

In one embodiment, the polypeptide chain further comprises a linker between the Fc domain and the scFv.

In one embodiment, the scFv comprises an amino acid sequence selected from the group consisting of amino acid 455-707 of SEQ ID NO: 18, 455-708 of SEQ ID NO: 19, 455-701 of SEQ ID NO: 20, 455-706 of SEQ ID NO: 21, 455-706 of SEQ ID NO: 22, 455-706 of SEQ ID NO: 23, 455-706 of SEQ ID NO: 24, 455-706 of SEQ ID NO: 25, 455-706 of SEQ ID NO: 26, 455-706 of SEQ ID NO: 27, 455-706 of SEQ ID NO: 28, and 455-706 of SEQ ID NO: 29.

In one embodiment, the bispecific antibody comprises one pairs of polypeptide chains.

In one embodiment, the bispecific antibody is an IgG, IgE, IgM, IgD, IgA, or IgY antibody.

In one embodiment, the bispecific antibody is an IgG antibody.

In one embodiment, the IgG antibody is an IgG1, IgG2, IgG3, or IgG4 antibody.

The present disclosure also provides an antibody-drug conjugate comprising a therapeutic agent, and an antibody or an antigen-binding portion binding PD-L1 and/or OX40, wherein the therapeutic agent is covalently conjugated to the antibody or the antigen-binding portion by a linker.

In one embodiment, the antibody or an antigen-binding portion is selected from the above mentioned antibody or an antigen-binding portion.

The present disclosure also provides a pharmaceutical composition comprising the antibody, the antigen-binding portion thereof, or the bispecific antibody as above mentioned, and at least one pharmaceutically acceptable carrier.

The present disclosure also provides a method of treating cancer comprising administering to the subject in need thereof an effective amount of the antibody, the antigen-binding portion thereof, or the bispecific antibody as above mentioned.

In one embodiment, the cancer is selected from the group consisting of prostate cancer, lung cancer, Non-Small Cell Lung Cancer (NSCLC), melanoma, lymphoma, breast cancer, head and neck cancer, renal cell carcinoma (RCC), and ovarian cancer.

The present disclosure also provides a nucleic acid molecule encoding the antibody, the antigen-binding portion thereof, or the bispecific antibody as above mentioned.

It is to be understood that both the foregoing general description and the following detailed description are by examples, and are intended to provide further explanation of the invention as claimed.

BRIEF DESCRIPTION OF THE DRAWINGS

The invention can be more fully understood by reading the following detailed description of the embodiment, with reference made to the accompanying drawings as follows.

DETAILED DESCRIPTION

Figure 1:
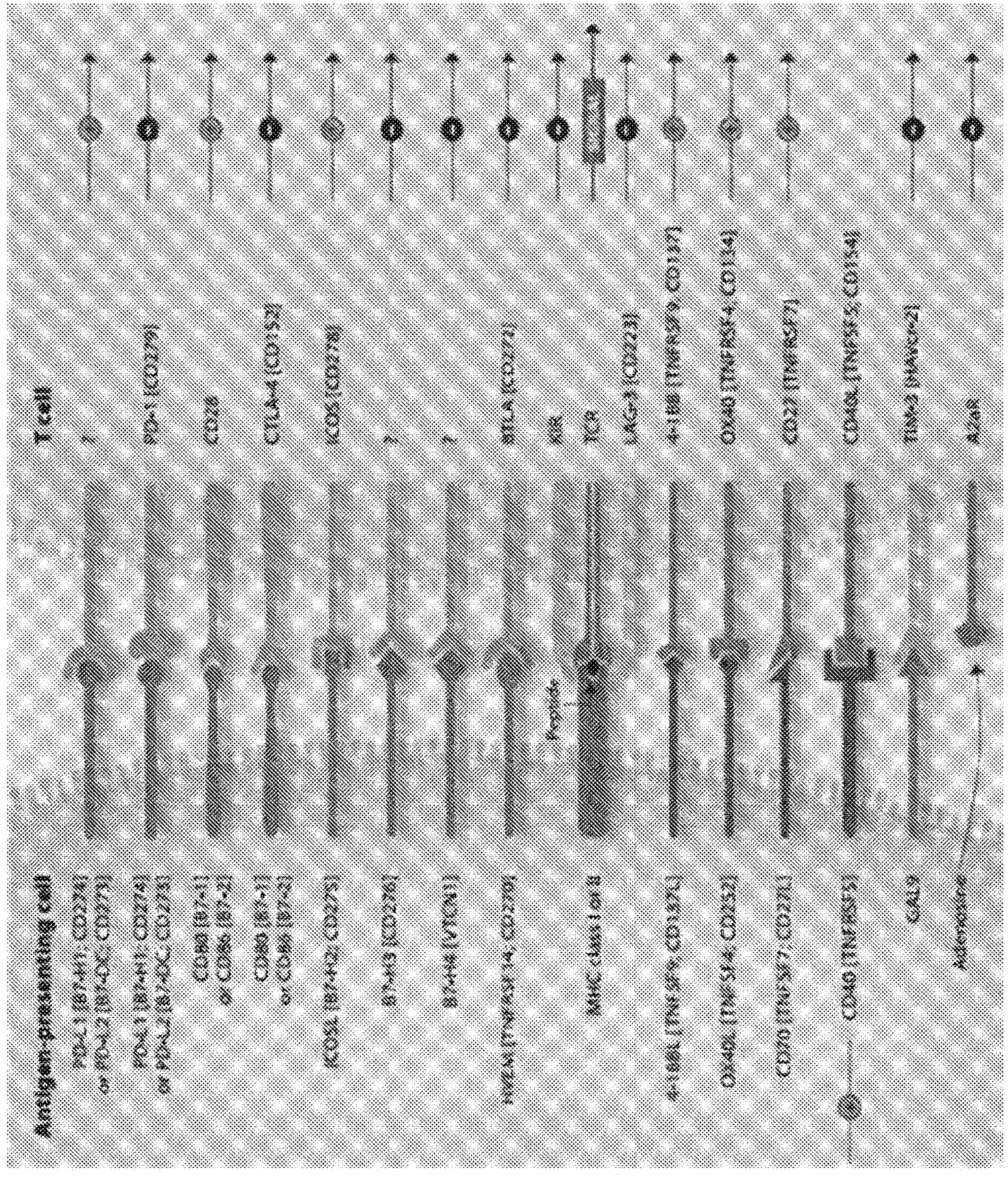
FIG. 1 shows immune checkpoints modulating T-cell mediated immunity. Antibody either agonistic or antagonistic against the checkpoints, such as anti-ICOS, anti-CD28, anti-OX40, and anti-CD27, or anti-PD-1, anti-CTLA4, anti-LAG3, anti-BTLA, could be used to construct the bi-functional fusion protein depending on applications.
Figure 2A:
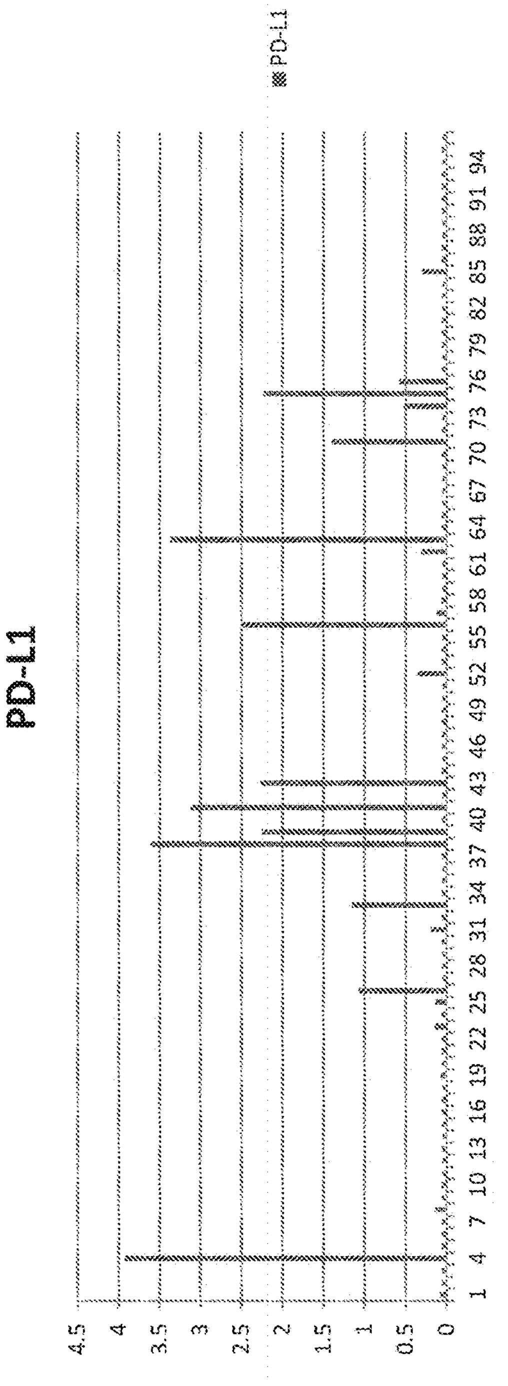
FIGS. 2A and 2B show the screening of phage clone by direct ELISA for PD-L1 expressed HEK293 cells.
Figure 2B:
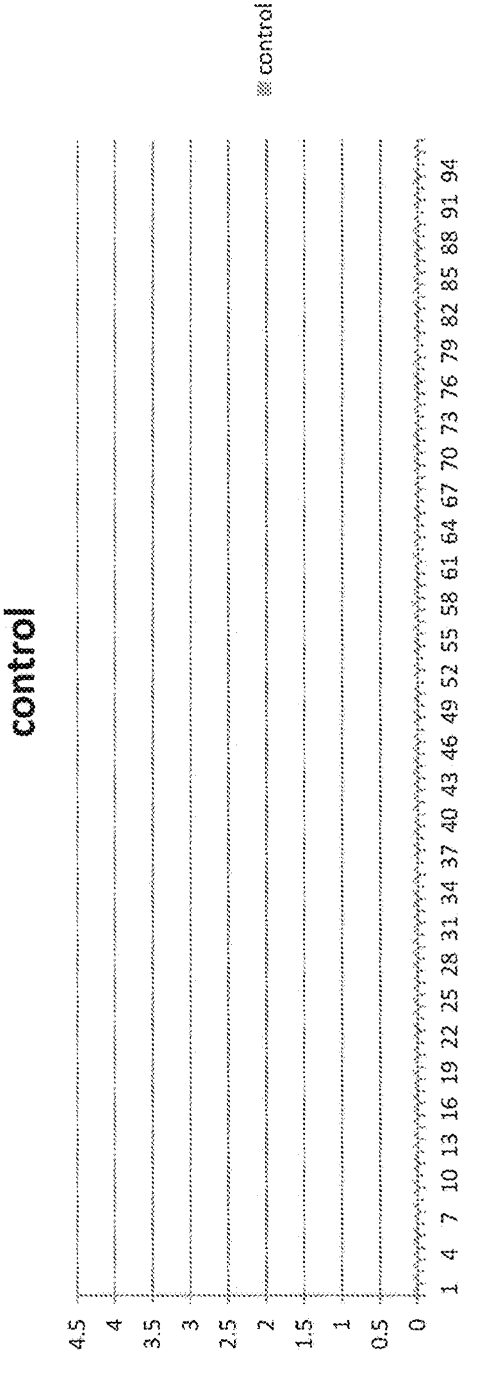
Figure 3A:
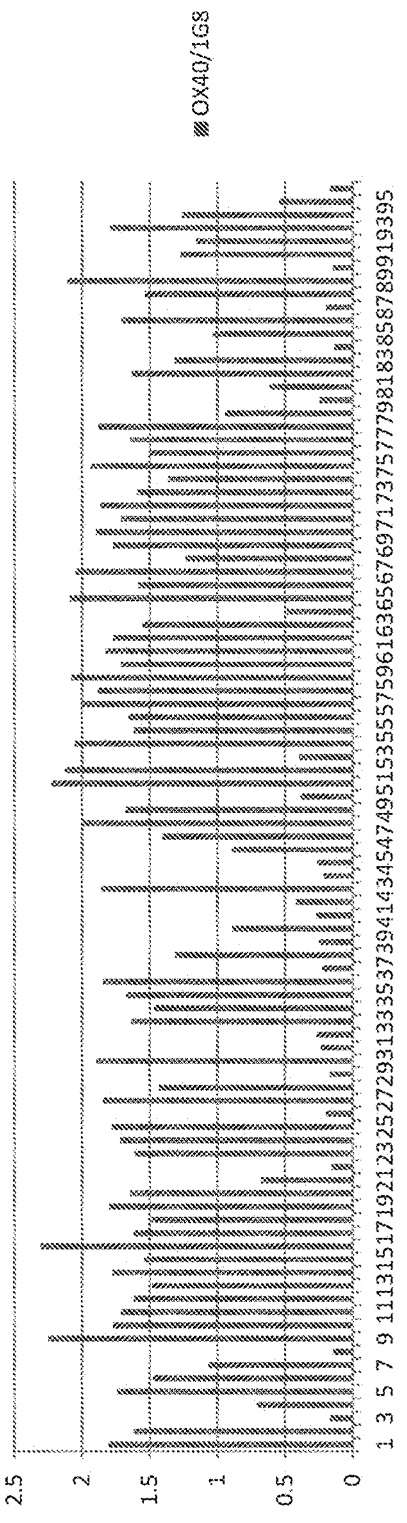
FIGS. 3A and 3B show the screening of phage clone by cell-based ELISA with OX40 expressed HEK293 cells.
Figure 3B:
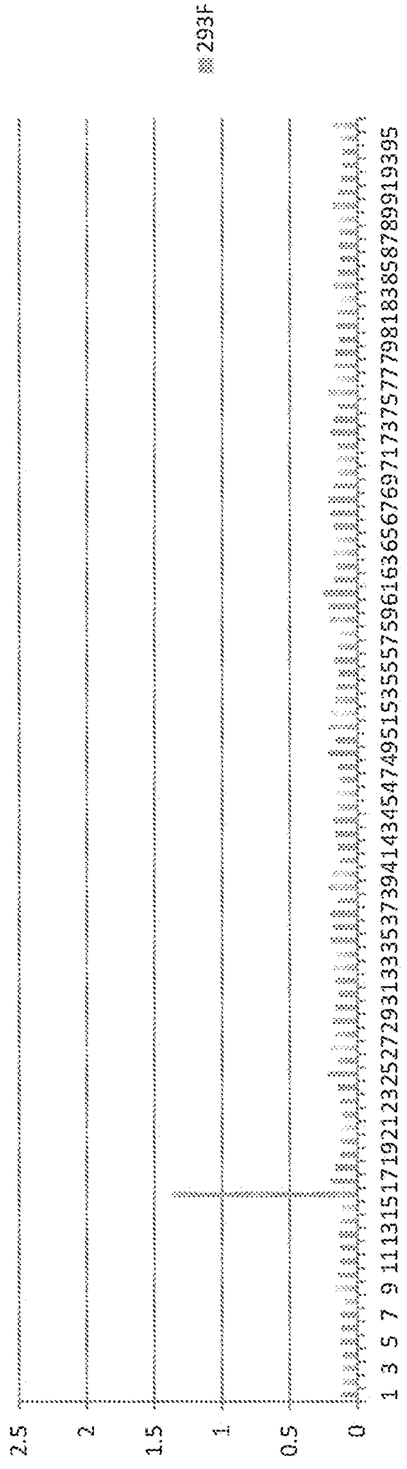

Reference will now be made in detail to the present embodiments of the invention, examples of which are illustrated in the accompanying drawings. Wherever possible, the same reference numbers are used in the drawings and the description to refer to the same or like parts.

The present invention describes the expression, purification and characterization of bi-functional proteins with isolated functional agonistic OX40 scFv fused to the C-terminus of Fc domain of anti-immune checkpoint protein antibodies. These proteins interact with its corresponding check point target shall transmit the inhibitory or stimulatory signal to modulate T-cell involved immunity. The components of Fc fusion proteins in present invention are of all human origins, and thus are expected to be non-immunogenic and can be used as therapeutics in human.

Bispecific molecules such as bispecific antibodies (BsAbs) provide a means of simultaneously targeting multiple epitopes on the same molecular target or different targets with a single therapeutic agent. As cancer therapeutics, they have the potential to confer novel or more potent activities, lower the cost of goods and facilitate the development of new therapeutic regimens in contrast to a mixture of two mAbs (Chames and Baty, 2009; Hollander, 2009; Thakur and Lum, 2010). Recently, catumaxomab, a trifunctional bispecific antibody targeting human epithelial cell adhesion molecule (EpCAM) and CD3 has shown a clear clinical benefit in patients with peritoneal carcinomatosis of epithelial cancers (Heiss et al., 2010), and a bispecific T-cell engaging (BiTE) antibody with dual specificity for CD19 and CD3 has also demonstrated encouraging clinical activity in patients with CD19 expressing hematological malignancies (Bargou et al., 2008). Despite strong interest in the development of bispecific molecules as cancer therapeutics, technical challenges in the production of stable and active bispecific molecules have in the past hindered the clinical evaluation of most bispecific formats. Many engineered antibody formats, including an IgG-like bispecific antibody have compromised stability or solubility (Bargou et al., 2008; Demarest and Glaser, 2008; Lu et al., 2005). Furthermore, several strategies have been taken to increase the product quality and in vivo stability of bispecific molecules, including PEGylation, conjugation with human serum albumin and Fc engineering (Muller et al., 2007; Ridgway et al., 1996). Bispecific single chain antibodies of the general form described above have the advantage that the nucleotide sequence encoding the four V-domains, two linkers and one spacer can be incorporated into a suitable host expression organism under the control of a single promoter. This increases the flexibility with which these constructs can be designed as well as the degree of experimenter control during their production. In addition, the Fc of IgG is a very another attractive scaffold for designing novel therapeutics because it contains all antibody functions except the binding ability. Fc engineering is important for improving the effectiveness of the bispecific antibodies. Therefore, the IgG-based conformation is using in present invention for two independent target on immune cells or target cell in immunotherapy.

Targeting immune-check point proteins are promising approaches to activate antitumor immunity. Anti-check point proteins, such as PD-1, PD-L1, CTLA-4, LAG3, etc., are currently evaluated clinically (FIG. 1). Preliminary data with blockers of immune checkpoint proteins have been shown to be able to enhance antitumor immunity with the potential to produce durable clinical responses. However, despite the remarkable clinical efficacy of these agents in a number of malignancies, it has become clear that they are not sufficiently active for many patients. Numerous additional immunomodulatory pathways as well as inhibitory factors expressed or secreted by myeloid and stromal cells in the tumor microenvironment are potential targets for synergizing with immune checkpoint blockade. Therefore, combining anticancer or bispecific antibody therapies has been essential to achieve complete remission and cures for patients with cancer.

The present invention describes the construction, expression and characterization of anti-immune checkpoint protein antibody Fc fused with different immune checkpoint protein specific scFv protein. The C-terminally positioned OX40 scFv in fusion constructs shall allow expanding the power of fusion proteins beyond OX40 activation approach if the fusion counterpart is immune system potentiating agent, such as anti-EGFR, anti-HER2, or anti-CTLA-4 antibody, for example.

Antibody Generation from OmniMab Library

For the generation of therapeutic antibodies against PD-L1 or OX40, selections with the OmniMab phagemid library were carried out. The phagemid library is generated by AP Biosciences Inc. (APBio Inc.) from a collection of over hundred health donors B cells. Phages for the 1st round of pannings were prepared by Hyperphage (M13K07ΔpIII, Progen, Heidelberg, Germany). Solid phase panning and cell panning against PD-L1 or OX40 were applied for PD-L1 or OX40 specific binder selection and isolation from OmniMab library. Solid phase panning was performed using recombinant human PD-L1-Fc or OX40-Fc (APBio Inc.) in the first round selection and then HEK293 cells expressed PD-L1 or OX40 were used for two and three round enrichment. After three rounds selection, the specific PD-L1 or OX40 binders were screened and isolated by direct ELISA or cell-based ELISA with corresponding recombinant protein (FIGS. 2A, 2B, 3A, and 3B). Pre-coated PD-L1-Fc recombinant proteins or OX40 expressed 293 cells were blotted with supernatant containing rescued phages for 1 hour and washed with PBS containing 0.1% Tween-20 for three times. Bound phages were detected by HRP conjugated anti-M13 antibody (Roche) and TMB substrate was used for signal development. The OD450 readings were recorded. The positive binders were isolated and sent for sequencing to confirm the sequence and diversity of heavy chain and light chain. The variable region of heavy chain and light chain specific to PD-L1 or OX40 were described from the SEQ ID NO: 1 to SEQ ID NO: 8: SEQ ID NO: 1 is the light chain of PD-L1 clone 6, SEQ ID NO: 2 is the variable region of heavy chain of PD-L1 clone 6, SEQ ID NO: 3 is the light chain of PD-L1 clone 32, SEQ ID NO: 4 is the variable region of heavy chain of PD-L1 clone 32, SEQ ID NO: 5 is the light chain of OX40 clone B17, SEQ ID NO: 6 is the variable region of heavy chain of OX40 clone B17, SEQ ID NO: 7 is the light chain of OX40 clone B19, SEQ ID NO: 8 is the variable region of heavy chain of OX40 clone B19. As shown in the FIGS. 2A, 2B, 3A and 3B, several clones were isolated and known to be recognized specifically for corresponding antigen as comparing with negative control.

Figure 4:
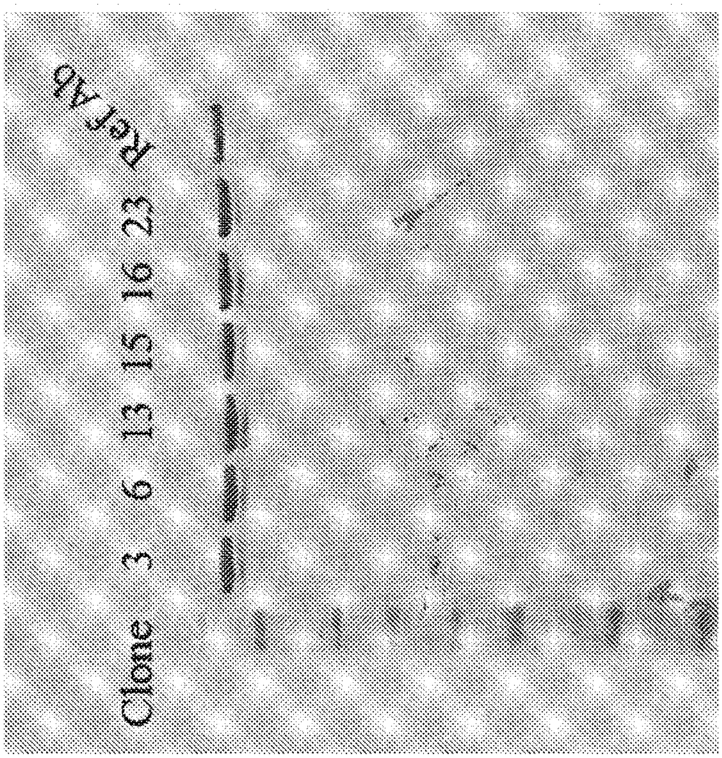
FIG. 4 shows purified antibody leads specific for PD-L1 by SDS-PAGE with non-reducing reagent to reveal the integrity and purity.
Figure 5:
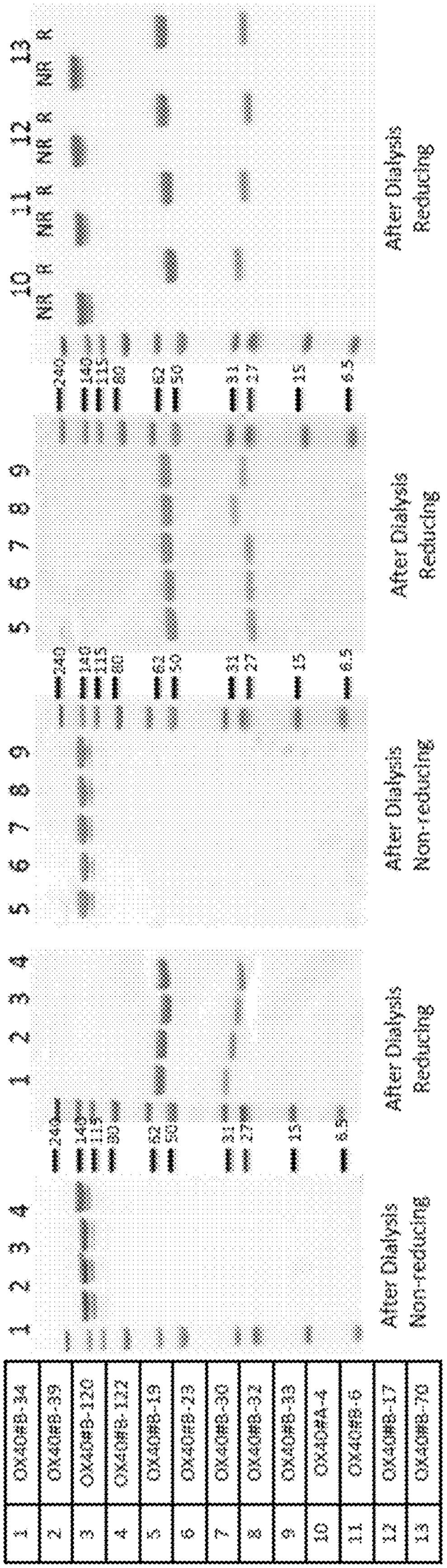
FIG. 5 shows purified antibody leads specific for OX40 by SDS-PAGE with non-reducing or reducing reagent to reveal the integrity and purity.

Subcloning and Expression/Purification of Selected PD-L1 or OX40 Specific Binder as IgG Format To facilitate the quick screening of specific binder with functionality in T cell activation, the heavy chains and light chains of positive binders against PD-L1 or OX40 by ELISA were then amplified, digested and sub-clone into APBio specialized IgG expression vector carrying IgG4 constant region (SEQ ID NO: 9). After sequence validation, the plasmids were then prepared and transfected into HEK293 cells for antibody expression with 293 fectin transfection reagent (Invitrogen). After 4 days culture, the antibody secreted into serum-free medium is affinity purified from culture supernatant by Protein G chromatography. Purified antibody is then concentrated, followed by dialysis in PBS buffer. The final concentration of dialyzed protein is determined by NanoDrop2000 spectrophotometer and the purity and integrity are determined by SDS-PAGE with or without reducing reagent as shown in the FIGS. 4 and 5. The integrity of various purified antibody leads, either PD-L1 specific or OX40 specific, is normal in the HEK293 cells as well as reference antibody, MPDL3280A for PD-L1 or GSK3174998 for OX40.

In one embodiment, the present disclosure provides an antibody or an antigen-binding portion thereof binding to OX40 (CD134), comprising a heavy chain variable region and a light chain variable region. The heavy chain variable region comprises an amino acid sequence of at least about 80% sequence homology to the amino acid sequence selected from the group consisting of SEQ ID NO: 6, SEQ ID NO: 8, amino acid 128-246 of SEQ ID NO: 10, and amino acid 124-241 SEQ ID NO: 13. In some examples, the heavy chain variable region comprises an amino acid sequence of at least about 85%, 90%, or 95% sequence homology to the amino acid sequence as above mentioned. The light chain variable region comprising an amino acid sequence of at least about 80% homology to the amino acid sequence selected from the group consisting of amino acid 1-108 of SEQ ID NO: 5, 1-108 of SEQ ID NO: 7, 1-112 of SEQ ID NO: 10, and 1-108 of SEQ ID NO: 13. In some examples, the light chain variable region comprises an amino acid sequence of at least about 85%, 90%, or 95% sequence homology to the amino acid sequence as above mentioned.

In one embodiment, the present disclosure provides an antibody or an antigen-binding portion thereof binding to PD-L1, comprising a heavy chain variable domain and a light chain variable domain. The heavy chain variable domain comprises an amino acid sequence of at least about 80% sequence homology to the amino acid sequence selected from the group consisting of SEQ ID NO: 2 and SEQ ID NO: 4. In some examples, the heavy chain variable region comprises an amino acid sequence of at least about 85%, 90%, or 95% sequence homology to the amino acid sequence as above mentioned. The light chain variable domain comprises an amino acid sequence of at least about 80% homology to the amino acid sequence selected from the group consisting of amino acid 1-111 of SEQ ID NO: 1 and 1-110 of SEQ ID NO: 3. In some examples, the light chain variable region comprises an amino acid sequence of at least about 85%, 90%, or 95% sequence homology to the amino acid sequence as above mentioned.

Figure 6:
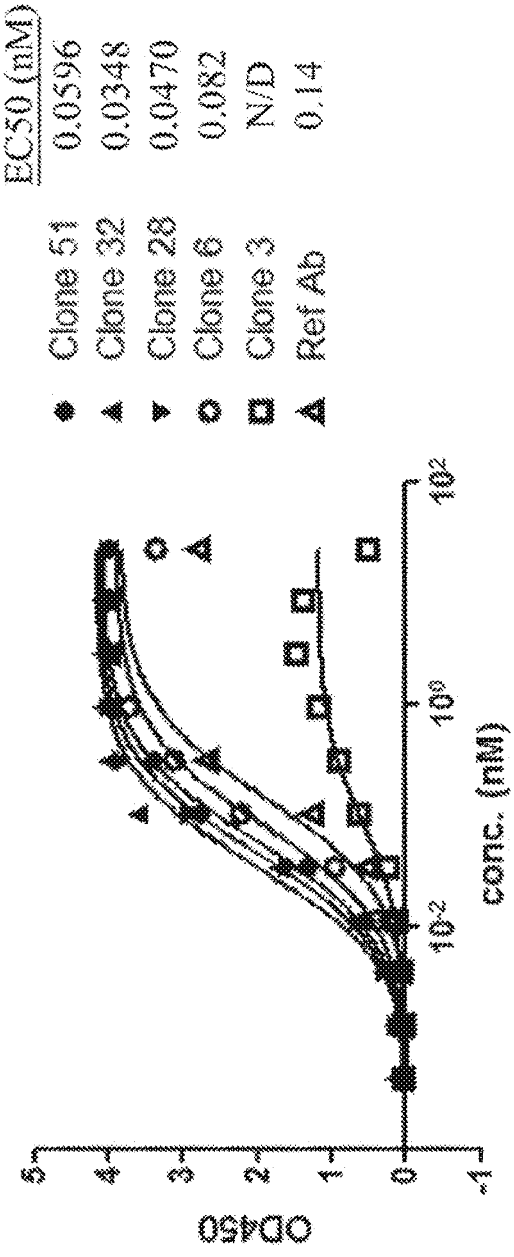
FIG. 6 shows examples of the direct ligand binding activity of purified anti-immune check point proteins and anti-PD-L1 antibody leads against PD-L1. Ligand pre-coated wells were first incubated with various concentrations of antibody leads as indicated. The bound proteins were then detected with HRP conjugated goat anti-human IgG Fab specific antibody and $OD_{450}$ readings were plotted.
Figure 7:
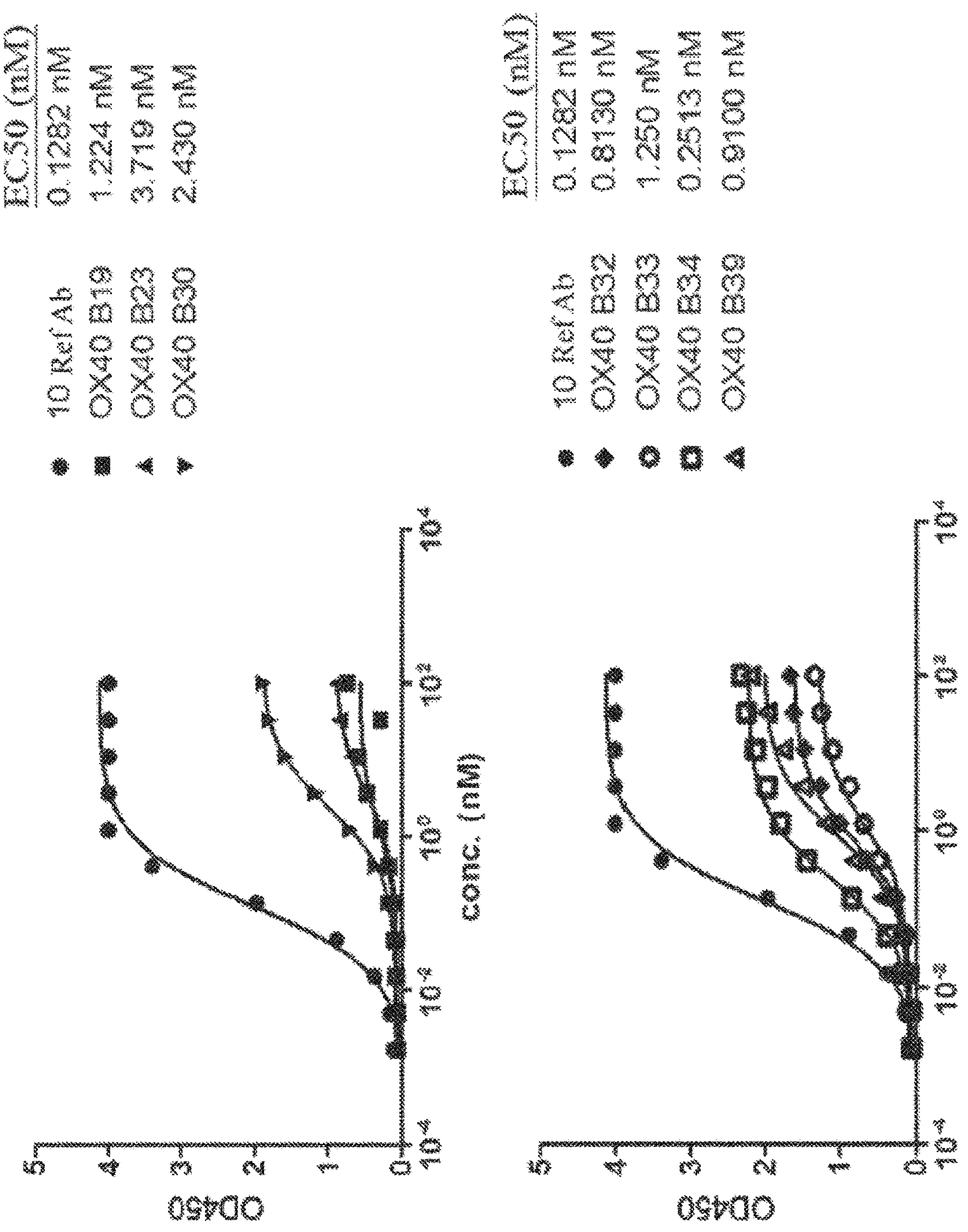
FIG. 7 shows examples of the direct ligand binding activity of purified anti-immune check point proteins and anti-OX40 antibody leads against OX40. Ligand pre-coated wells were first incubated with various concentrations of antibody leads as indicated. The bound proteins were then detected with HRP conjugated goat anti-human IgG Fab specific antibody and $OD_{450}$ readings were plotted.

Binding Activity Determination for PD-L1, OX40 Specific IgG Leads by Direct ELISA Purified antibody leads against PD-L1 or OX40 (anti-PD-L1 antibody leads or anti-OX40 antibody leads) were then applied for ELISA binding characterization on human PD-L1-Fc or OX40-Fc in a direct coated setup. FIGS. 6 and 7 showed the ELISA binding result for anti-PD-L1 and anti-OX40 antibodies, respectively. For PD-L1 specific antibodies, most leads showed a similar or better binding activity with reference antibody (Ref Ab, MPDL3280A, Roche).

Purified human PD-L1 or OX40 IgG1 Fc chimera (PD-L1-Fc or OX40-Fc, APBio) was dialyzed in Phosphate Buffered Saline (PBS), adjusted to 1 mg/mL and then diluted with PBS to a final concentration of 1 μg/mL. Nunc-Immuno Maxisorp 96 well plates were coated with 0.1 mL per well of recombinant PD-L1-Fc or OX40-Fc chimera leaving empty wells for nonspecific binding controls and incubated at 4° C. overnight. The PD-L1-Fc or OX40-Fc chimera solution was removed and the plates were washed three times with 0.4 mL wash buffer (0.1% Tween-20 in PBS). 0.4 mL blocking buffer (5% low-fat milk powder in PBS) was added to all wells and incubated at room temperature for 1 hour with mixing. The blocking buffer was removed and plates washed three times with 0.4 mL wash buffer. Serial dilutions of the PD-L1 or OX40 test antibodies were prepared in PBS and 0.1 mL diluted Ab was added per well. Plates were incubated 1 hour at room temperature. Antibody solution was removed and the plates washed three time with 0.4 mL wash buffer per well. Horseradish peroxidase labeled goat anti-human IgG, $F(ab')_2$ specific $F(ab')_2$ antibody (Jackson Immunoresearch #109-036-097) was diluted 1:2000 with PBS and added 0.1 mL per well. The plates were incubated 1 hour at room temperature and washed with 0.4 mL per well wash buffer. 0.1 mL TMB reagent (Invitrogen) was added and incubated for 1 to 5 minutes at room temperature. The reaction was stopped by adding 0.05 mL 1N HCl and absorbance was read at 450 nm on a Bio-Tek Spectra. Calculated EC50 for anti-PD-L1antibody leads to PD-L1 showed most leads possess good binding activity as well as MPDL3280A (Ref Ab) by direct ELISA (FIG. 6). On the contrary, most anti-OX40 antibody leads showed much lower binding activity as comparing with reference antibody (Ref Ab, GSK3174998)(FIG. 7).

Binding Activity Determination for PD-L1 and OX40 Specific IgG Leads by FACS

Figure 8:
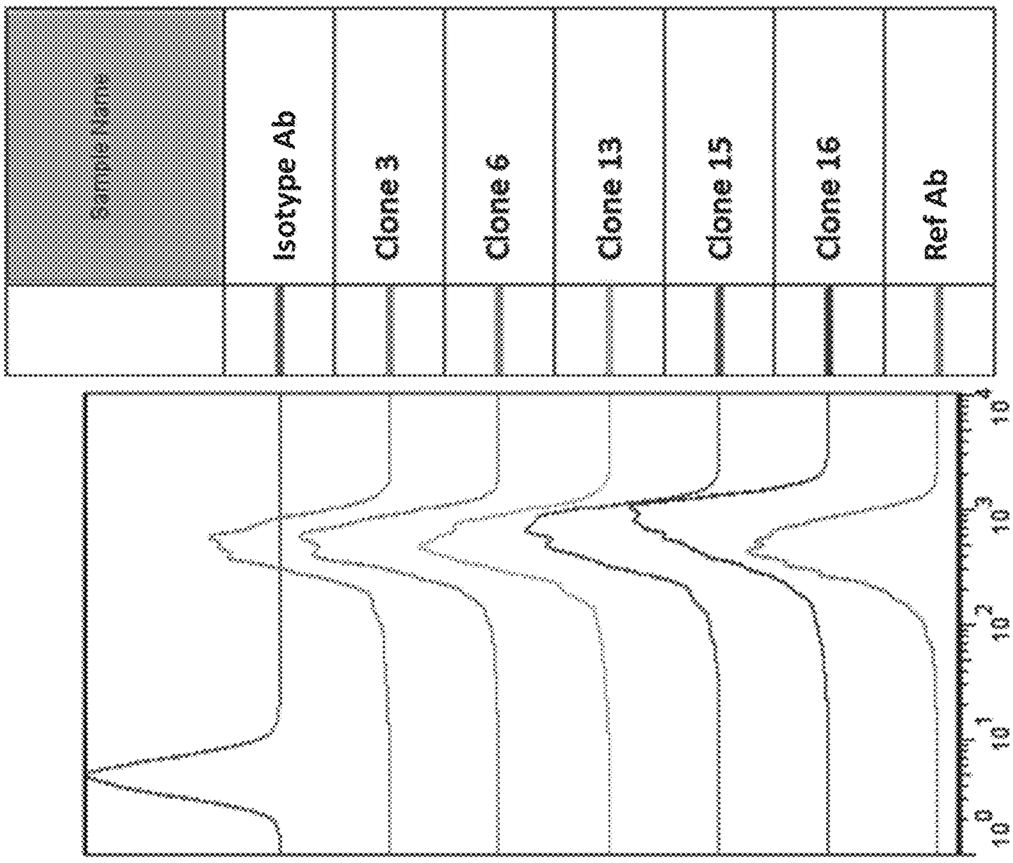
FIG. 8 shows the flow analysis using PD-L1expression 293 cells. PD-L1 expression HEK293 cells were first incubated with purified antibody leads, and the bound antibodies were detected with Alexa-488 conjugated goat anti-human IgG (H+L) followed by fluorescence-activated cell sorter (FACS) analysis.
Figure 9:
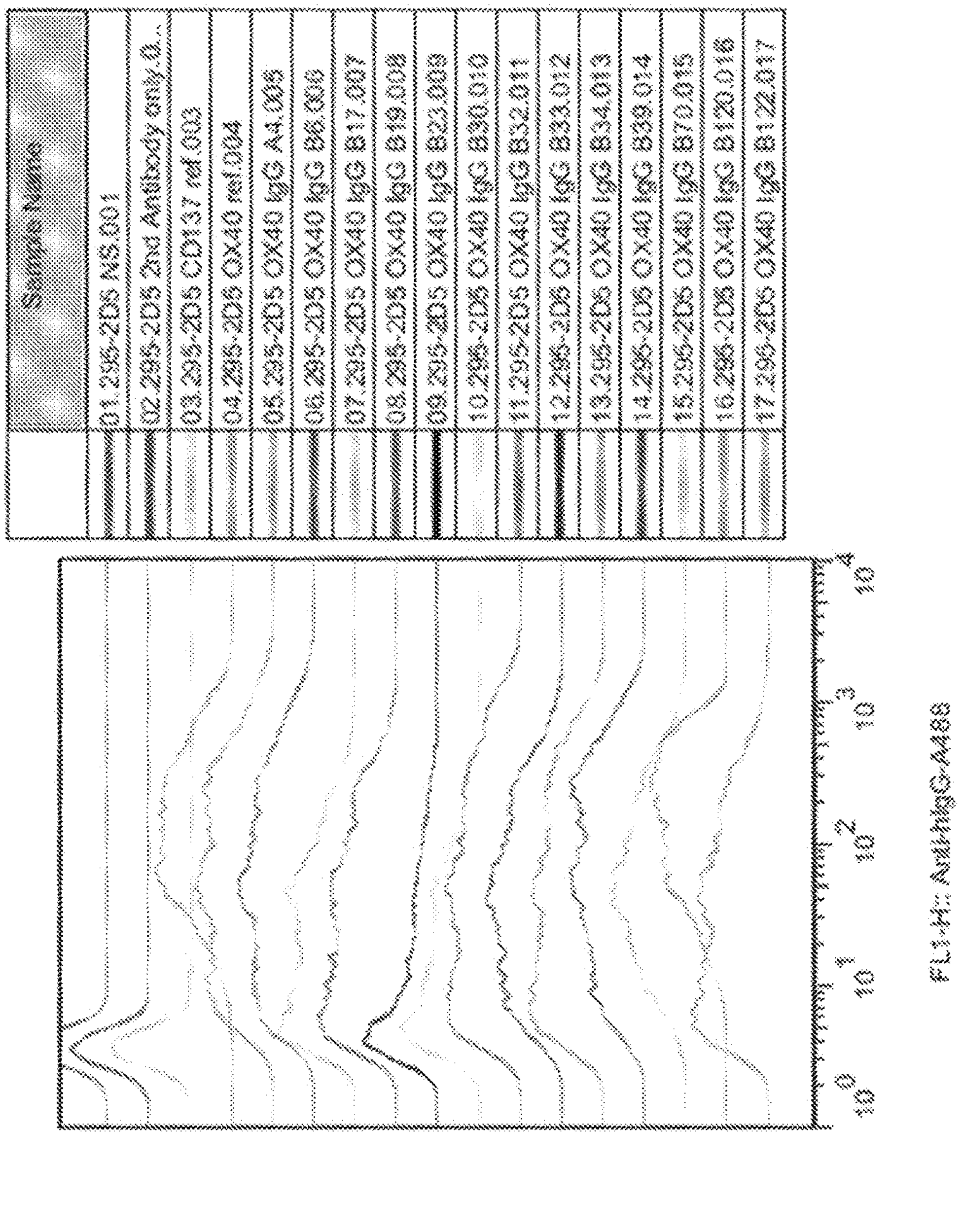
FIG. 9 shows the flow analysis using OX40 expression 293 cells. OX40 expression HEK293 cells were first incubated with purified anti-OX40 antibody leads, and the bound antibodies were detected with Alexa-488 conjugated goat anti-human IgG (H+L) followed by FACS analysis. NS: no staining.

Purified antibody leads (anti-PD-L1 antibody leads or anti-OX40 antibody leads) were also applied for flow cytometry to determine and compare the binding activity with PD-L1 or OX40 expressed HEK293 cells. FIGS. 8 and 9 show the binding activity of corresponding antibody leads as indicated by FACS with stable expressed PD-L1 or OX40 HEK293 cells.

FACS analysis of PD-L1 stable expression 293 cells stained with anti-PD-L1 antibody leads to examine the PD-L1 binding activity, stable expression cells were incubated with 1 μg/mL purified anti-PD-L1 antibody leads, reference antibody (Ref Ab MPDL3280A) or with isotype antibody as negative control on ice for 1 hr. The cells were washed three times with 1× PBS and then incubated with Alexa-488-conjugated goat anti-human IgG (H+L) (Invitrogen Inc.) on ice for additional 1 hr. After staining, the cells were washed three times with 1× PBS, resuspended in 1× PBS/2% FBS before analyzed by FACS Calibur (BD Biosciences, Inc.) and FlowJo (TreeStar, LLC). Same scenario, the binding activity of anti-OX40 antibody leads for stable expressed OX40 HEK293 cells in FIG. 9 were also executed with a similar strategy and analyzed as described above. As shown in the FIG. 8, most anti-PD-L1 antibody leads possess a good binding activity as well as reference antibody. This indicated the phage clones selected from the OmniMab library indeed recognize the native PD-L1 in the cells.

This phenomenon is also observed for anti-OX40 antibody leads as shown in the FIG. 9. FACS analysis of OX40 stable expression 293 cells clone 2D5 stained with purified anti-OX40 antibodies leads to examine the OX40 binding activity, stable expression cells were incubated with 2 μg/mL anti-OX40 reference Abs (OX40 ref.) or anti-CD137 reference Abs (CD137 ref.) as control antibody on ice for 1 hr. The cells were washed three times with 1× PBS and then incubated with Alexa-488-conjugated goat anti-human IgG (H+L) (Invitrogen Inc.) on ice for additional 1 hr. After staining, the cells were washed three times with 1× PBS, resuspended in 1× PBS/2% FBS before analyzed by FACS Calibur (BD Biosciences, Inc.) and FlowJo (TreeStar, LLC).

Ligand Competition Binding (ELISA Assay)

Antibody leads were exposed to the binding selectivity and affinity assay used to evaluate the anti-PD-L1 antibody leads of the present invention for their ability to block binding of PD-L1 to PD-1.

Figure 10:
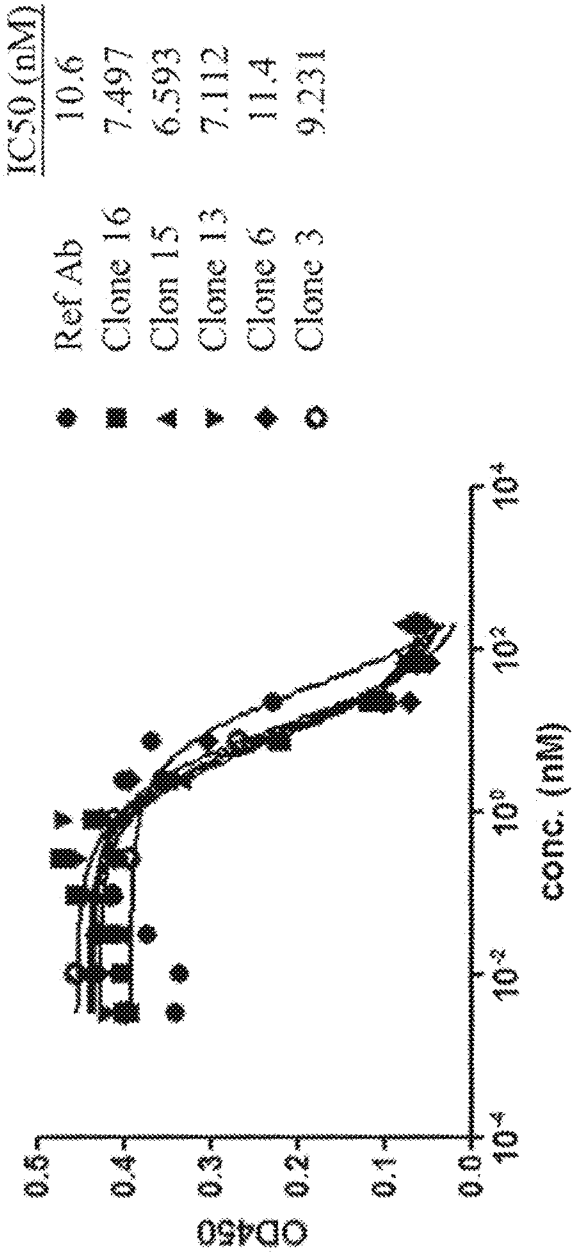
FIG. 10 shows the blockage of PD-1/PD-L1 interaction with purified anti-PD-L1 antibodies. Purified antibodies as indicated were applied with biotinylated-PD-L1-Fc and recombinant human PD-1/His (hPD-1/His) to evaluate the inhibition activity of PD-1/PD-L1 interaction. The binding recombinant PD-L1-Fc and hPD-1/His was detected by streptavidin-HRP and analysis by ELISA.

Antibodies were tested for their ability to block the binding of the human PD-L1-Fc chimera (PD-L1-Fc) to recombinant human PD-1/His (hPD-1/His) by ELISA. Purified recombinant hPD-1/His (APBio) was dialyzed to 1 mg/mL in PBS and then conjugated with biotin (Abcam). Nunc Maxisorp 96 well pate was coated with 250 ng hPD-1/His per well in PBS overnight. The hPD-1/His solution was removed and the plates were washed three times with 0.4 mL wash buffer (0.1% Tween-20 in PBS). 0.4 mL blocking buffer (5% low-fat milk powder in PBS) was added to all wells and incubated at room temperature for 1 hour with mixing. During the blocking step the antibody stocks were diluted in a range from 200 nM to 0 nM in PBS with 2 folds serial dilution. Purified recombinant biotinylated-PD-L1-Fc chimera was diluted to 4 μg/mL in PBS. The PD-1/His coated plates were washed three times with 0.2 mL wash buffer (0.1% Tween 20 in PBS). 60 μL antibody dilutions (anti-PD-L1 antibody leads or Ref Ab MPDL3280A) were added alone with 60 μL biotinylated-PD-L1-Fc chimera and incubated at room temperature for 1 hour. Plates were washed as described previously. Streptavidin-HRP was diluted 1:2000 in PBS, 100 μL of the resulting solution added to the wells of the washed plated, and incubated at room temperature for 1 hour. Plates were washed as previously described, 100 μL TMB substrate solution was added to each well and incubated for 10 minutes. The reaction was stopped with 50 μL 1N HCl and absorbance at 450 nm read using Bio-Tek reader and shown in FIG. 10. Partial antibody leads are shown to inhibit the interaction between PD-PD-L1 by competition ELISA. Most antibody leads revealed a similar blocking activity as comparing with reference antibody (Ref Ab MPDL3280A).

Enhanced Stimulation of T Cell Activation by Inhibition of PD-1:PD-L1 Ligand Interaction for Anti-PD-L1 Antibody The PD-1 signaling pathway inhibits moderate TCR/CD28 costimulatory signals, with cytokine production being reduced first without a decrease in T cell proliferation. As the TCR/CD28 costimulatory signals weaken, the PD-1 pathway dominates, with a great reduction in cytokine production accompanied by a reduction in proliferation. Accordingly in order to confirm that the inhibition of the PD-1 via inhibition of the interaction with PD-L1, human antibodies of the invention enhances T cell activation, mixed lymphocyte reactions (MLRs) are performed.

Monocytes from human whole blood were enriched by RosetteSep™ Human Monocyte Enrichment Cocktail (Cat. No. 15068) and cultured in differentiation medium, RPMI 1640 with 10% FBS, 100 ng/mL (1000 U/mL) GM-CSF, 100 ng/mL (500 U/mL) for 6 days. The differentiate dendritic cells (DC) from monocyte were checked by DC-SIGN-PE, anti-CD14 conjugated with FITC Ab, anti-CD83 conjugated with PE Ab, or anti-CD80 conjugated with FITC Ab to validate the differentiation and used to be APCs in MLRs.

Figures 11A, 11B:
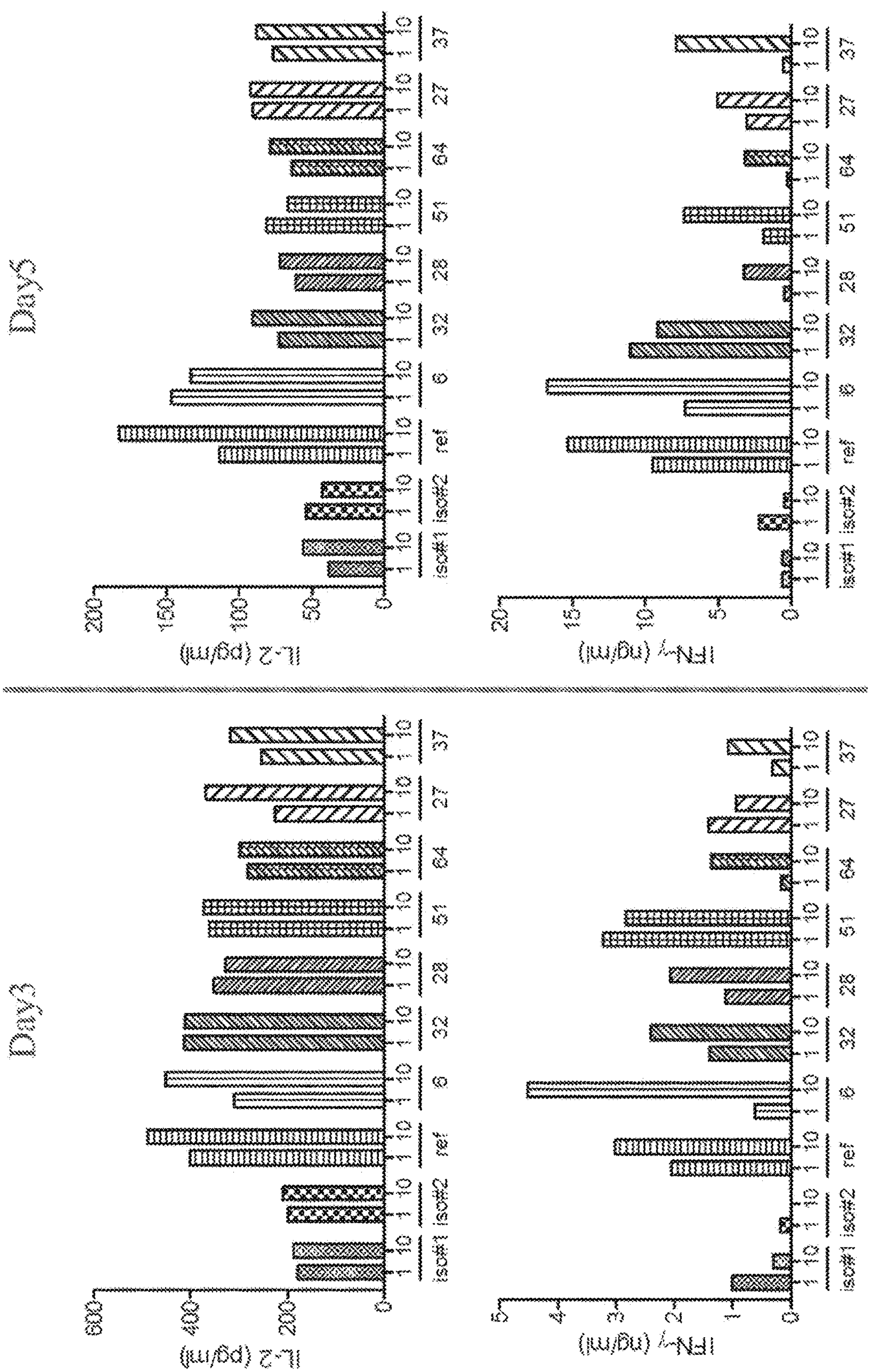
FIGS. 11A and 11B show anti-PD-L1 antibody leads with 1 or 10 μg/mL stimulates T-cell proliferation and induces IL-2 and/or IFN-γ production in a mixed lymphocyte reaction (MLR) assay after 3 days (FIG. 11A) or 5 days (FIG. 11B) antibody treatment.

Allogenic CD4+ T cells from human whole blood were isolated by RosetteSep™ Human CD4+ T Cell Enrichment Cocktail (Cat. NO. 15062). The purity of CD4+ T cells were checked with anti-CD4 conjugated APC Ab to make sure the purity is above 95% and then labeled with 1 uM CFSE (CellTrace™ CFSE cell proliferation kit, Life technologies, Cat. NO. C34554) for T cells proliferation assay. Labeled CD4+ T cells were used to co-culture with immature DC with different antibody leads as indicated for 3 and 5 days to see whether the antibody leads could restore the T cell activation through blocking the interaction between PD-1 and PD-L1. After 3 and 5 days incubation, the supernatant were collected for cytokine, such as IL-2 and IFN-γ quantitation by ELISA. The addition of anti-PD-L1 antibody leads (clones 6, 32, 28, 51, 64, 27, and 37) to cultures of immature dendritic cells plus allogeneic T cells is predicted to result in an increase in T cell proliferation and cytokine production, as compared to isotype IgG (iso #1, #2) treated cultures and shown in the FIGS. 11A and 11B. The IL-2 and IFN-γ production increase significantly in the MLRs as comparing with isotype antibody treatment after 3 days (FIG. 11A) or 5 days (FIG. 11B) antibody treatment, especially for anti-PD-L1 antibody clone 6. The cytokine increment is still obviously after 5 days antibody treatment and similar to reference antibody (ref), MPDL3280A. This indicated the anti-PD-L1 antibody clone 6 should be one of the potential leads for bispecific antibody composite.

Agonistic Activity Assay of Anti-OX40 Antibody

In order to activate OX40 costimulation of T-cell proliferation and cytokine production, the purified antibody leads were functionally screened for their ability to enhance cytokine production, proliferation, and to induce proliferation in human CD3+ T-cells. The anti-CD3 antibody (OKT3, BioLegend Cat. No. 317304) and anti-OX40 antibody leads (clones B6, B70, B120, A4, B17, B19, and B30), reference antibody (GSK3174998) or isotype antibodies (iso #1, #2) were coated in the Maxisorp 96-well plate. Meanwhile, naïve human CD3+T-cells were isolated from the human blood from heathy adult volunteers using a commercially available RosetteSep™ Human T Cell Enrichment Cocktail (STEMCELL Cat. No. 15061) as manufacture's described. The isolated CD3+ T cells were then labeled by CFSE (CellTrace™ CFSE cell proliferation kit, Life technologies, Cat. NO. C34554) and seeded as $1\times10^6$ cells/mL into the antibody pre-coated well containing RPMI 1640 medium, 10% fetal bovine serum and 2.5 mM L-glutamine to determine the cell proliferation and cytokine production. After 3 days culture, the cells were collected for proliferation assay by flow cytometry and medium were then analyzed for IL-2 and IFN-γ production by quantitation ELISA.

Figure 12A:
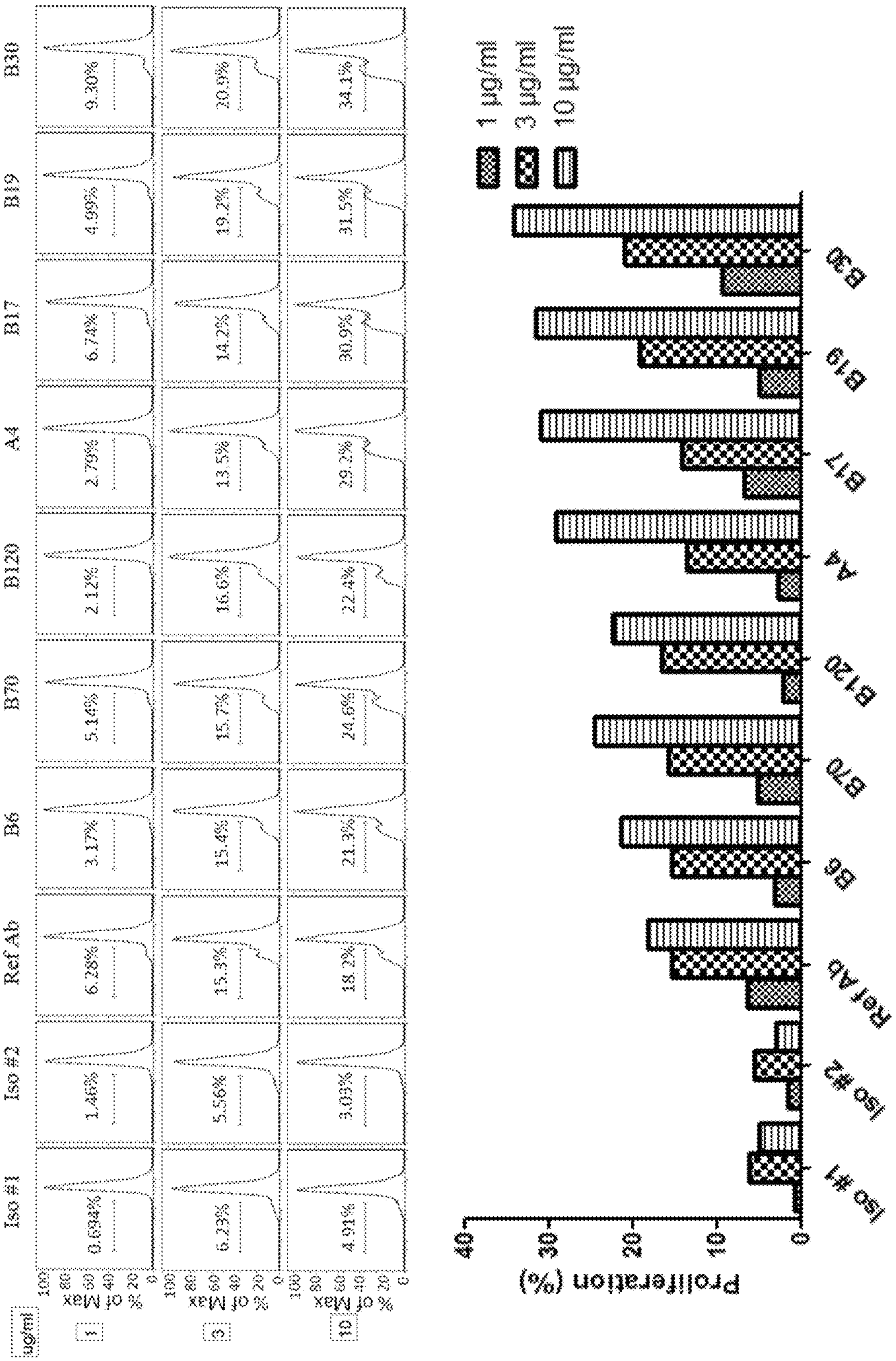
FIG. 12A shows the ability of anti-OX40 antibody leads to enhance the CD3+ T cell activation with dosage response as well as reference antibody.
Figure 12B:
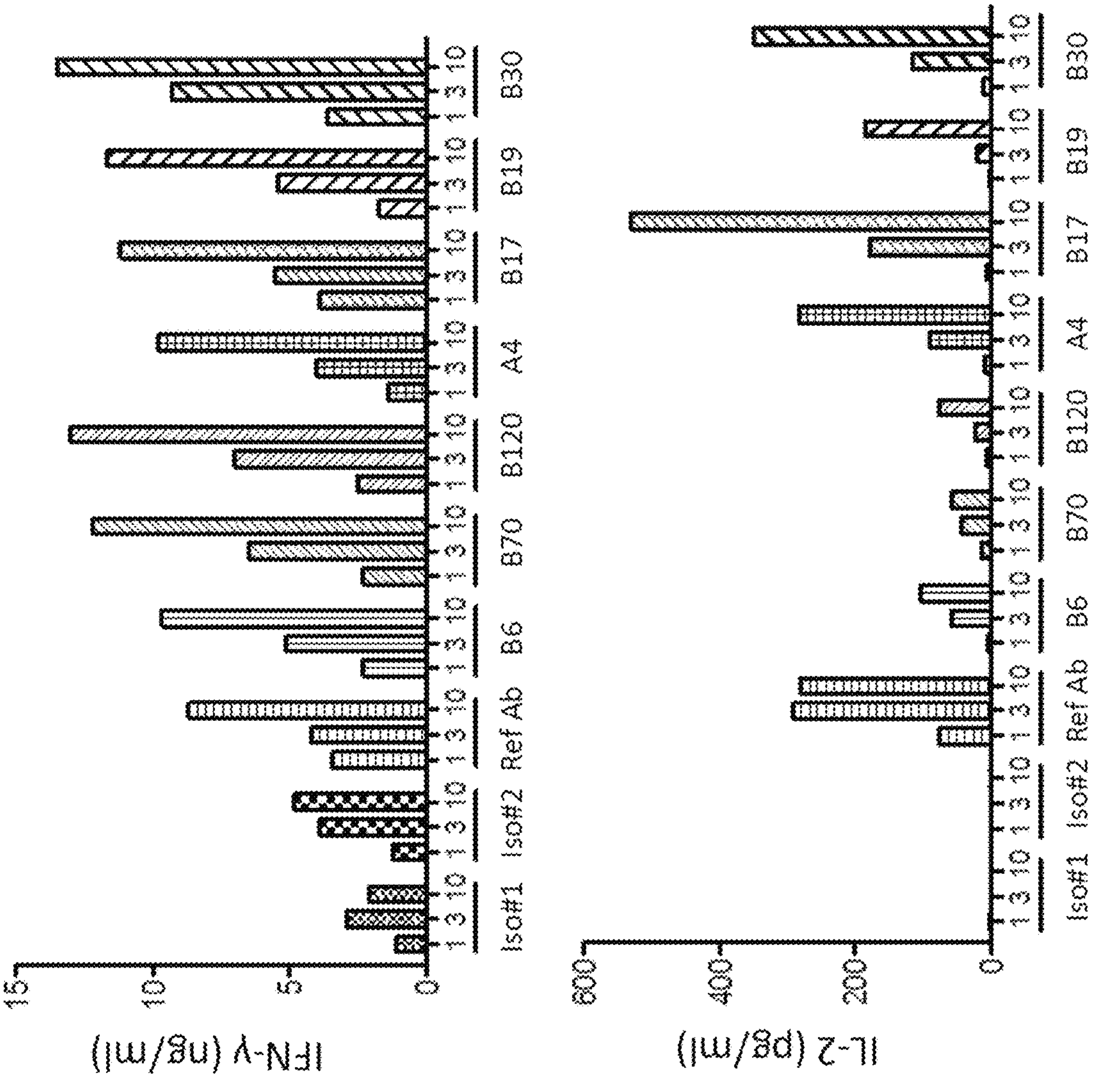
FIG. 12B shows the concentration of human IL-2 and IFN-γ present in cell culture media following 3 days of stimulation of human T cells with plate bound anti-CD3 and several concentrations of anti-OX40 antibody leads.

The screening of anti-OX40 antibody leads with agonistic activity in T cell activation was shown in the FIG. 12A. All anti-OX40 antibody leads showed the ability to enhance the CD3+ T cell activation with dosage response as well as reference antibody. Higher dosage antibody treatment showed obviously higher T cell activation activity. Meanwhile, cytokine production (FIG. 12B), such as IL-2 and IFN-γ also revealed similar T cell activation response, especially for anti-OX40 antibody lead clone B17. Cytokine is highly inducted after anti-OX40 antibody lead B17 3 days treatment. The enhancement is much higher than reference antibody treatment, this implicated clone B17 should be one of the candidates for bispecific antibody construction.

Figure 13A:
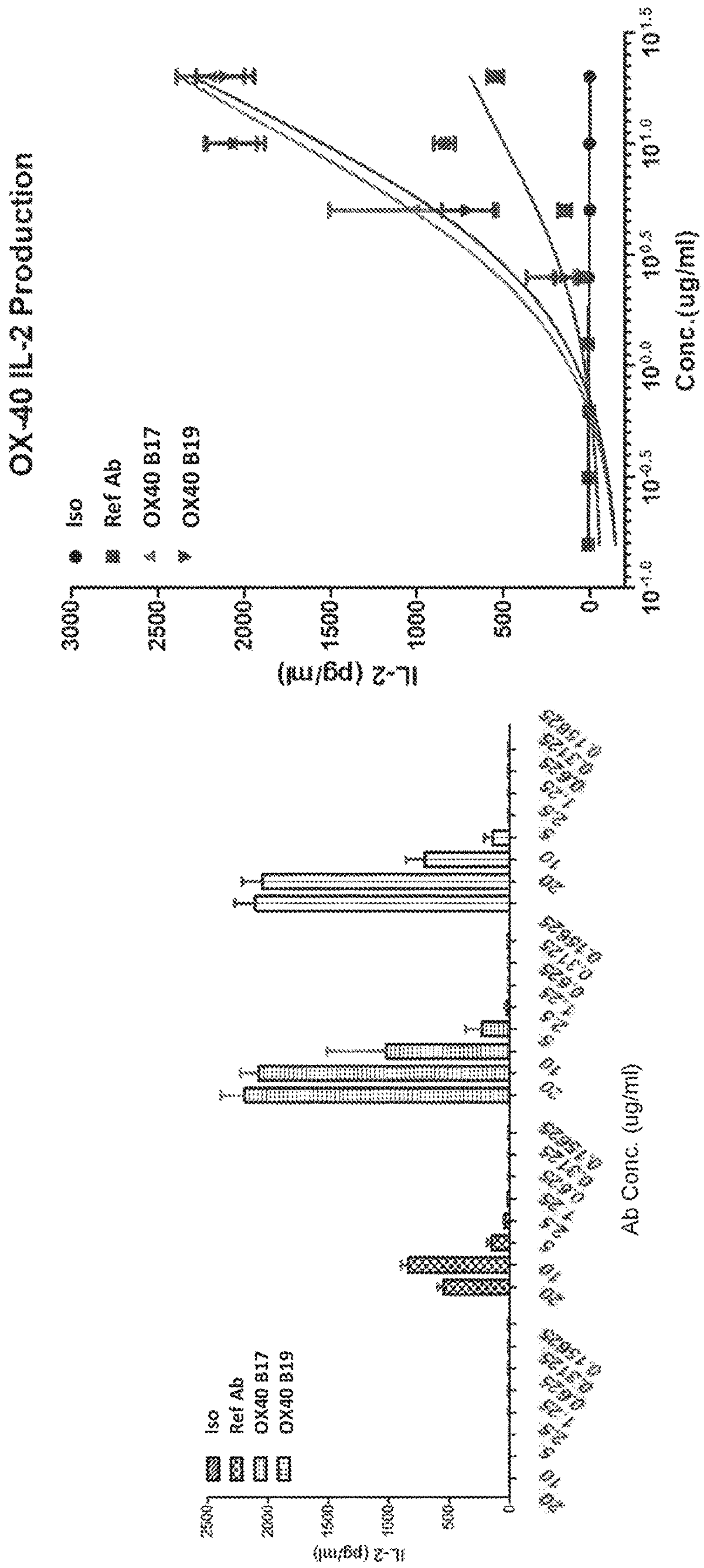
FIGS. 13A and 13B show the concentration of human IL-2 (FIG. 13A) and IFN-γ (FIG. 13B) present in cell culture media following 3 days of stimulation of human T cells with plate bound anti-CD3 and several concentrations of OX40 specific antibody leads.
Figure 13B:
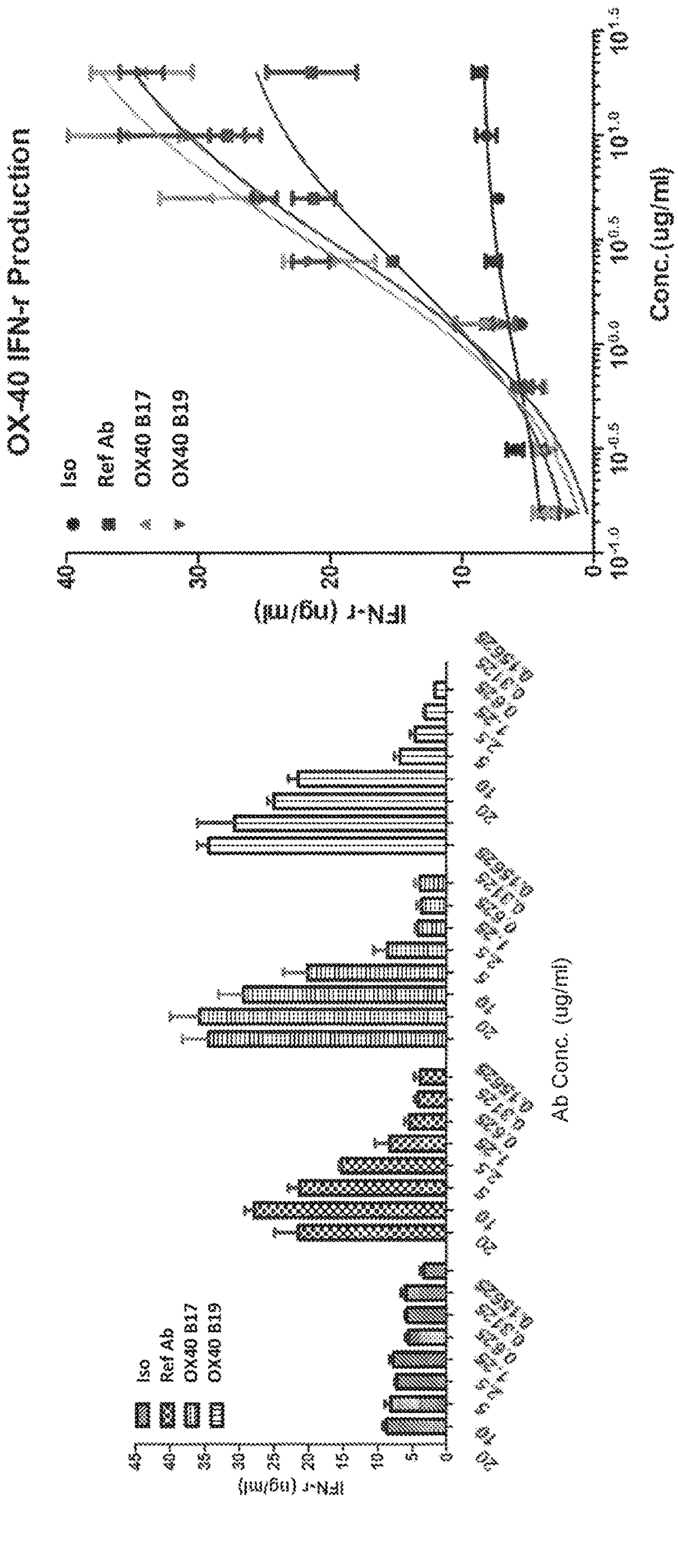

As the data shown in the FIGS. 13A and 13B, both anti-OX40 antibody leads, clones B17 and B19, were shown a better agonistic activity in the assay after anti-OX40 antibody leads (B17 or B19) 3 days treatment. Either IL-2 production or IFN-γ production shows an obvious enhancement upon antibody treatment and revealed does-dependent correlation. Higher cytokine productions were recorded in higher dose antibody treatment.

In order to evaluate the agonistic activity of OX40 antibody leads, B17 and B19, the EC50 were also determined as well as agonistic activity assay and cytokine production were recorded for comparison.

Construction, Expression and Purification of Anti-PD-L1-OX40 scFv Antibody

Figure 14:
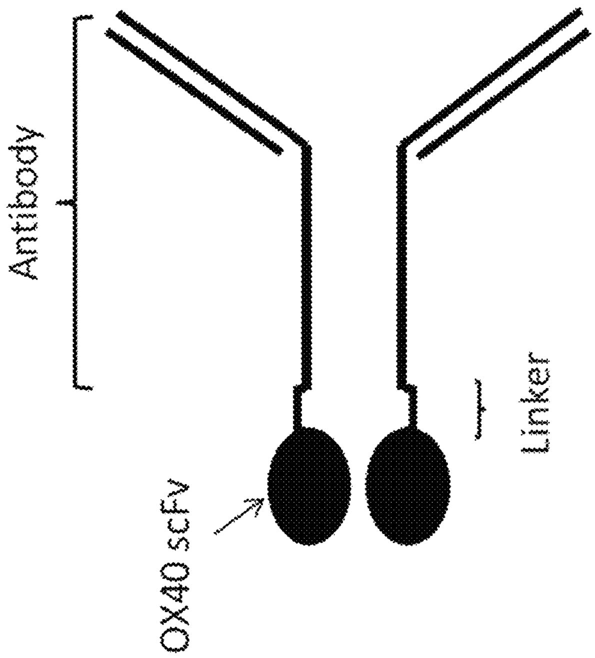
FIG. 14 shows the structure of an antibody heavy chain Fc fused with an OX40 specific scFv domain.

Since the bispecific is designed as IgG based fused with scFv format, the structure of anti-immune checkpoint antibody Fc-terminally fused with OX40 scFv. Antibody can be inhibitory anti-immune checkpoint antibodies, such as anti-PD-L1, anti-PD-1, anti-CTLA4, anti-LAG3, etc., or stimulatory antibodies, such as anti-CD28, anti-CD137, anti-CD27, anti-ICOS, etc. A linker is placed between antibody Fc and OX40 scFv to generate the bispecific antibody as depicted in FIG. 14.

Figure 15:
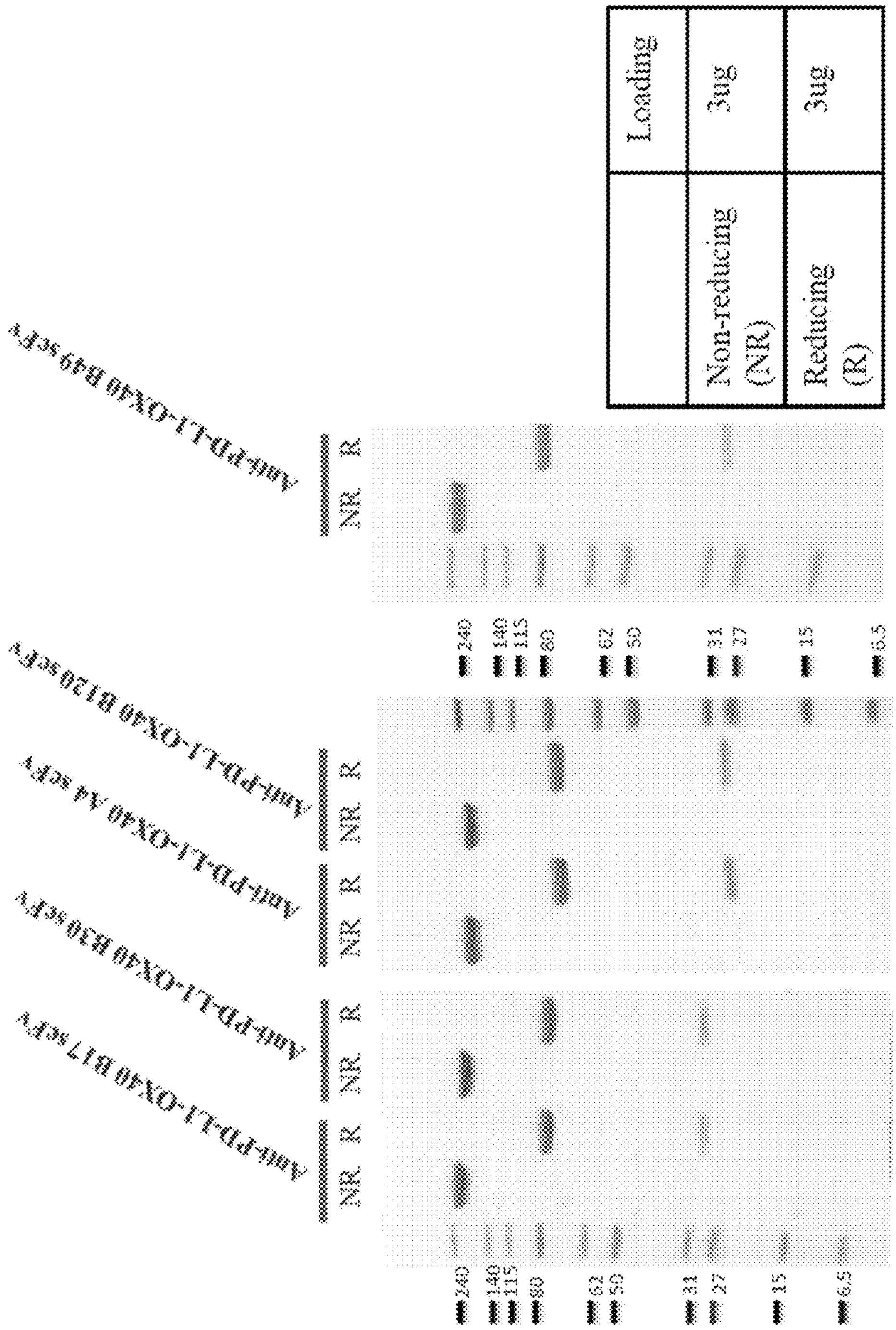
FIG. 15 shows examples of PAGE-gel analysis of anti-immune check point antibodies-human OX40 fusion proteins. Purified fusion proteins, anti-PD-L1-OX40 scFv fusion proteins were shown to have a molecular weight about 220 kDa (non-reducing), and heavy chain fusion has about 85 kDa and light chain is about 25 kDa (reduced) in both antibody fusions.

In some embodiment, the anti-PD-L1 antibody lead clone 6 is assigned to be IgG form, on the other hand, the anti-OX40 antibody lead would be transformed as scFv format to fuse at C-terminus of Fc region in anti-PD-L1 antibody lead clone 6. The transformation from antibody to scFv format could result in the reduction of the binding activity or specificity; therefore several anti-OX40 antibody leads were used to scFv transformation. Construction of bi-functional anti-PD-L1 antibody Fc fused with full-length OX40 scFv (SEQ ID NO: 10 as clone A4, SEQ ID NO: 11 as clone B17, SEQ ID NO: 12 as clone B19, or SEQ ID NO: 13 as clone B120). A short flexible peptide linker, $(GGGGS)_2$ (SEQ ID NO: 14) was placed between, for example, anti-PD-L1 antibody heavy chain C-terminus of Fc region and N-terminal module of OX40 scFv to ensure correct folding and minimize steric hindrance. The coding sequences of anti-PD-L1-OX40 scFv antibodies were shown in SEQ ID NO: 16 (anti-PD-L1-clone 6 heavy chain-OX40 clone B17 scFv) and NO. 17 (anti-PD-L1-clone 6 heavy chain-OX40 clone B19 scFv). The constructed antibody Fc fusion proteins were leaded by a signal peptide (SEQ ID NO: 15) and expressed by mammalian cells, and purified from the transfected cell culture supernatant via 1-step Protein G chromatography. As shown in FIG. 15, greater than 90% purity can be obtained in a single step purification process and shows that purified fusion proteins have correct molecular weight (Mw=220 kD).

Figure 16A:
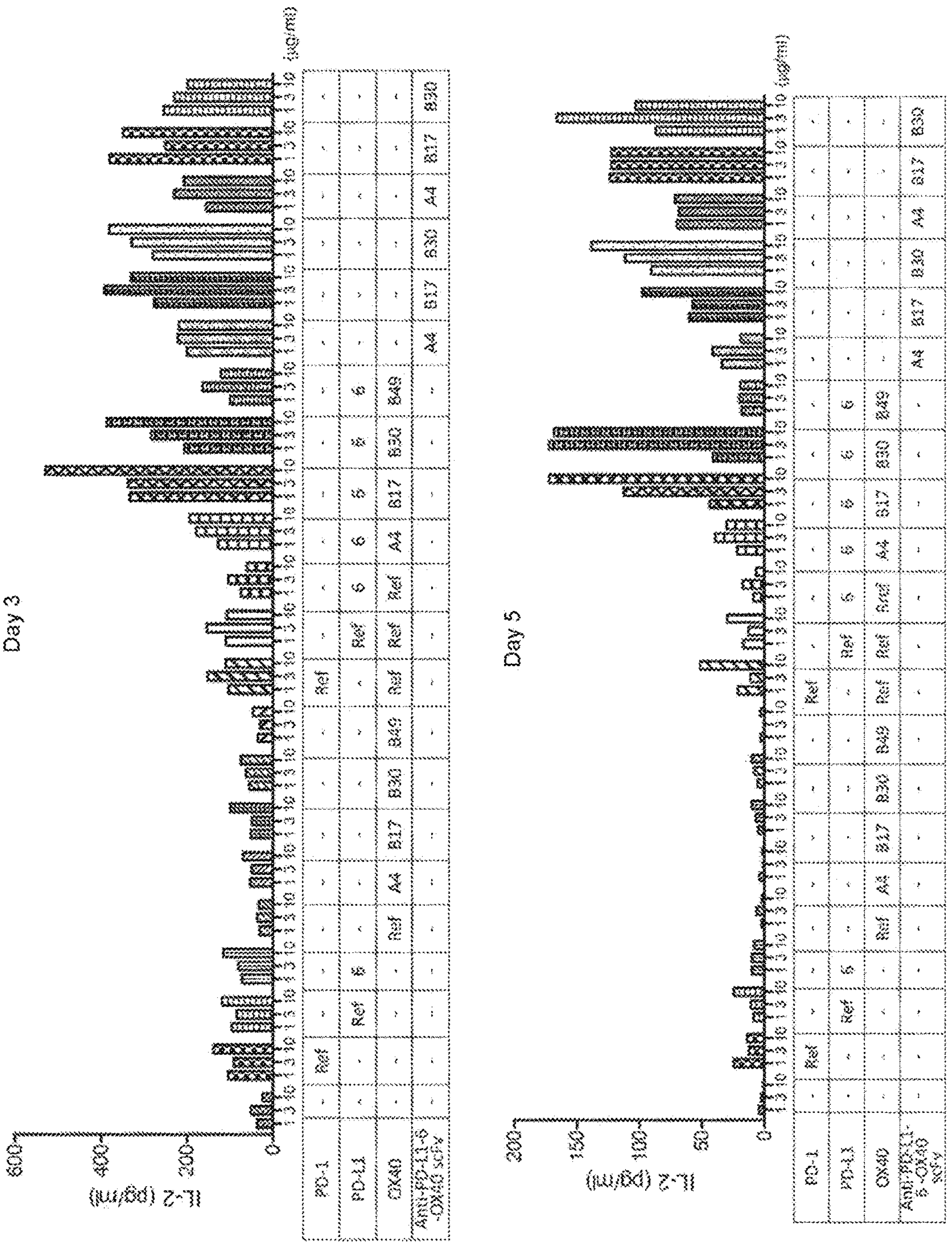
FIGS. 16A and 16B show bispecific antibody synergic stimulates T-cell activation for IL-2 and IFN-γ production in a mixed lymphocyte reaction (MLR) assay after 3 days (FIG. 16A) or 5 days (FIG. 16B) with mono-, combined or anti-PD-L1-OX40 scFv bispecific antibody treatment.
Figure 16B:
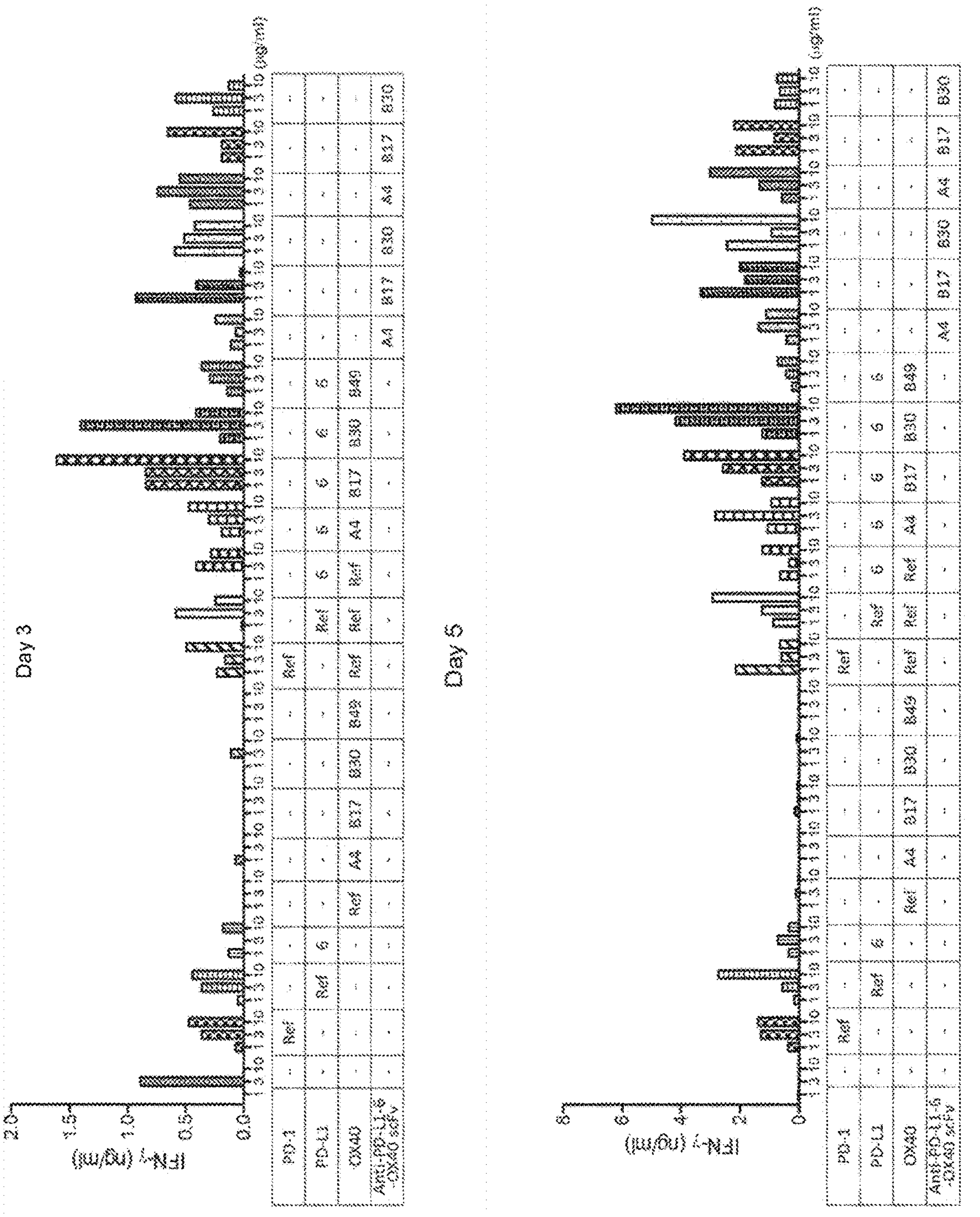

Enhanced Stimulation of T Cell Activation for Anti-PD-L1-OX40 scFv Bispecific Antibody Leads in MLRs To determine the synergic cooperation of bispecific antibody in enhancing T cells activation through inhibition the interaction between PD-1 and PD-L1 and agonistic activation of OX40 signaling, the bispecific antibody leads, anti-PD-L1-OX40 scFv, were applied into MLRs as described above. IL-2 and IFN-γ production were then recorded after 3 or 5 days antibody treatment. Mono-, combination or bispecific antibody was applied as equal amount or equal mole to compare the synergic effect in T cell activation enhancement and isotype IgG was used a negative control. As the data shown in the FIGS. 16A and 16B, the anti-PD-L1 antibody leads alone showed a significant IL-2 induction after 3 days treatment as well as reference antibody, MPDL3280A, on the contrary, the anti-OX40 antibody leads is unable to increase obviously upregulation of cytokine production, either after 3 days or 5 days antibody treatment. This is consisted with reference antibody, GSK3174998. However, combination of the anti-OX40 antibodies and anti-PD-L1 antibodies showed a significant upregulation of cytokine production after 3 and 5 days antibody treatment. The synergic effect is also observed in the bispecific antibody leads treatment and increment of cytokine production is similar as well as combination treatment. This indicated the anti-PD-L1-OX40 scFv bispecific antibody leads also function as well as antibody combination treatment without loss any binding activities in the scFv transformation.

Aggregation and Purity Determination of Bi-Specific Antibody

Since purified anti-PD-L1-clone 6-OX40 clone B17 scFv Ab revealed a lower purity (74.07%) by SEC-HPLC analysis after a single column protein A chromatography purification, therefore, several antibody variants were generated to improve the purity and reduce the aggregation for the bispecific antibody in the present invention. The linkers described as above were used to replace the linker in OX40 B17 scFv in the bispecific antibody, anti-PD-L1-OX40 Ab (SEQ ID NO: 16), and produced as anti-PD-L1-OX40 Ab-V1 to V4 (SEQ ID NO: 18 to SEQ ID NO: 21) in the CHO cells. Those variants were then purified and analyzed by XBridge Protein BEH SEC-HPLC column (Waters, Cat. No. 186007640). The data was summarized as below Table 1, one of the bispecific antibody variants, anti-PD-L1-OX40 Ab-V4 revealed a significant improvement of antibody purity. The purity is enhanced from 74.07 to 92.27%. Therefore, the anti-PD-L1-OX40 Ab-V4 was used to engineer further to improve the antibody purity.

TABLE 1

Different linkers in OX40 B17 scFv

| Abbreviation | Heavy chain/ light chain | Linker in OX40 B17 scFv | Reference |
|---|---|---|---|
| Anti-PD-L1-OX40 Ab | Anti-PD-L1-6-OX40 B17 scFv-L1 HC/Anti-PD-L1 6 LC | GGGGSGGGGSGGGGS (SEQ ID NO: 39) | Int. J. Mol. Sci. 2014, 15(12), 23658-23671 |
| Anti-PD-L1-OX40 Ab-V1 | Anti-PD-L1-6-OX40 B17 scFv-L2 HC/Anti-PD-L1 6 LC | SSGGGGSGGGGGGSSRSSL (SEQ ID NO: 40) | None |
| Anti-PD-L1-OX40 Ab-V2 | Anti-PD-L1-6-OX40 B17 scFv-L3 HC/Anti-PD-L1 6 LC | GGKGSGGKGTGGKGSGGKGS (SEQ ID NO: 41) | Viral J. 2008; 5:21 |
| Anti-PD-L1-OX40 Ab-V3 | Anti-PD-L1-6-OX40 B17 scFv-L4 HC/Anti-PD-L1 6 LC | GSASAPTLFPLVS (SEQ ID NO: 42) | DOI: 10.3892/mmr.2013.1502 |
| Anti-PD-L1-OX40 Ab-V4 | Anti-PD-L1-6-OX40 B17 scFv-L5 HC/Anti-PD-L1 6 LC | GSTSGSGKPGSGEGSTKG (SEQ ID NO: 43) | PMID: 8309948 |

For characterization the size distribution of bi-specific antibodies, samples were loaded onto XBridge Protein BEH SEC-HPLC column (Waters, Cat. No. 186007640) using a Waters Alliance 2695 Separations Module. Protein peak were detected at 280 nm using a Water 2996 PDA Detector. The mobile phase was isocratic 25 mM sodium phosphate (Sigma, Cat. No. 04272 and Cat. No. 04269) with 200 mM NaCl (AMRESCO, Cat. No. 0241), pH 6.8, at a flow rate of 0.4 mL/min. Peak percentages were determined by the portions of peak area as shown in FIGS. 17A to 17E.

Figure 17A:
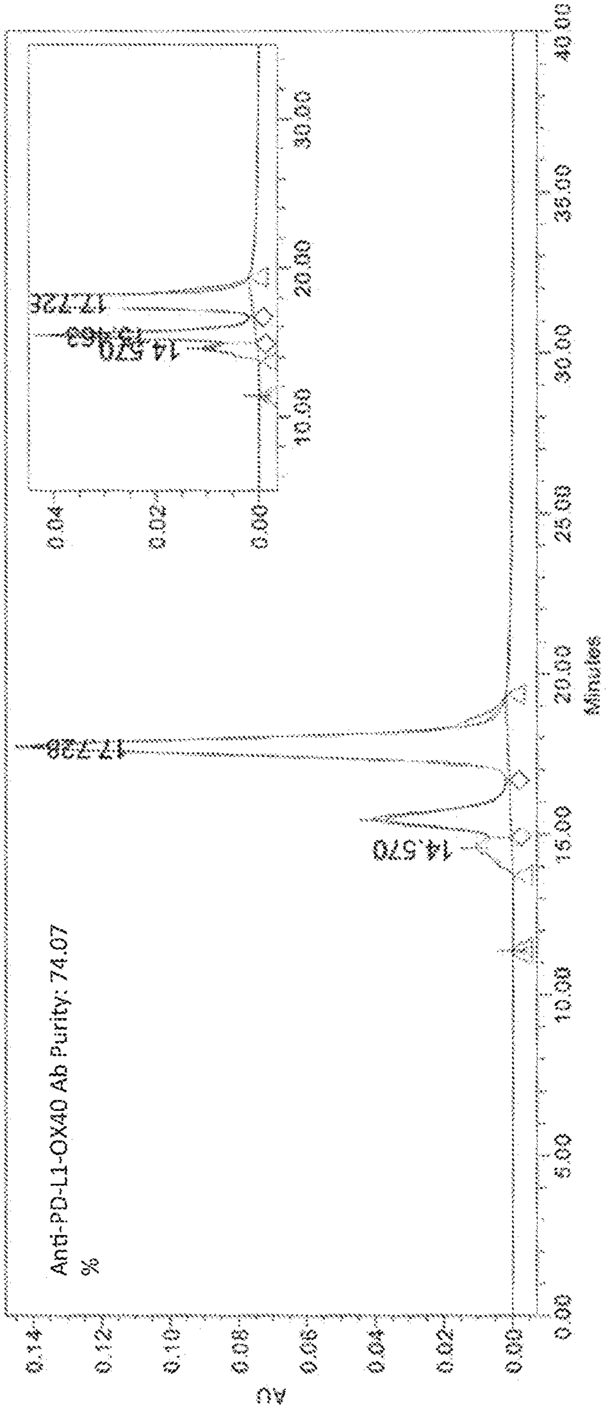
FIGS. 17A to 17E respectively show the aggregation and purity determination of Bi-specific antibodies, Anti-PD-L1-OX40 Ab and Anti-PD-L1-OX40 Ab-V1 to V4, with 5 different linkers in OX40 scFv.
Figure 17B:
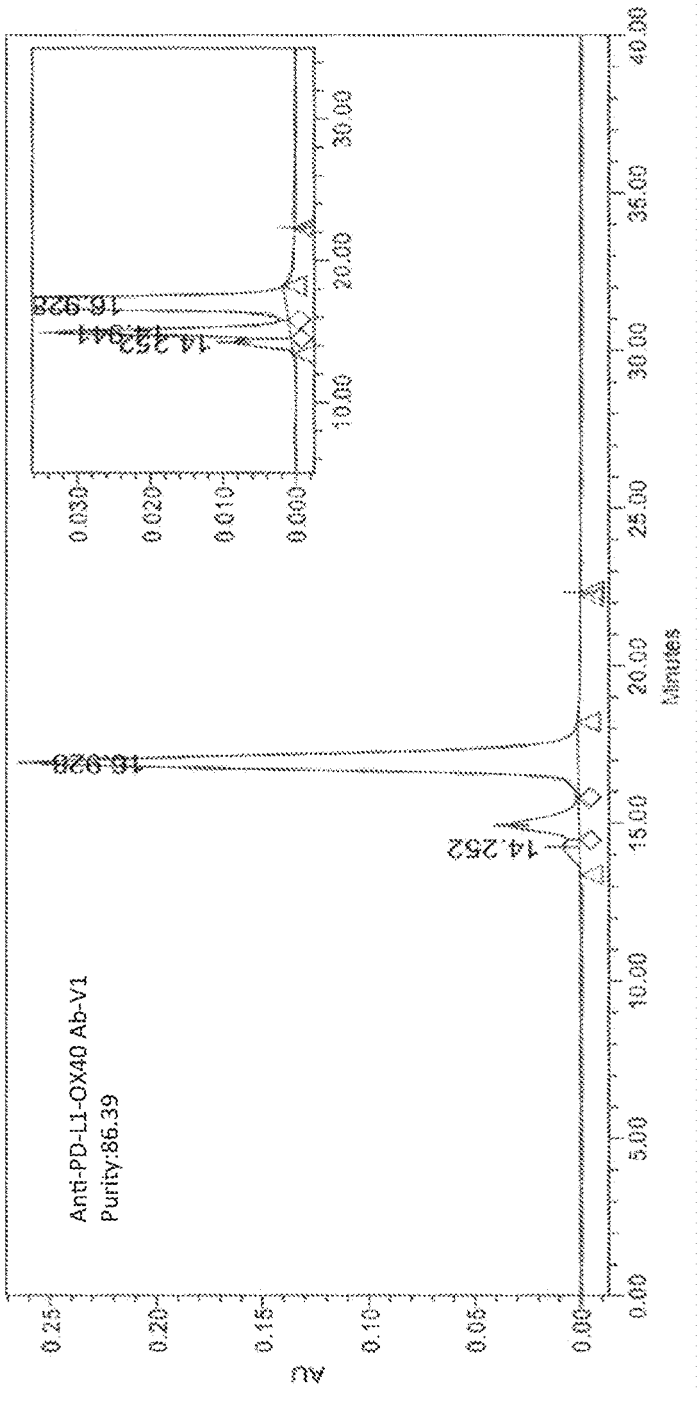
Figure 17C:
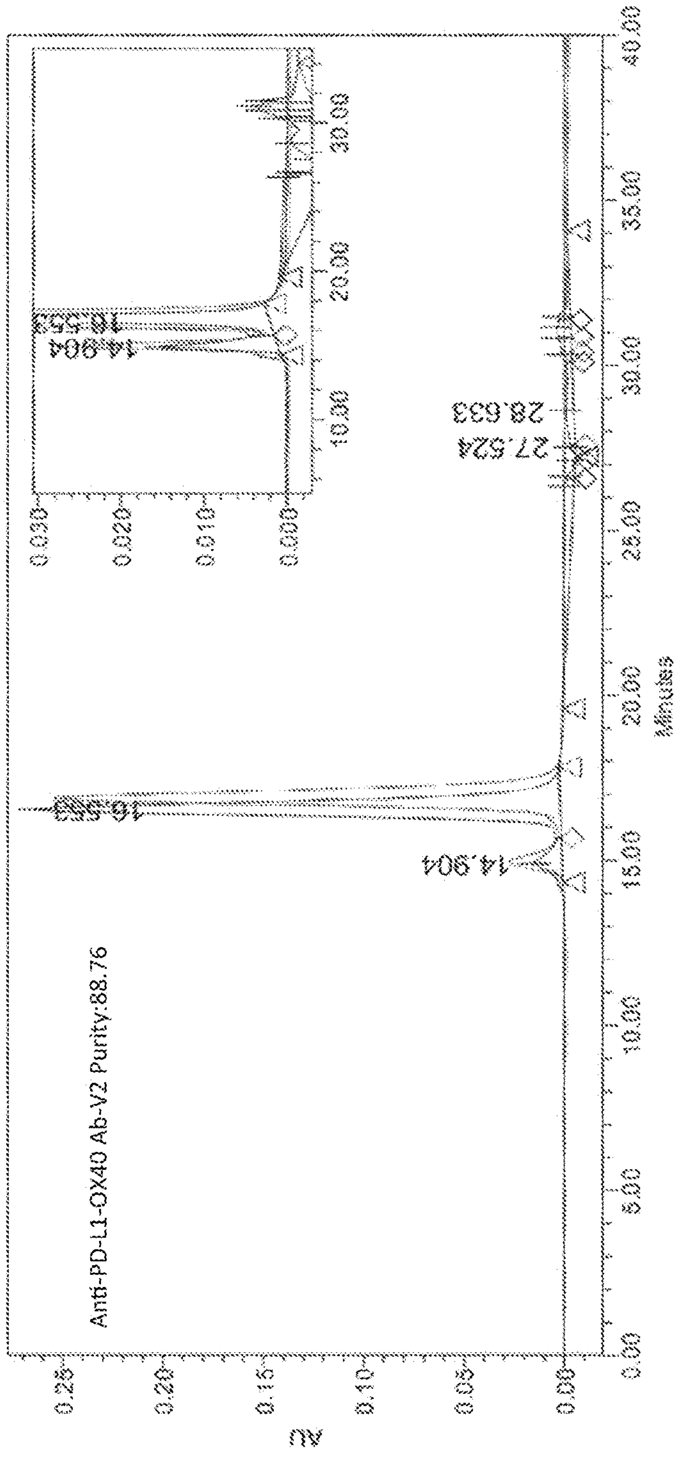
Figure 17D:
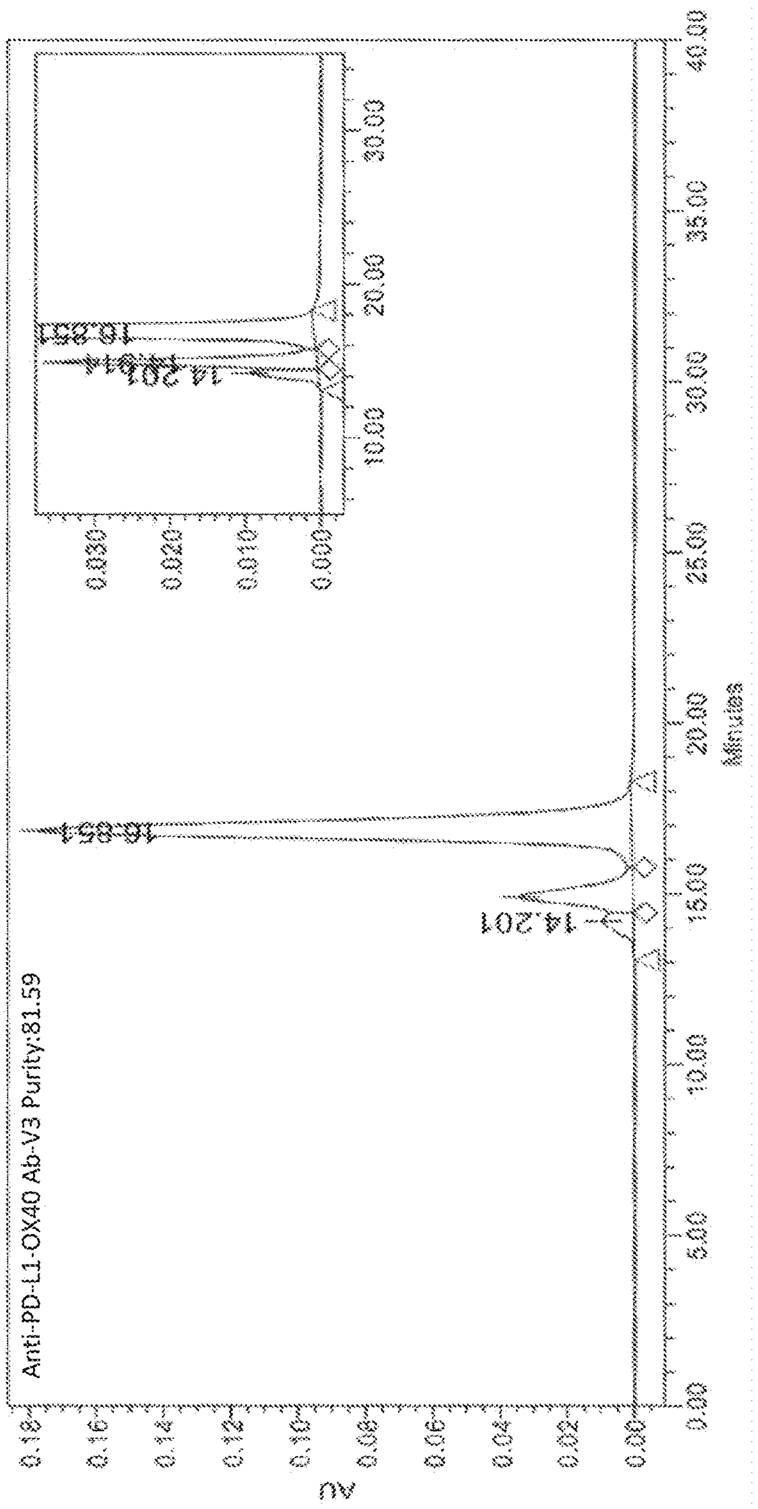
Figure 17E:
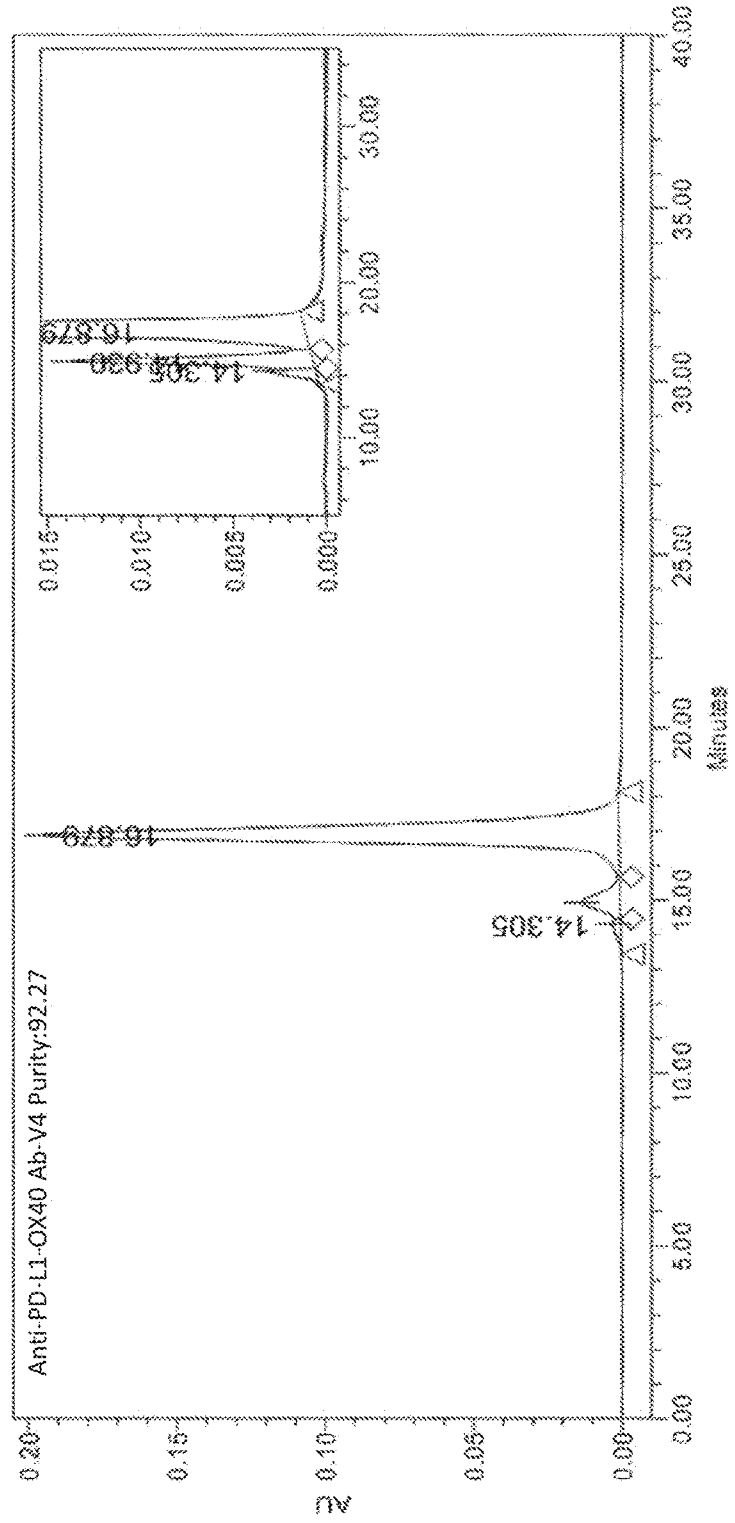
Figure 18:
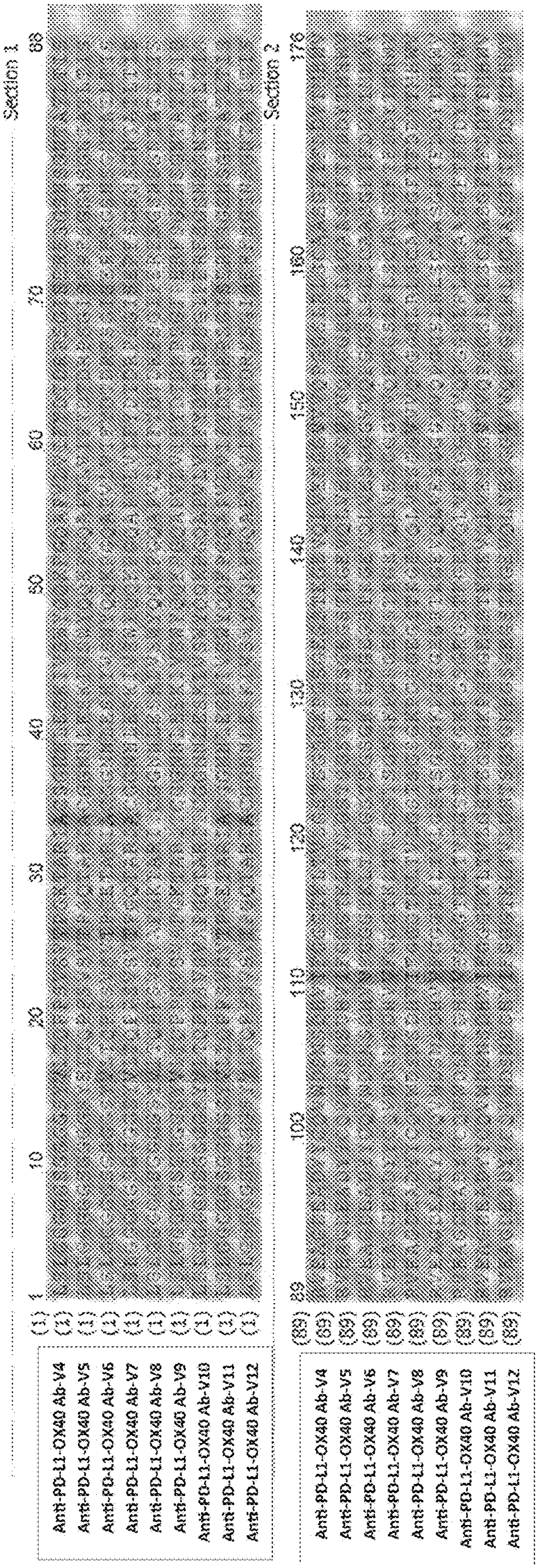
FIG. 18 shows sequence variants among OX40 clone B17 scFv of Anti-PD-L1-OX40 Ab-V4 to V12 (SEQ ID NOS: 30-38).
Figure 19:
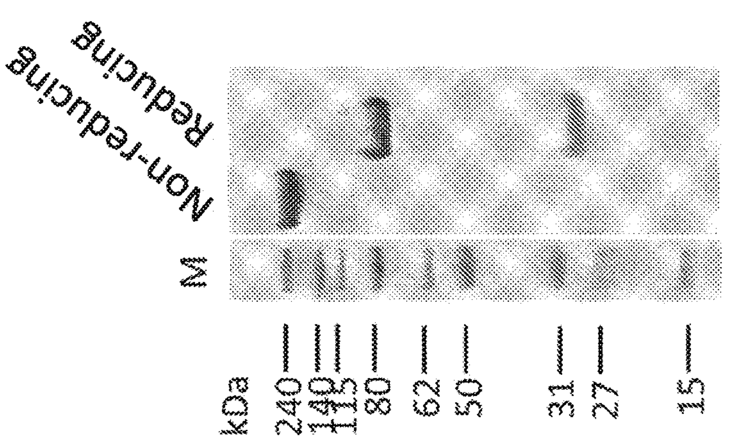
FIG. 19 shows examples of PAGE-gel analysis of anti-immune check point antibodies-human OX40 fusion proteins. Purified fusion proteins, anti-PD-L1-OX40 Ab-V5 fusion proteins were shown to have a molecular weight about 220 kDa (non-reducing), and heavy chain fusion has about 80 kDa and light chain is about 30 kDa (reduced) in both antibody fusions.

Anti-PD-L1-OX40 Ab-V4 revealed a significant purity improvement (FIG. 17E). The bispecific antibody was engineered further in the OX40 B17 scFv fragment to improve purity again. Several residues in the OX40 B17 scFv showed in FIG. 18 were substituted with difference amino acid and heavy chain variants were pairing with anti-PD-L1 clone 6 light chain to generate several bispecific antibody variants, from anti-PD-L1-OX40 Ab-V5 to V12 (SEQ ID NO: 22 to SEQ ID NO: 29), and then expressed and purified as mentioned above. The purity of bispecific antibody variants were summarized as below Table 2, the anti-PD-L1-OX40 scFv-V5 revealed the best purity in those antibody variants. The purity is aroused up to 96.46%. This is shown a superior purity for the engineered bispecific antibody and also revealed a good development ability for this bispecific antibody in the future. As shown in FIG. 19, the integrity of anti-PD-L1-OX40 Ab-V5 was also analyzed by SDS-PAGE and shown a good integrity under reducing and non-reducing condition.

TABLE 2

Purity of Antibody

| Antibody | Purity by SEC-HPLC (%) |
|---|---|
| Anti-PD-L1-OX40 Ab-V4 | 92.27 |
| Anti-PD-L1-OX40 Ab-V5 | 96.46 |
| Anti-PD-L1-OX40 Ab-V6 | 86.36 |
| Anti-PD-L1-OX40 Ab-V7 | 88.04 |
| Anti-PD-L1-OX40 Ab-V8 | 90.00 |
| Anti-PD-L1-OX40 Ab-V9 | 87.89 |
| Anti-PD-L1-OX40 Ab-V10 | 86.56 |
| Anti-PD-L1-OX40 Ab-V11 | 86.61 |
| Anti-PD-L1-OX40 Ab-V12 | 84.78 |

Figure 20:
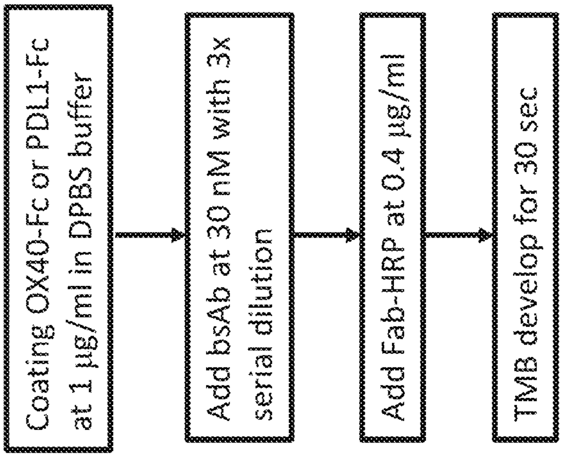
FIG. 20 shows a flow chart illustrating the ELISA method for binding activity evaluation of bispecific antibody variants.
Figure 21:
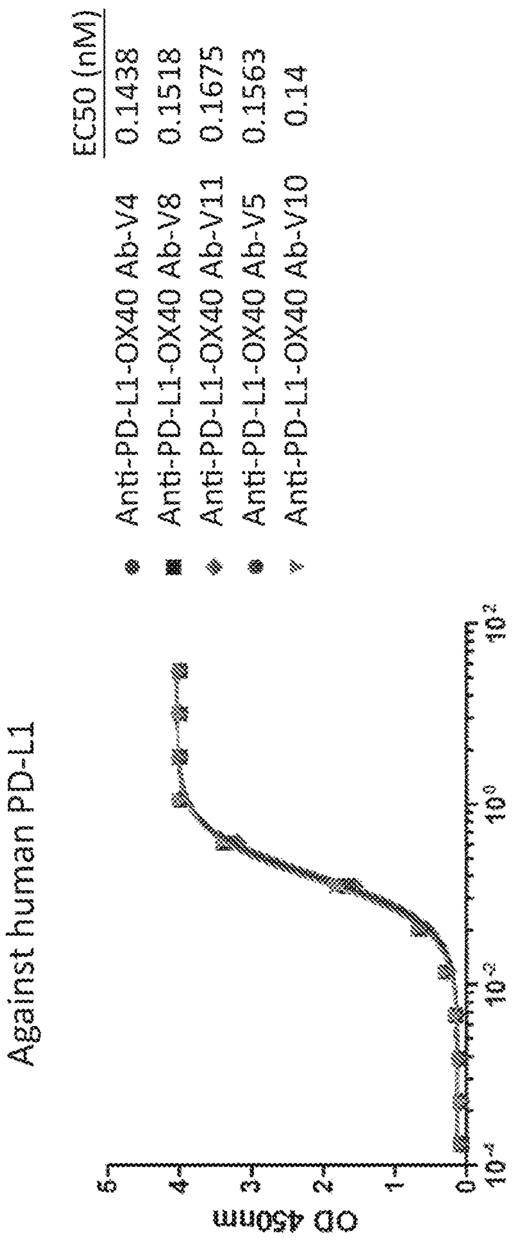
FIG. 21 shows the human PD-L1 binding activity of the bispecific antibody variants and its EC50.
Figure 22:
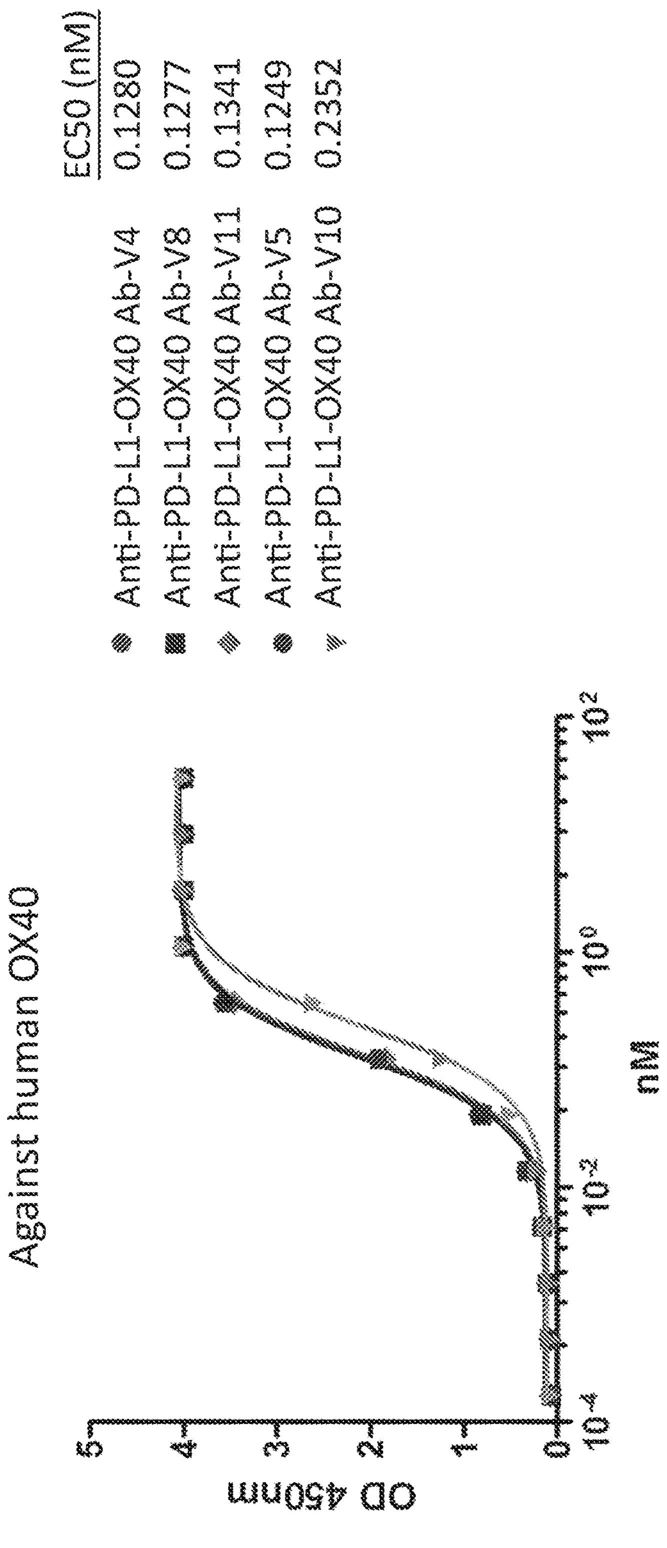
FIG. 22 shows the human OX40 binding activity of the bispecific antibody variants and its EC50.

Meanwhile, the engineered bispecific antibody variants were also applied for binding activity evaluation for human PD-L1 and OX40 by direct ELISA as shown in FIG. 20. All bispecific antibody variants as indicated showed the same binding activity for human PD-L1 (FIG. 21), this binding activity is similar with anti-PD-L1 6 antibody. This phenomenon was also observed in the human OX40 binding assay (FIG. 22). Only anti-PD-L1-OX40 Ab-V10 showed a weaker binding activity for human OX40 as comparing with other variants. It indicated the engineering of OX40 scFv is not affected the OX40 binding activity. The binding activity is retained either for PD-L1 or OX40. Since the anti-PD-L1-OX40 Ab-V5 revealed a superior antibody purity and binding activity for PD-L1 and OX40, so the anti-PD-L1-OX40 Ab-V5 was chosen for serum stability.

Ex Vivo Serum Stability

The stability was assessed in human serum (BioreclamationIVT, Cat. No.HMSRM) as well as serum from relevant preclinical species: rhesus monkey (BioreclamationIVT, Cat. No.RHSSRM), and CD1 mouse (BioreclamationIVT, Cat. No.MSESRM). Samples were added into different species serum for a final concentration of 15 μg/mL and incubated at 37° C. water bath. Serum samples were collected after incubation times of 0, 1, 2, 3, 7, 10 and 14 day and stored frozen at −80° C. until analysis.

Quantitation Sandwich ELISA

OX40-Fc was coated into ELISA plate (NUNC, Cat. No. 442404) with 100 μL at 1 μg/mL in PBS and incubated for overnight at 4° C. Wash buffer was prepared as PBS with 0.1% Tween-20 (Sigma, Cat. No.P2287-500 mL) and blocking buffer was prepared as 1% BSA (UniRegion, Cat. No.UR-BSA001-100G) in wash buffer. Serum samples were prepared with 10-fold dilution with 3× serial dilution in blocking buffer and the standards were prepared at 10 nM with 3× serial dilution in blocking buffer. Biotinylated PD-L1-Fc was labeled with Biotin Fast conjugation Kit (abcam, Cat. No.ab201796) using standard protocol and prepared at 30 nM in blocking buffer. Streptavidin-HRP (abcam, Cat. No.ab7403) was prepared at 1 μg/mL in blocking buffer. All the samples were added into each well for 100 μL after plates washed 3 times with wash buffer and incubated for 1 hour at ambient temperature. TMB development with 100 μL TMB solution (Invitrogen, Cat. No. 00-2023) for 2 min and stopped with 100 μL 1N HCl solution (Merck, Cat. No. 1.00317.1000). O.D. 450 nm absorption was read by ELISA reader (Biotek, Powerwave XS).

Figure 23:
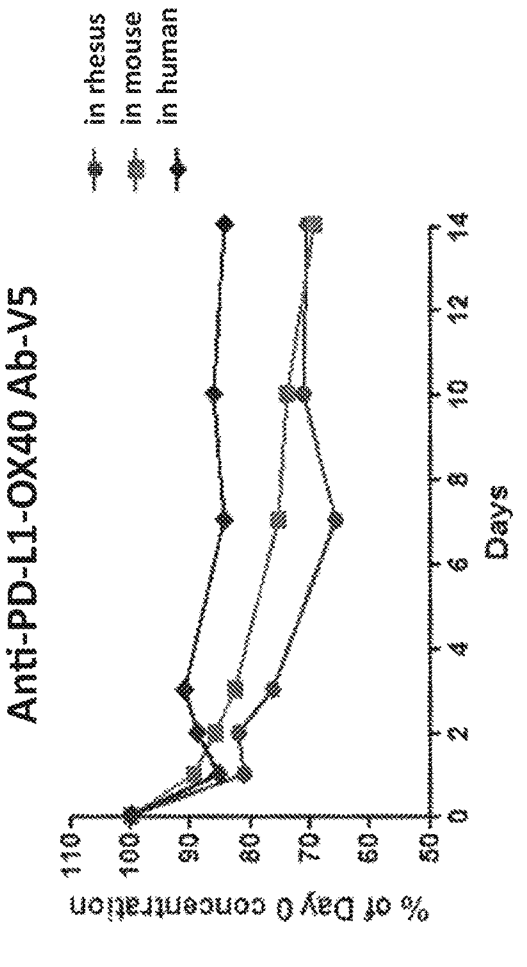
FIG. 23 shows the ex vivo serum stability of bispecific antibody variant, anti-PD-L1-OX40 Ab-V5.

Anti-PD-L1-OX40 Ab-V5 was chosen for ex vivo serum stability because of its superior purity and binding activity for PD-L1 and OX40. The purified bispecific antibodies were mixed with serum from different species, such as human, mouse or monkey. After several days culture, the samples were took and analyzed by sandwich ELISA to determine the antibody amount. As shown in FIG. 23, the anti-PD-L1-OX40 Ab-V5 still showed a good serum stability after 14 days culture at 37° C. The concentration of the antibody is still above 70% either in human, mouse or monkey. It is indicated the antibody also have a good serum stability.

Figure 24A:
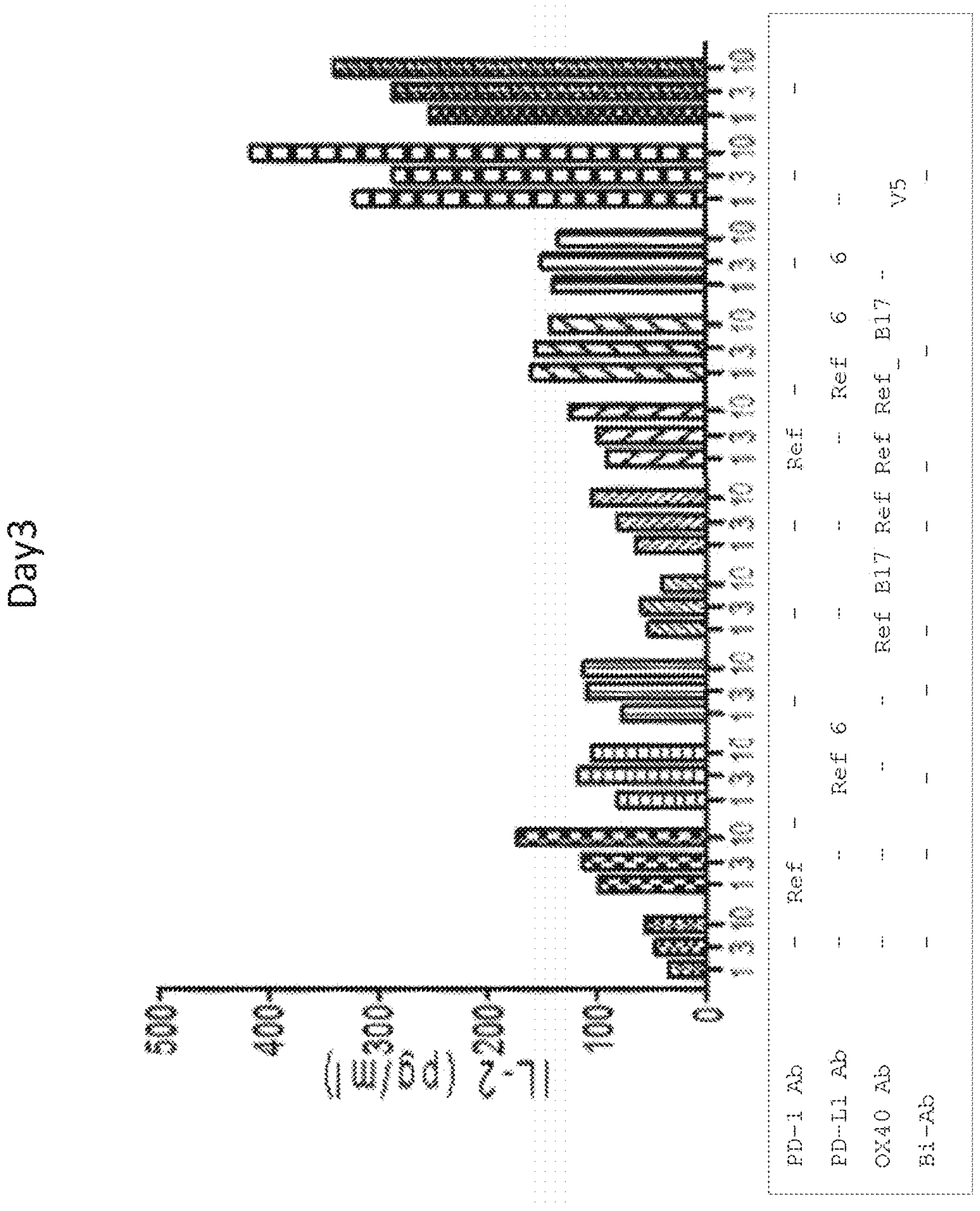
FIGS. 24A and 24B show the IL-2 production for 3 days (FIG. 24A) and IFN-γ production for 5 days (FIG. 24B) after modulating T cell with mono-, combined or anti-PD-L1-OX40 Ab-V5 bispecific antibody treatment.
Figure 24B:
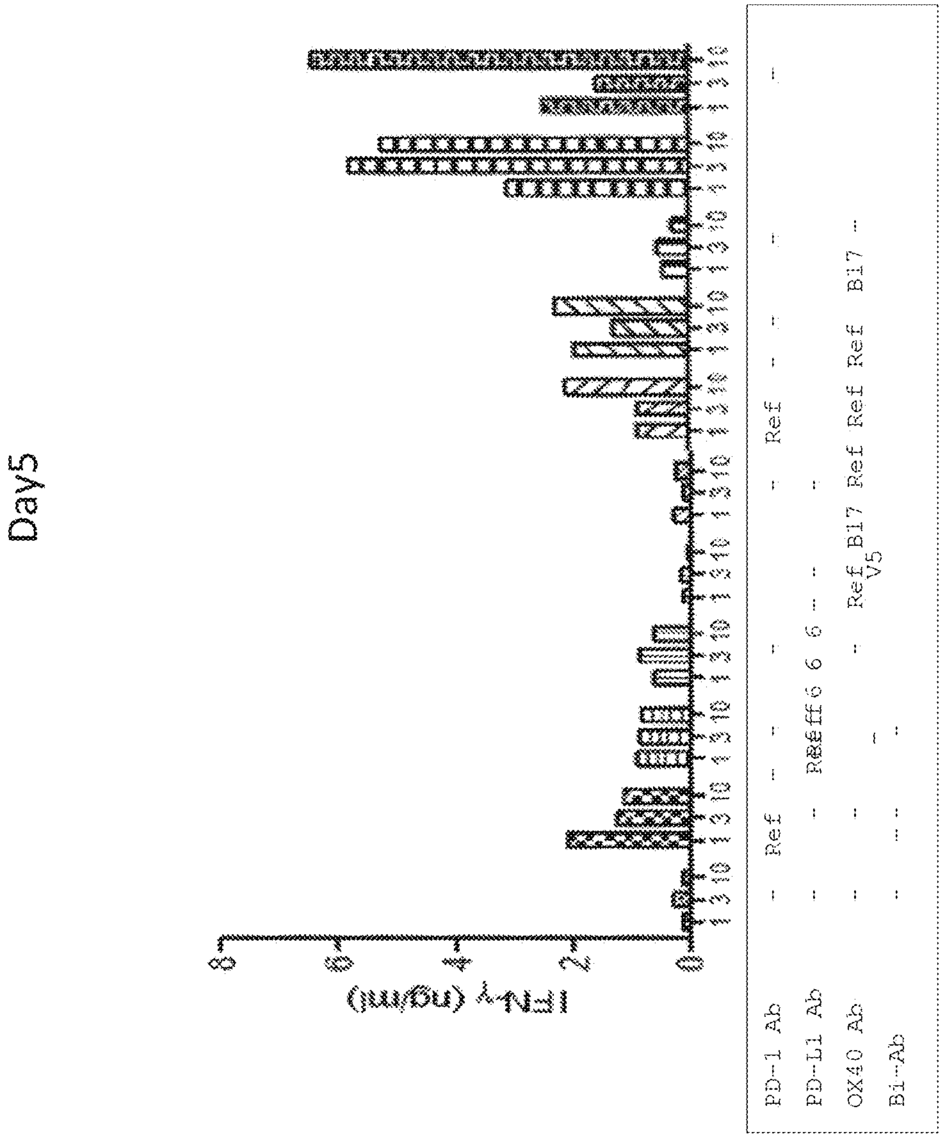

To measure the ability of the anti-PD-L1-OX40 Ab-V5 to modulate T cell responsiveness purified T cells will be cultured with allogeneic dendritic cells, prepared by culturing monocytes in GM-CSF and IL-4 for few days. Parallel plates were set up to allow collection of supernatants at day 3 and day 5 to measure IL-2 and IFN-γ respectively using a commercial ELISA kit. As the data shown in FIGS. 24A and 24B, the IL-2 and IFN-γ production are highly upregulated in the bispecific antibody treatment (V5) as well as combination treatment after 3 or 5 days antibody treatment. Also, the enhancement is obviously superior than the anti-PD-L1 Ab or anti-OX40 Ab treatment alone. This implicated the engineered bispecific antibody, V5, still possess the agonistic activity as well as combination treatment without functionality lost and could be developed as a therapeutic antibody for various solid tumor or cancer in the future.

Anti-Tumor Activity of Bispecific Antibody (In Vivo Model)

The lack of rodent cross reactivity of the PD-L1 and OX40 in bispecific antibodies prevented the use of standard murine syngeneic or human xenograft tumor models for the assessment of anti-human tumor efficacy of the antibodies. Accordingly, a novel huPBL-SCID-Bg xenogeneic tumor mouse model was generated using a SCID-Bg mouse (CB.17/Icr.Cg $Pkrdc^{scid}Lyst^{bg}$/Crl), which harbors the beige (Bg) mutation lack murine T and B lymphocytes and functional NK cells. The anti-human tumor efficacy of the bispecific antibodies was assessed using this model as described below.

The PC-3 human prostate was obtained from American Type Culture Collection and was cultured in RPMI-1640 (Invitrogen) with L-glutamine, sodium pyruvate, penicillin/streptomycin, and 10% heat inactivated fetal bovine serum (FBS, Gibco Cat. NO. 10437). Cells were grown to confluency in T-150 Falcon flasks. Subsequently, cells were trypsinized (Trypsin 0.25%-EDTA; Invitrogen) and growth was scaled up to sufficient cell number for inoculation. Peripheral blood lymphocytes (PBMCs) were isolated from heparinized blood using Lymphoprep™ in accordance with the manufactures' protocol (STEMCELL Technologies Inc.). Counted cell suspensions were combine such that each mouse received an injection of $0.75\times10^6$ PBMCs and $3\times10^6$ tumor cells in a single bolus injection of 0.1 mL in PBS. In order to facilitate the tumor cells grown in the mouse, another 0.1 mL matrigel was then mixed with the combined cell suspension and then immediately injected into prepare mice.

Figure 25:
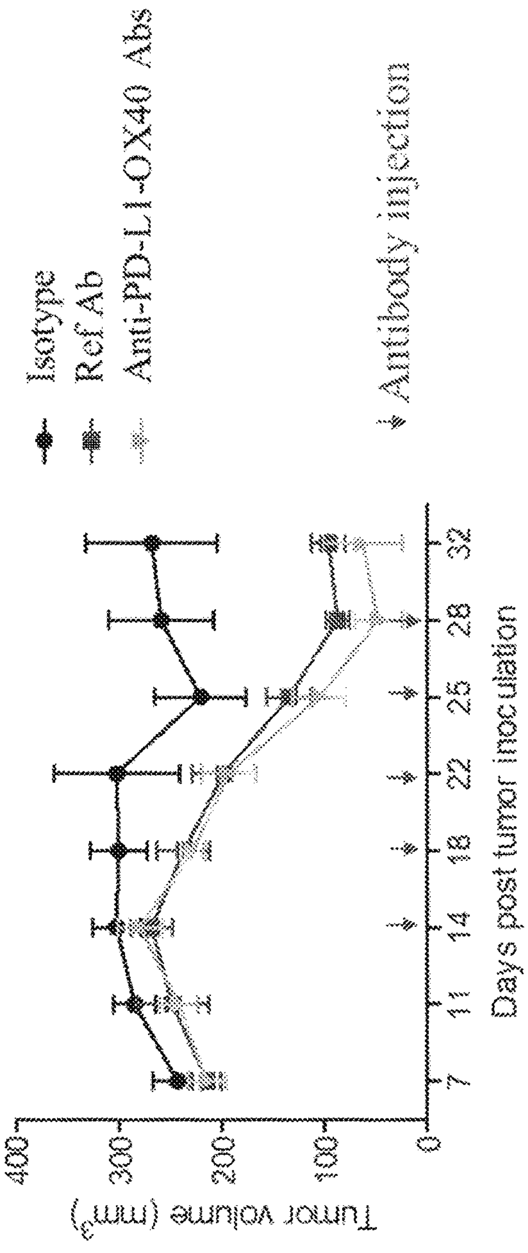
FIG. 25 is a graph showing the effect of anti-PD-L1-OX40 Ab-V5bispecific antibody treatment and monoclonal antibody treatment on the growth of PC-3 tumor in Fox Chase SCID®Beige mice.

For each mouse, 0.2 mL volume of the combined cell suspension was injected subcutaneously into the right flank of the animal. After 14 days inoculation, the solid tumor is formed and reached around 250 to 300 $mm^3$ and the bispecific antibody (3 mg/kg of Anti-PD-L1-OX40 Ab-V5), PD-L1 reference antibody (Ref Ab, MPDL3280A) or control antibody (Isotype) is challenged twice per week for three weeks with intraperitoneal injection (i.p.). Tumor measurement was made via Pressier caliper twice per week as well as test sample administration for the duration of the experiments and body weights were also recorded. Tumor volume was calculated using the following calculation: length×width$^2$×0.44=volume ($mm^3$) and plotted in the FIG. 25. Mice were removed from the study in the event that the tumor volume reached 2000 $mm^3$ or animal lost 20% of body weight before termination of the experiment. Similar results were observed when tumors were measured on day 7 post inoculation, and the animals were randomized according to tumor volume. For animal study, each group contained 6 mice. As the data shown in the FIG. 25, the bispecific antibody showed a significant anti-tumor efficiency in PC-3 xenografted mouse model. The tumor size is shirked at 18 days post tumor inoculation as well as PD-L1 reference antibody and continued to reduce below 100 $mm^3$. The PC-3 xenografted mouse model is preliminary demonstrated the anti-tumor of bispecific antibody and revealed its potential to be a therapeutic drug lead in the future.

Collectively, these results indicated bi-specific antibody sustain its immune checkpoint blocking in PD-1/PD-L1 signaling and agonistic activity for OX40 signaling. Studies are ongoing to further investigate the biological activity of these proteins using proper animal model, such as PC-3 tumor in humanized NOD.Cg-Prkdc$^{scid}$Il2rg$^{tmlwjl}$/SzJ (NSG) model.

The Fc region in the present invention could be from any immunoglobulin isotypes, subclasses, allotypes, or engineered mutants, such as knob and hole Fc fragment(s).

EXAMPLES

The example below describe the generation of monoclonal antibodies suitable for therapeutic purpose targeting human PD-L1 and OX40. Composite, human anti-human PD-L1 and anti-OX40 antibodies were generated from anti-PD-L1 antibody clone 6 and anti-OX40 antibody clone B17, respectively. Segments of human V region sequence were sourced from unrelated human antibody (germline and non-germline) sequence databases.

Example 1 Generation of IgG Antibodies that Bind to PD-L1 and OX40

Certain antibodies provided by present invention were originally generated from Fabs bind to human PD-L1 or OX40. The Fabs were selected from a phage display library, the OmniMab phagemid library, following alternating panning on corresponding Fc fusion proteins (PD-L1-Fc or OX40-Fc) and cells expressing human corresponding protein (PD-L1 or OX40). After direct ELISA or cell-based ELISA screening, the positive clones were then sequenced for heavy chain and light chain. These Fabs included those that are designated as "OM-PD-L1-6", and "OM-PDL1-32" etc. for PD-L1; "OM-OX40-A4", "OM-OX40-B17", and "OM-OX40-B19" etc. for OX40. PD-L1 antibodies PD-L1-Clone 3, PD-L1-Clone 6, and PD-L1-Clone 32 disclosed in this application were generated from "OM-PD-L1-6" and "OM-PDL1-32". Meanwhile, OX40 antibodies OX40-A4, OX40-B17, and OX40-B19 disclosed in this application were generated from "OM-OX40-A4", "OM-OX40-B17", and "OM-OX40-B19" in HEK293 cell or CHO—S cells. And bispecific antibody targeting PD-L1 and OX40 simultaneously was designed as anti-PD-L1 6-OX40 scFv B17 antibody and anti-PD-L1 6-OX40 scFv B19 antibody. The amino acid sequence of the light chain variable region and heavy chain variable region of a given Fab are identical to the amino acid sequence of the light chain variable region and heavy chain variable region, respectively.

Example 2 In Vitro Binding of Anti-PD-L1-OX40 scFv to its Corresponding Target Anti-PD-L1-OX40 bispecific antibody was constructed as shown in the FIG. 14 and expressed in the HEK293 cells or CHO—S cell. The medium containing bispecific antibody was affinity purified from culture supernatant by Protein G chromatography. Purified antibody is then concentrated, followed by dialysis in PBS buffer and analyzed by SDS-PAGE as shown in the FIG. 15. To test direct binding of purified fusion proteins to PD-L1 or OX40 on ELISA, 100 ng/well recombinant PD-L1 or OX40 was coated in a 96-well ELISA plate. Various concentrations of purified anti-PD-L1-OX40 scFv were then added to each well and incubated for 1 hr. After washing, 1:5000 dilution of anti-Fab HRP conjugate (Jackson Immunochemicals) was added to each well and incubated for another hour. After final washing, TMB substrate (Invitrogen Inc.) was added and OD absorbance at 450 nm was measured. The data analyzed by sigmoidal curve fitting using GraphPad Prism 5 and EC50 is calculated.

Example 3 Antigen Binding Specificity of Anti-PD-L1-OX40 scFv by FACS Analysis To test anti-PD-L1-OX40 scFv antibody binding specificity, stable PD-L1 expression 293 cells, IFN-γ stimulated A549 or WiDr were stained with 1 μg/mL anti-PD-L1-OX40 scFv antibody for 1 hr on ice before wash three times with 1× PBS. The bound antibody fusion proteins were detected with Alexa-488 conjugated goat anti-human IgG (H+L) followed by FACS analysis. Isotype antibody was used as negative control for the test. Results showed anti-PD-L1-OX40 scFv sustains its antigen binding specificity as compared with anti-PD-L1 alone. The binding specificity of anti-PD-L1-OX40 scFv antibody was also tested using stable OX40 expression 293 cells.

Example 4 In Vitro Immunomodulatory Effect of Bi-Functional Proteins

To measure the ability of the anti-PD-L1-OX40 scFv antibodies to modulate T cell responsiveness purified T cells will be cultured with allogeneic dendritic cells, prepared by culturing monocytes in GM-CSF and IL-4 for few days. Parallel plates were set up to allow collection of supernatants at day 3 and day 5 to measure IL-2 and IFN-γ respectively using a commercial ELISA kit. Genentech/Roche's humanized anti-PD-L1, MPDL3280A will be produced in-house and used as positive control. As the data shown in the FIGS. 16A and 16B, the IL-2 and IFN-γ production are highly upregulated in the bispecific antibody treatment as well as combination treatment after 3 or 5 days antibody treatment. Especially, the bispecific antibody composited by anti-PD-L1 antibody clone 6 and anti-OX40 antibody clone B17 (anti-PD-L1-OX40 scFv B17 Ab) or combination (anti-PD-L1 clone 6 Ab plus anti-OX40 clone B17 Ab) showed the enhancement of T cells activation is higher than the combination of PD-L1 and OX40 reference (PD-L1 Ref Ab plus OX40 Ref Ab). This indicated the anti-OX40 B17 antibody may possess a special epitope binding to result in a better agonistic activity as comparing with reference OX40 antibody, GSK3174998.

Example 5 Human Leukocyte Expansion Induced by Bispecific Antibodies In Vivo The lack of detectable cross-reactivity of the PD-L1 or OX40 antibodies with murine PD-L1 or OX40 and the requirement for the presence of human immune cells required the development of models for the in vivo functional assessment of the bispecific antibodies. Mice with the NOD genetic background carrying the severe combined immunodeficient (SCID) mutation and deficiency in the IL-2 receptor common gamma chain (commonly termed NSG) are able to support the engraftment of large number of human peripheral blood leukocytes (huPBL) and maintain engraftment for at least 30 days (King et al., 2008). This mouse model, also known as huPBL-NSG model, was used to assess the functional effect of in vivo systemic administration of the antibodies on human immune cells.

Specifically, 6 million freshly isolated human PBMCs were adoptively transferred via intravenous injection into huPBL-NSG mice. Nine days post PBMC injections, the animals were administered a single 1 mg/kg dose of monoantibody, bispecific antibody or IgG4 isotype control antibody via intraperitoneal injection. At day 24 to 28 post PBMC engraftment, PBMC were stained with antibodies to human and murine CD45 assessed via flow cytometry. Forward and side scatter profiles were used to determine a lymphocyte gate. Bispecific antibodies were able to enhance expansion of human leukocytes as evidenced by increased proportion of human CD45+ cells in the peripheral blood of engrafted mice. For each group, n≥6 mice.

Example 6 Inhibition of PC-3 or A498 Tumor Cell Growth in huPBL-NSG by Anti-PD-L1-OX40 scFv Antibody PD-L1 positive human prostate cancer cell line, PC-3 (ATCC #CRL-1435) or kidney cancer cell line, A498 (ATCC® HTB-44™) can be used to establish xenograft models in huPBL-NSG mice. For tumor formation, $3\times10^6$ PC-3 cells (or A498 cells)/mouse will be injected subcutaneously in huPBL-NSG mice as described above. In order to assess the inhibitory effects on the tumor growth, different concentrations of anti-PD-L1-OX40 scFv antibody, reference antibody, or isotype antibody from 0.1-3 mg/kg will be administered intravenously twice weekly for 4 weeks in the mice after 14 days tumor cells implantation. The tumor growth will be measured twice per week up to 5 weeks as described in the Fox Chase SCID®Beige mice model.

Example 7 Pharmacokinetic Assessment of Anti-PD-L1-OX40 scFv in Mice and Monkeys 10-40 mg/kg of bi-functional proteins, anti-PD-L1-OX40 scFv will be administered into mice or monkeys via subcutaneous injection or intravenous injection. Serum samples will be taken at different time points after the injection up to 15 days. Concentrations of the Fc fusion protein in the serum samples will be determined using a sandwiched ELISA assay.

Although the present invention has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. An antibody or an antigen-binding portion thereof binding to OX40 (CD134), comprising:

a heavy chain variable region and a light chain variable region respectively comprising an amino acid sequence of SEQ ID NO: 6 and amino acid 1-108 of SEQ ID NO: 5.

2. The antibody or the antigen-binding portion thereof of claim 1, wherein the antibody or the antigen-binding portion thereof is a single chain variable fragment (scFv), wherein the sequence of the scFv is SEQ ID NO: 11.

3. The antibody or the antigen-binding portion thereof of claim 1, wherein the antibody or the antigen-binding portion thereof is a bispecific antibody.

4. The antibody or the antigen-binding portion thereof of claim 3, wherein the bispecific antibody comprises an immune checkpoint protein binding site.

5. The antibody or the antigen-binding portion thereof of claim 4, wherein the immune checkpoint protein binding site comprises a programmed cell death protein 1 ligand (PD-L1) binding site, PD-1 binding site, epidermal growth factor receptor (EGFR) binding site, human epidermal growth factor receptor 2 (HER2) binding site, cytotoxic T-lymphocyte-associated antigen 4 (CTLA-4) binding site, or lymphocyte activation gene 3 (LAG3) binding site.

6. An antibody or an antigen-binding portion thereof binding to PD-L1, comprising:

a heavy chain variable region and a light chain variable region respectively comprising an amino acid sequence of SEQ ID NO: 2 and amino acid 1-111 of SEQ ID NO: 1.

7. A bispecific antibody comprising at least one of polypeptide chain, wherein the polypeptide chain comprises:

an OX40 binding site, comprising:

a heavy chain variable region and a light chain variable region respectively comprising an amino acid sequence of SEQ ID NO: 6 and amino acid 1-108 of SEQ ID NO: 5; and a PD-L1 binding site, comprising:

a heavy chain variable region and a light chain variable region respectively comprising an amino acid sequence of SEQ ID NO: 2 and amino acid 1-111 of SEQ ID NO: 1.

8. The bispecific antibody of claim 7, wherein the polypeptide chain comprises:

a Fc domain;

a Fab fragment connected to the N-terminus of the Fc domain, and the Fab fragment comprising the PD-L1 binding site; and a scFv connected to the C-terminus of the Fc domain, and the scFv comprising the OX40 binding site.

9. The bispecific antibody of claim 8, wherein the polypeptide chain further comprises a linker between the Fc domain and the scFv.

10. The bispecific antibody of claim 9, wherein the scFv comprises an amino acid sequence selected from the group consisting of amino acid 455-707 of SEQ ID NO: 18, 455-708 of SEQ ID NO: 19, 455-701 of SEQ ID NO: 20, 455-706 of SEQ ID NO: 21, 455-706 of SEQ ID NO: 22, 455-706 of SEQ ID NO: 23, 455-706 of SEQ ID NO: 24, 455-706 of SEQ ID NO: 25, 455-706 of SEQ ID NO: 26, 455-706 of SEQ ID NO: 27, 455-706 of SEQ ID NO: 28, and 455-706 of SEQ ID NO: 29.

11. The bispecific antibody of claim 7, wherein the bispecific antibody comprises one pair of polypeptide chains.

12. The bispecific antibody of claim 11, wherein the bispecific antibody is an IgG, IgE, IgM, IgD, IgA, or IgY antibody.

13. The bispecific antibody of claim 12, wherein the bispecific antibody is an IgG antibody.

14. The bispecific antibody of claim 13, wherein the IgG antibody is an IgG1, IgG2, IgG3, or IgG4 antibody.

15. An antibody-drug conjugate comprising:

a therapeutic agent; and an antibody or an antigen-binding portion thereof binding PD-L1 and/or OX40, wherein the therapeutic agent is covalently conjugated to the antibody or the antigen-binding portion thereof by a linker;

wherein the antibody or the antigen-binding portion thereof is:

a) an antibody or an antigen-binding portion thereof binding to OX40, comprising:

a heavy chain variable region and a light chain variable region respectively comprising an amino acid sequence of SEQ ID NO: 6 and amino acid 1-108 of SEQ ID NO: 5;

b) an antibody or an antigen-binding portion thereof binding to PD-L1, comprising:

a heavy chain variable region and a light chain variable region respectively comprising an amino acid sequence of SEQ ID NO: 2 and amino acid 1-111 of SEQ ID NO: 1; or c) a bispecific antibody comprising at least one polypeptide chain, wherein the polypeptide chain comprises:

an OX40 binding site, comprising:

a heavy chain variable region and a light chain variable region respectively comprising an amino acid sequence of SEQ ID NO: 6 and amino acid 1-108 of SEQ ID NO: 5; and a PD-L1 binding site, comprising:

a heavy chain variable region and a light chain variable region respectively comprising an amino acid sequence of SEQ ID NO: 2 and amino acid 1-111 of SEQ ID NO: 1.

16. A pharmaceutical composition comprising the antibody or the antigen-binding portion thereof according to claim 1, and at least one pharmaceutically acceptable carrier.

17. A pharmaceutical composition comprising the antibody or the antigen-binding portion thereof as claimed in claim 6, and at least one pharmaceutically acceptable carrier.

18. A pharmaceutical composition comprising the bispecific antibody according to claim 7, and at least one pharmaceutically acceptable carrier.

19. A method of treating cancer comprising administering to the subject in need thereof an effective amount of the antibody or antigen-binding portion thereof according to claim 1.

20. The method of claim 19, wherein the cancer is selected from the group consisting of prostate cancer, lung cancer, Non-Small Cell Lung Cancer (NSCLC), melanoma, lymphoma, breast cancer, head and neck cancer, renal cell carcinoma (RCC), and ovarian cancer.

21. A method of treating cancer comprising administering to the subject in need thereof an effective amount of the antibody or antigen-binding portion thereof as claimed in claim 6.

22. The method of claim 21, wherein the cancer is selected from the group consisting of prostate cancer, lung cancer, Non-Small Cell Lung Cancer (NSCLC), melanoma, lymphoma, breast cancer, head and neck cancer, renal cell carcinoma (RCC), and ovarian cancer.

23. A method of treating cancer comprising administering to the subject in need thereof an effective amount of the bispecific antibody according to claim 7.

24. The method of claim 23, wherein the cancer is selected from the group consisting of prostate cancer, lung cancer, Non-Small Cell Lung Cancer (NSCLC), melanoma, lymphoma, breast cancer, head and neck cancer, renal cell carcinoma (RCC), and ovarian cancer.

25. A nucleic acid molecule encoding the antibody or the antigen-binding portion thereof according to claim 1.

26. A nucleic acid molecule encoding the antibody or the antigen-binding portion thereof as claimed in claim 6.

27. A nucleic acid molecule encoding the bispecific antibody according to claim 7.

* * * * *

SEQUENCE LISTING

```
<160> NUMBER OF SEQ ID NOS: 43

<210> SEQ ID NO 1
<211> LENGTH: 217
<212> TYPE: PRT
<213> ORGANISM: Homo sapiens

<400> SEQUENCE: 1

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser Leu
                85                  90                  95
```

```
Asn Ala Trp Val Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215


<210> SEQ ID NO 2
<211> LENGTH: 118
<212> TYPE: PRT
<213> ORGANISM: Homo sapiens

<400> SEQUENCE: 2

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Arg Tyr
            20                  25                  30

Ser Ile Ser Trp Val Arg Gln Ala Pro Gly Gln Gly Leu Glu Trp Met
        35                  40                  45

Gly Gly Ile Ile Pro Val Phe Gly Ala Ala Lys Tyr Ala Gln Lys Phe
    50                  55                  60

Gln Gly Arg Val Thr Ile Thr Ala Asp Glu Phe Thr Ser Thr Ala Tyr
65                  70                  75                  80

Met Glu Leu Ser Ser Leu Thr Ser Glu Asp Thr Ala Val Tyr Tyr Cys
                85                  90                  95

Ala Leu Ser Gly Asp Ser Asp Ala Phe Asp Ile Trp Gly Gln Gly Thr
            100                 105                 110

Met Val Thr Val Ser Ser
        115


<210> SEQ ID NO 3
<211> LENGTH: 216
<212> TYPE: PRT
<213> ORGANISM: Homo sapiens

<400> SEQUENCE: 3

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Asn Asp Val Gly Ser Tyr
            20                  25                  30

Asn Ser Val Ser Trp Tyr Gln Gln His Pro Gly Lys Ala Pro Lys Leu
        35                  40                  45

Val Ile Tyr Glu Val Ala Asn Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80
```

```
Gln Ala Glu Asp Glu Ala Asp Tyr Tyr Cys Ser Ser Tyr Thr Ser Ser
                85                  90                  95

Ser Thr Leu Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215


<210> SEQ ID NO 4
<211> LENGTH: 121
<212> TYPE: PRT
<213> ORGANISM: Homo sapiens

<400> SEQUENCE: 4

Gln Val Gln Leu Val Gln Ser Gly Ala Lys Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Val Pro Gly Tyr Ser Tyr Gly Pro Phe Asp Tyr Trp Gly
            100                 105                 110

Gln Gly Thr Thr Val Thr Val Ser Ser
        115                 120


<210> SEQ ID NO 5
<211> LENGTH: 214
<212> TYPE: PRT
<213> ORGANISM: Homo sapiens

<400> SEQUENCE: 5

Ser Tyr Val Leu Thr Gln Pro Pro Ser Val Ser Val Thr Pro Gly Lys
1               5                   10                  15

Thr Ala Arg Ile Ala Cys Gly Gly Asn Asn Leu Glu Ser Lys Ile Val
            20                  25                  30

Ser Trp Tyr Gln Gln Lys Pro Gly Gln Ala Pro Val Leu Val Ile Phe
        35                  40                  45

Tyr Asp Thr Asp Arg Pro Ser Gly Ile Ser Glu Arg Phe Ser Gly Ser
    50                  55                  60
```

```
Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Asn Ser Asp His
                85                  90                  95

Val Ile Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210


<210> SEQ ID NO 6
<211> LENGTH: 126
<212> TYPE: PRT
<213> ORGANISM: Homo sapiens

<400> SEQUENCE: 6

Glu Val Gln Leu Val Glu Ser Gly Gly Val Val Val Gln Pro Gly Gly
1               5                   10                  15

Ser Leu Arg Leu Ser Cys Ala Ala Ser Gly Phe Thr Phe Asp Asp Tyr
            20                  25                  30

Thr Met His Trp Val Arg Gln Ala Pro Gly Lys Gly Leu Glu Trp Val
        35                  40                  45

Ser Leu Ile Ser Trp Asp Gly Gly Ser Thr Tyr Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Thr Glu Asp Thr Ala Leu Tyr Tyr Cys
                85                  90                  95

Ala Ser Ile Tyr Asp Pro Pro Pro Gly Ser Arg Ser Ala Leu Asp Ala
            100                 105                 110

Phe Asp Ile Trp Gly Gln Gly Thr Met Val Thr Val Ser Ser
        115                 120                 125


<210> SEQ ID NO 7
<211> LENGTH: 214
<212> TYPE: PRT
<213> ORGANISM: Homo sapiens

<400> SEQUENCE: 7

Ser Tyr Val Leu Thr Gln Pro Pro Ser Val Ser Val Thr Pro Gly Lys
1               5                   10                  15

Thr Ala Arg Ile Ala Cys Gly Gly Asn Asn Leu Glu Ser Lys Ile Val
            20                  25                  30

Ser Trp Tyr Gln Gln Lys Pro Gly Gln Ala Pro Val Leu Val Ile Phe
        35                  40                  45
```

```
Tyr Asp Thr Asp Arg Pro Ser Gly Ile Ser Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Asn Ser Asp His
                85                  90                  95

Val Ile Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Ala Glu Cys Ser
    210


<210> SEQ ID NO 8
<211> LENGTH: 118
<212> TYPE: PRT
<213> ORGANISM: Homo sapiens

<400> SEQUENCE: 8

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Arg Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Asn Glu Asp Val Ala Phe Gly Ile Trp Gly Gln Gly Thr
            100                 105                 110

Met Val Thr Val Ser Ser
        115


<210> SEQ ID NO 9
<211> LENGTH: 327
<212> TYPE: PRT
<213> ORGANISM: Homo sapiens

<400> SEQUENCE: 9

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30
```

-continued

```
Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 10
<211> LENGTH: 246
<212> TYPE: PRT
<213> ORGANISM: Artificial Sequence
<220> FEATURE:
<223> OTHER INFORMATION: OX40 scFv (Clone A4)

<400> SEQUENCE: 10

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Gln Arg Pro Ser Gly Val Pro Asp Arg Phe
    50                  55                  60
```

-continued

```
Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ser
                85                  90                  95

Asn Asn Leu Gly Val Phe Gly Gly Gly Thr Lys Leu Thr Val Ser Ser
            100                 105                 110

Gly Gly Gly Gly Ser Gly Gly Gly Gly Ser Gly Gly Gly Gly Ser Gln
        115                 120                 125

Val Gln Leu Val Glu Ser Gly Gly Gly Leu Val Gln Pro Gly Gly Ser
    130                 135                 140

Leu Arg Leu Ser Cys Ala Ala Ser Gly Phe Thr Phe Ser Ser Tyr Glu
145                 150                 155                 160

Met Asn Trp Val Arg Gln Ala Pro Gly Lys Gly Leu Glu Trp Val Ser
                165                 170                 175

Tyr Ile Ser Ser Ser Gly Ser Thr Ile Tyr Tyr Ala Asp Ser Val Lys
            180                 185                 190

Gly Arg Phe Thr Ile Ser Arg Asp Asn Ala Lys Asn Ser Leu Tyr Leu
        195                 200                 205

Gln Met Asn Ser Leu Arg Ala Glu Asp Thr Ala Val Tyr Tyr Cys Ala
    210                 215                 220

Arg Gly Gly Val Gly Asp Ala Phe Asp Ile Trp Gly Gln Gly Thr Met
225                 230                 235                 240

Val Thr Val Ser Ser Ala
                245


<210> SEQ ID NO 11
<211> LENGTH: 250
<212> TYPE: PRT
<213> ORGANISM: Artificial Sequence
<220> FEATURE:
<223> OTHER INFORMATION: OX40 scFv (Clone B17)

<400> SEQUENCE: 11

Tyr Val Leu Thr Gln Pro Pro Ser Val Ser Val Thr Pro Gly Lys Thr
1               5                   10                  15

Ala Arg Ile Ala Cys Gly Gly Asn Asn Leu Glu Ser Lys Ile Val Ser
            20                  25                  30

Trp Tyr Gln Gln Lys Pro Gly Gln Ala Pro Val Leu Val Ile Phe Tyr
        35                  40                  45

Asp Thr Asp Arg Pro Ser Gly Ile Ser Glu Arg Phe Ser Gly Ser Asn
    50                  55                  60

Ser Gly Asn Thr Ala Thr Leu Thr Ile Ser Arg Val Glu Ala Gly Asp
65                  70                  75                  80

Glu Ala Asp Tyr Tyr Cys Gln Val Trp Asp Ser Asn Ser Asp His Val
                85                  90                  95

Ile Phe Gly Gly Gly Thr Lys Leu Thr Val Ser Ser Gly Gly Gly Gly
            100                 105                 110

Ser Gly Gly Gly Gly Ser Gly Gly Gly Gly Ser Glu Val Gln Leu Val
        115                 120                 125

Glu Ser Gly Gly Val Val Val Gln Pro Gly Gly Ser Leu Arg Leu Ser
    130                 135                 140

Cys Ala Ala Ser Gly Phe Thr Phe Asp Asp Tyr Thr Met His Trp Val
145                 150                 155                 160

Arg Gln Ala Pro Gly Lys Gly Leu Glu Trp Val Ser Leu Ile Ser Trp
                165                 170                 175
```

```
Asp Gly Gly Ser Thr Tyr Tyr Ala Asp Ser Val Lys Gly Arg Phe Thr
            180                 185                 190

Ile Ser Arg Asp Asn Ser Lys Asn Ser Leu Tyr Leu Gln Met Asn Ser
        195                 200                 205

Leu Arg Thr Glu Asp Thr Ala Leu Tyr Tyr Cys Ala Ser Ile Tyr Asp
    210                 215                 220

Pro Pro Pro Gly Ser Arg Ser Ala Leu Asp Ala Phe Asp Ile Trp Gly
225                 230                 235                 240

Gln Gly Thr Met Val Thr Val Ser Ser Ala
                245                 250


<210> SEQ ID NO 12
<211> LENGTH: 243
<212> TYPE: PRT
<213> ORGANISM: Artificial Sequence
<220> FEATURE:
<223> OTHER INFORMATION: OX40 scFv (Clone B19)

<400> SEQUENCE: 12

Ser Tyr Val Leu Thr Gln Pro Pro Ser Val Ser Val Thr Pro Gly Lys
1               5                   10                  15

Thr Ala Arg Ile Ala Cys Gly Gly Asn Asn Leu Glu Ser Lys Ile Val
            20                  25                  30

Ser Trp Tyr Gln Gln Lys Pro Gly Gln Ala Pro Val Leu Val Ile Phe
        35                  40                  45

Tyr Asp Thr Asp Arg Pro Ser Gly Ile Ser Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Asn Ser Asp His
                85                  90                  95

Val Ile Phe Gly Gly Gly Thr Lys Leu Thr Val Ser Ser Gly Gly Gly
            100                 105                 110

Gly Ser Gly Gly Gly Gly Ser Gly Gly Gly Gly Ser Glu Val Gln Leu
        115                 120                 125

Val Glu Ser Gly Gly Gly Leu Val Lys Pro Gly Gly Ser Leu Arg Leu
    130                 135                 140

Ser Cys Ala Ala Ser Gly Phe Thr Phe Ser Ser Tyr Ser Met Asn Trp
145                 150                 155                 160

Val Arg Gln Ala Pro Gly Lys Gly Leu Glu Trp Val Ser Ser Ile Ser
                165                 170                 175

Ser Ser Ser Arg Tyr Ile Tyr Tyr Ala Asp Ser Val Lys Gly Arg Phe
            180                 185                 190

Thr Ile Ser Arg Asp Asn Ala Lys Asn Ser Leu Tyr Leu Gln Met Asn
        195                 200                 205

Ser Leu Arg Ala Glu Asp Thr Ala Val Tyr Tyr Cys Ala Arg Gln Asn
    210                 215                 220

Glu Asp Val Ala Phe Gly Ile Trp Gly Gln Gly Thr Met Val Thr Val
225                 230                 235                 240

Ser Ser Ala


<210> SEQ ID NO 13
<211> LENGTH: 241
<212> TYPE: PRT
<213> ORGANISM: Artificial Sequence
<220> FEATURE:
```

-continued

<223> OTHER INFORMATION: OX40 scFv (Clone B120)

<400> SEQUENCE: 13

Ser Tyr Glu Leu Thr Gln Pro Pro Ser Val Ser Val Ser Pro Gly Gln
1               5                   10                  15

Thr Ala Ser Ile Thr Cys Ser Gly Asp Thr Leu Gly Asp Lys Tyr Ala
            20                  25                  30

Ser Trp Tyr Gln Gln Lys Pro Gly Arg Ser Pro Val Leu Val Ile Tyr
        35                  40                  45

Gln Asp Ser Glu Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Ser Tyr
                85                  90                  95

Val Phe Gly Thr Gly Thr Lys Val Thr Val Ser Ser Gly Gly Gly Gly
            100                 105                 110

Ser Gly Gly Gly Gly Ser Gly Gly Gly Gly Ser Gln Val Gln Leu Gln
        115                 120                 125

Gln Trp Gly Ala Gly Leu Leu Lys Pro Ser Glu Thr Leu Ser Leu Thr
    130                 135                 140

Cys Ala Val Tyr Gly Gly Ser Phe Ser Gly Tyr Tyr Trp Ser Trp Ile
145                 150                 155                 160

Arg Gln Pro Pro Gly Lys Gly Leu Glu Trp Ile Gly Glu Ile Asn His
                165                 170                 175

Ser Gly Ser Thr Asn Tyr Asn Pro Ser Leu Lys Ser Arg Val Thr Ile
            180                 185                 190

Ser Val Asp Thr Ser Lys Asn Gln Phe Ser Leu Lys Leu Ser Ser Val
        195                 200                 205

Thr Ala Ala Asp Thr Ala Val Tyr Tyr Cys Ala Arg Gly Arg Trp Gly
    210                 215                 220

Gly Ser Phe Ile Tyr Trp Gly Gln Gly Thr Leu Val Thr Val Ser Ser
225                 230                 235                 240

Ala

<210> SEQ ID NO 14
<211> LENGTH: 10
<212> TYPE: PRT
<213> ORGANISM: Artificial Sequence
<220> FEATURE:
<223> OTHER INFORMATION: peptide linker

<400> SEQUENCE: 14

Gly Gly Gly Gly Ser Gly Gly Gly Gly Ser
1               5                   10

<210> SEQ ID NO 15
<211> LENGTH: 20
<212> TYPE: PRT
<213> ORGANISM: Artificial Sequence
<220> FEATURE:
<223> OTHER INFORMATION: signal peptide

<400> SEQUENCE: 15

Met Glu Thr Asp Thr Leu Leu Leu Trp Val Leu Leu Leu Trp Val Pro
1               5                   10                  15

Gly Ser Thr Gly
            20

<210> SEQ ID NO 16
<211> LENGTH: 704
<212> TYPE: PRT
<213> ORGANISM: Artificial Sequence
<220> FEATURE:
<223> OTHER INFORMATION: Anti-PD-L1-clone 6 Heavy Chain-OX40 clone B17
scFv antibody

<400> SEQUENCE: 16

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Arg Tyr
            20                  25                  30

Ser Ile Ser Trp Val Arg Gln Ala Pro Gly Gln Gly Leu Glu Trp Met
        35                  40                  45

Gly Gly Ile Ile Pro Val Phe Gly Ala Ala Lys Tyr Ala Gln Lys Phe
    50                  55                  60

Gln Gly Arg Val Thr Ile Thr Ala Asp Glu Phe Thr Ser Thr Ala Tyr
65                  70                  75                  80

Met Glu Leu Ser Ser Leu Thr Ser Glu Asp Thr Ala Val Tyr Tyr Cys
                85                  90                  95

Ala Leu Ser Gly Asp Ser Asp Ala Phe Asp Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
```

```
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Gly Gly Gly Gly
        435                 440                 445

Ser Gly Gly Gly Gly Ser Tyr Val Leu Thr Gln Pro Pro Ser Val Ser
    450                 455                 460

Val Thr Pro Gly Lys Thr Ala Arg Ile Ala Cys Gly Gly Asn Asn Leu
465                 470                 475                 480

Glu Ser Lys Ile Val Ser Trp Tyr Gln Gln Lys Pro Gly Gln Ala Pro
                485                 490                 495

Val Leu Val Ile Phe Tyr Asp Thr Asp Arg Pro Ser Gly Ile Ser Glu
            500                 505                 510

Arg Phe Ser Gly Ser Asn Ser Gly Asn Thr Ala Thr Leu Thr Ile Ser
        515                 520                 525

Arg Val Glu Ala Gly Asp Glu Ala Asp Tyr Tyr Cys Gln Val Trp Asp
    530                 535                 540

Ser Asn Ser Asp His Val Ile Phe Gly Gly Gly Thr Lys Leu Thr Val
545                 550                 555                 560

Ser Ser Gly Gly Gly Gly Ser Gly Gly Gly Gly Ser Gly Gly Gly Gly
                565                 570                 575

Ser Glu Val Gln Leu Val Glu Ser Gly Gly Val Val Val Gln Pro Gly
            580                 585                 590

Gly Ser Leu Arg Leu Ser Cys Ala Ala Ser Gly Phe Thr Phe Asp Asp
        595                 600                 605

Tyr Thr Met His Trp Val Arg Gln Ala Pro Gly Lys Gly Leu Glu Trp
    610                 615                 620

Val Ser Leu Ile Ser Trp Asp Gly Gly Ser Thr Tyr Tyr Ala Asp Ser
625                 630                 635                 640

Val Lys Gly Arg Phe Thr Ile Ser Arg Asp Asn Ser Lys Asn Ser Leu
                645                 650                 655

Tyr Leu Gln Met Asn Ser Leu Arg Thr Glu Asp Thr Ala Leu Tyr Tyr
            660                 665                 670

Cys Ala Ser Ile Tyr Asp Pro Pro Pro Gly Ser Arg Ser Ala Leu Asp
        675                 680                 685

Ala Phe Asp Ile Trp Gly Gln Gly Thr Met Val Thr Val Ser Ser Ala
    690                 695                 700


<210> SEQ ID NO 17
<211> LENGTH: 696
<212> TYPE: PRT
<213> ORGANISM: Artificial Sequence
<220> FEATURE:
<223> OTHER INFORMATION: Anti-PD-L1-clone 6 Heavy Chain-OX40 clone B19
      scFv antibody

<400> SEQUENCE: 17

Gln Val Gln Leu Val Gln Ser Gly Ala Glu Val Lys Lys Pro Gly Ser
1               5                   10                  15
```

-continued

```
Ser Val Lys Val Ser Cys Lys Ala Ser Gly Gly Thr Phe Arg Arg Tyr
            20                  25                  30

Ser Ile Ser Trp Val Arg Gln Ala Pro Gly Gln Gly Leu Glu Trp Met
        35                  40                  45

Gly Gly Ile Ile Pro Val Phe Gly Ala Ala Lys Tyr Ala Gln Lys Phe
    50                  55                  60

Gln Gly Arg Val Thr Ile Thr Ala Asp Glu Phe Thr Ser Thr Ala Tyr
65                  70                  75                  80

Met Glu Leu Ser Ser Leu Thr Ser Glu Asp Thr Ala Val Tyr Tyr Cys
                85                  90                  95

Ala Leu Ser Gly Asp Ser Asp Ala Phe Asp Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Gly Gly Gly Gly
```

-continued

```
        435                 440                 445

Ser Gly Gly Gly Gly Ser Tyr Val Leu Thr Gln Pro Pro Ser Val Ser
    450                 455                 460

Val Thr Pro Gly Lys Thr Ala Arg Ile Ala Cys Gly Gly Asn Asn Leu
465                 470                 475                 480

Glu Ser Lys Ile Val Ser Trp Tyr Gln Gln Lys Pro Gly Gln Ala Pro
                485                 490                 495

Val Leu Val Ile Phe Tyr Asp Thr Asp Arg Pro Ser Gly Ile Ser Glu
            500                 505                 510

Arg Phe Ser Gly Ser Asn Ser Gly Asn Thr Ala Thr Leu Thr Ile Ser
        515                 520                 525

Arg Val Glu Ala Gly Asp Glu Ala Asp Tyr Tyr Cys Gln Val Trp Asp
    530                 535                 540

Ser Asn Ser Asp His Val Ile Phe Gly Gly Gly Thr Lys Leu Thr Val
545                 550                 555                 560

Ser Ser Gly Gly Gly Gly Ser Gly Gly Gly Gly Ser Gly Gly Gly Gly
                565                 570                 575

Ser Glu Val Gln Leu Val Glu Ser Gly Gly Gly Leu Val Lys Pro Gly
            580                 585                 590

Gly Ser Leu Arg Leu Ser Cys Ala Ala Ser Gly Phe Thr Phe Ser Ser
        595                 600                 605

Tyr Ser Met Asn Trp Val Arg Gln Ala Pro Gly Lys Gly Leu Glu Trp
    610                 615                 620

Val Ser Ser Ile Ser Ser Ser Ser Arg Tyr Ile Tyr Tyr Ala Asp Ser
625                 630                 635                 640

Val Lys Gly Arg Phe Thr Ile Ser Arg Asp Asn Ala Lys Asn Ser Leu
                645                 650                 655

Tyr Leu Gln Met Asn Ser Leu Arg Ala Glu Asp Thr Ala Val Tyr Tyr
            660                 665                 670

Cys Ala Arg Gln Asn Glu Asp Val Ala Phe Gly Ile Trp Gly Gln Gly
        675                 680                 685

Thr Met Val Thr Val Ser Ser Ala
    690                 695


<210> SEQ ID NO 18
<211> LENGTH: 707
<212> TYPE: PRT
<213> ORGANISM: Artificial Sequence
<220> FEATURE:
<223> OTHER INFORMATION: Anti-PD-L1-OX40 Ab-V1

<400> SEQUENCE: 18

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Arg Tyr
            20                  25                  30

Ser Ile Ser Trp Val Arg Gln Ala Pro Gly Gln Gly Leu Glu Trp Met
        35                  40                  45

Gly Gly Ile Ile Pro Val Phe Gly Ala Ala Lys Tyr Ala Gln Lys Phe
    50                  55                  60

Gln Gly Arg Val Thr Ile Thr Ala Asp Glu Phe Thr Ser Thr Ala Tyr
65                  70                  75                  80

Met Glu Leu Ser Ser Leu Thr Ser Glu Asp Thr Ala Val Tyr Tyr Cys
                85                  90                  95

Ala Leu Ser Gly Asp Ser Asp Ala Phe Asp Ile Trp Gly Gln Gly Thr
```

-continued

```
            100                 105                 110

Met Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Gly Gly Gly Gly
        435                 440                 445

Ser Gly Gly Gly Gly Ser Tyr Val Leu Thr Gln Pro Pro Ser Val Ser
    450                 455                 460

Val Thr Pro Gly Lys Thr Ala Arg Ile Ala Cys Gly Gly Asn Asn Leu
465                 470                 475                 480

Glu Ser Lys Ile Val Ser Trp Tyr Gln Gln Lys Pro Gly Gln Ala Pro
                485                 490                 495

Val Leu Val Ile Phe Tyr Asp Thr Asp Arg Pro Ser Gly Ile Ser Glu
            500                 505                 510

Arg Phe Ser Gly Ser Asn Ser Gly Asn Thr Ala Thr Leu Thr Ile Ser
        515                 520                 525
```

-continued

```
Arg Val Glu Ala Gly Asp Glu Ala Asp Tyr Tyr Cys Gln Val Trp Asp
    530                 535                 540

Ser Asn Ser Asp His Val Ile Phe Gly Gly Gly Thr Lys Leu Thr Val
545                 550                 555                 560

Leu Ser Ser Gly Gly Gly Gly Ser Gly Gly Gly Gly Gly Gly Ser Ser
                565                 570                 575

Arg Ser Ser Leu Glu Val Gln Leu Val Glu Ser Gly Gly Val Val Val
            580                 585                 590

Gln Pro Gly Gly Ser Leu Arg Leu Ser Cys Ala Ala Ser Gly Phe Thr
        595                 600                 605

Phe Asp Asp Tyr Thr Met His Trp Val Arg Gln Ala Pro Gly Lys Gly
    610                 615                 620

Leu Glu Trp Val Ser Leu Ile Ser Trp Asp Gly Gly Ser Thr Tyr Tyr
625                 630                 635                 640

Ala Asp Ser Val Lys Gly Arg Phe Thr Ile Ser Arg Asp Asn Ser Lys
                645                 650                 655

Asn Ser Leu Tyr Leu Gln Met Asn Ser Leu Arg Thr Glu Asp Thr Ala
            660                 665                 670

Leu Tyr Tyr Cys Ala Ser Ile Tyr Asp Pro Pro Pro Gly Ser Arg Ser
        675                 680                 685

Ala Leu Asp Ala Phe Asp Ile Trp Gly Gln Gly Thr Met Val Thr Val
    690                 695                 700

Ser Ser Ala
705
```

<210> SEQ ID NO 19
<211> LENGTH: 708
<212> TYPE: PRT
<213> ORGANISM: Artificial Sequence
<220> FEATURE:
<223> OTHER INFORMATION: Anti-PD-L1-OX40 Ab-V2

<400> SEQUENCE: 19

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Arg Tyr
            20                  25                  30

Ser Ile Ser Trp Val Arg Gln Ala Pro Gly Gln Gly Leu Glu Trp Met
        35                  40                  45

Gly Gly Ile Ile Pro Val Phe Gly Ala Ala Lys Tyr Ala Gln Lys Phe
    50                  55                  60

Gln Gly Arg Val Thr Ile Thr Ala Asp Glu Phe Thr Ser Thr Ala Tyr
65                  70                  75                  80

Met Glu Leu Ser Ser Leu Thr Ser Glu Asp Thr Ala Val Tyr Tyr Cys
                85                  90                  95

Ala Leu Ser Gly Asp Ser Asp Ala Phe Asp Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175
```

```
Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Gly Gly Gly Gly
        435                 440                 445

Ser Gly Gly Gly Gly Ser Tyr Val Leu Thr Gln Pro Pro Ser Val Ser
    450                 455                 460

Val Thr Pro Gly Lys Thr Ala Arg Ile Ala Cys Gly Gly Asn Asn Leu
465                 470                 475                 480

Glu Ser Lys Ile Val Ser Trp Tyr Gln Gln Lys Pro Gly Gln Ala Pro
                485                 490                 495

Val Leu Val Ile Phe Tyr Asp Thr Asp Arg Pro Ser Gly Ile Ser Glu
            500                 505                 510

Arg Phe Ser Gly Ser Asn Ser Gly Asn Thr Ala Thr Leu Thr Ile Ser
        515                 520                 525

Arg Val Glu Ala Gly Asp Glu Ala Asp Tyr Tyr Cys Gln Val Trp Asp
    530                 535                 540

Ser Asn Ser Asp His Val Ile Phe Gly Gly Gly Thr Lys Leu Thr Val
545                 550                 555                 560

Leu Gly Gly Lys Gly Ser Gly Gly Lys Gly Thr Gly Gly Lys Gly Ser
                565                 570                 575

Gly Gly Lys Gly Ser Glu Val Gln Leu Val Glu Ser Gly Gly Val Val
            580                 585                 590
```

```
Val Gln Pro Gly Gly Ser Leu Arg Leu Ser Cys Ala Ala Ser Gly Phe
        595                 600                 605

Thr Phe Asp Asp Tyr Thr Met His Trp Val Arg Gln Ala Pro Gly Lys
    610                 615                 620

Gly Leu Glu Trp Val Ser Leu Ile Ser Trp Asp Gly Gly Ser Thr Tyr
625                 630                 635                 640

Tyr Ala Asp Ser Val Lys Gly Arg Phe Thr Ile Ser Arg Asp Asn Ser
                645                 650                 655

Lys Asn Ser Leu Tyr Leu Gln Met Asn Ser Leu Arg Thr Glu Asp Thr
            660                 665                 670

Ala Leu Tyr Tyr Cys Ala Ser Ile Tyr Asp Pro Pro Pro Gly Ser Arg
        675                 680                 685

Ser Ala Leu Asp Ala Phe Asp Ile Trp Gly Gln Gly Thr Met Val Thr
    690                 695                 700

Val Ser Ser Ala
705


<210> SEQ ID NO 20
<211> LENGTH: 701
<212> TYPE: PRT
<213> ORGANISM: Artificial Sequence
<220> FEATURE:
<223> OTHER INFORMATION: Anti-PD-L1-OX40 Ab-V3

<400> SEQUENCE: 20

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Arg Tyr
            20                  25                  30

Ser Ile Ser Trp Val Arg Gln Ala Pro Gly Gln Gly Leu Glu Trp Met
        35                  40                  45

Gly Gly Ile Ile Pro Val Phe Gly Ala Ala Lys Tyr Ala Gln Lys Phe
    50                  55                  60

Gln Gly Arg Val Thr Ile Thr Ala Asp Glu Phe Thr Ser Thr Ala Tyr
65                  70                  75                  80

Met Glu Leu Ser Ser Leu Thr Ser Glu Asp Thr Ala Val Tyr Tyr Cys
                85                  90                  95

Ala Leu Ser Gly Asp Ser Asp Ala Phe Asp Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240
```

-continued

```
Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Gly Gly Gly Gly
        435                 440                 445

Ser Gly Gly Gly Gly Ser Tyr Val Leu Thr Gln Pro Pro Ser Val Ser
    450                 455                 460

Val Thr Pro Gly Lys Thr Ala Arg Ile Ala Cys Gly Gly Asn Asn Leu
465                 470                 475                 480

Glu Ser Lys Ile Val Ser Trp Tyr Gln Gln Lys Pro Gly Gln Ala Pro
                485                 490                 495

Val Leu Val Ile Phe Tyr Asp Thr Asp Arg Pro Ser Gly Ile Ser Glu
            500                 505                 510

Arg Phe Ser Gly Ser Asn Ser Gly Asn Thr Ala Thr Leu Thr Ile Ser
        515                 520                 525

Arg Val Glu Ala Gly Asp Glu Ala Asp Tyr Tyr Cys Gln Val Trp Asp
    530                 535                 540

Ser Asn Ser Asp His Val Ile Phe Gly Gly Gly Thr Lys Leu Thr Val
545                 550                 555                 560

Leu Gly Ser Ala Ser Ala Pro Thr Leu Phe Pro Leu Val Ser Glu Val
                565                 570                 575

Gln Leu Val Glu Ser Gly Gly Val Val Val Gln Pro Gly Gly Ser Leu
            580                 585                 590

Arg Leu Ser Cys Ala Ala Ser Gly Phe Thr Phe Asp Asp Tyr Thr Met
        595                 600                 605

His Trp Val Arg Gln Ala Pro Gly Lys Gly Leu Glu Trp Val Ser Leu
    610                 615                 620

Ile Ser Trp Asp Gly Gly Ser Thr Tyr Tyr Ala Asp Ser Val Lys Gly
625                 630                 635                 640

Arg Phe Thr Ile Ser Arg Asp Asn Ser Lys Asn Ser Leu Tyr Leu Gln
                645                 650                 655

Met Asn Ser Leu Arg Thr Glu Asp Thr Ala Leu Tyr Tyr Cys Ala Ser
```

```
            660                 665                 670

Ile Tyr Asp Pro Pro Pro Gly Ser Arg Ser Ala Leu Asp Ala Phe Asp
        675                 680                 685

Ile Trp Gly Gln Gly Thr Met Val Thr Val Ser Ser Ala
    690                 695                 700


<210> SEQ ID NO 21
<211> LENGTH: 706
<212> TYPE: PRT
<213> ORGANISM: Artificial Sequence
<220> FEATURE:
<223> OTHER INFORMATION: Anti-PD-L1-OX40 Ab-V4

<400> SEQUENCE: 21

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Arg Tyr
            20                  25                  30

Ser Ile Ser Trp Val Arg Gln Ala Pro Gly Gln Gly Leu Glu Trp Met
        35                  40                  45

Gly Gly Ile Ile Pro Val Phe Gly Ala Ala Lys Tyr Ala Gln Lys Phe
    50                  55                  60

Gln Gly Arg Val Thr Ile Thr Ala Asp Glu Phe Thr Ser Thr Ala Tyr
65                  70                  75                  80

Met Glu Leu Ser Ser Leu Thr Ser Glu Asp Thr Ala Val Tyr Tyr Cys
                85                  90                  95

Ala Leu Ser Gly Asp Ser Asp Ala Phe Asp Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
```

-continued

```
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Gly Gly Gly Gly
        435                 440                 445

Ser Gly Gly Gly Gly Ser Tyr Val Leu Thr Gln Pro Pro Ser Val Ser
    450                 455                 460

Val Thr Pro Gly Lys Thr Ala Arg Ile Ala Cys Gly Gly Asn Asn Leu
465                 470                 475                 480

Glu Ser Lys Ile Val Ser Trp Tyr Gln Gln Lys Pro Gly Gln Ala Pro
                485                 490                 495

Val Leu Val Ile Phe Tyr Asp Thr Asp Arg Pro Ser Gly Ile Ser Glu
            500                 505                 510

Arg Phe Ser Gly Ser Asn Ser Gly Asn Thr Ala Thr Leu Thr Ile Ser
        515                 520                 525

Arg Val Glu Ala Gly Asp Glu Ala Asp Tyr Tyr Cys Gln Val Trp Asp
    530                 535                 540

Ser Asn Ser Asp His Val Ile Phe Gly Gly Gly Thr Lys Leu Thr Val
545                 550                 555                 560

Leu Gly Ser Thr Ser Gly Ser Gly Lys Pro Gly Ser Gly Glu Gly Ser
                565                 570                 575

Thr Lys Gly Glu Val Gln Leu Val Glu Ser Gly Gly Val Val Val Gln
            580                 585                 590

Pro Gly Gly Ser Leu Arg Leu Ser Cys Ala Ala Ser Gly Phe Thr Phe
        595                 600                 605

Asp Asp Tyr Thr Met His Trp Val Arg Gln Ala Pro Gly Lys Gly Leu
    610                 615                 620

Glu Trp Val Ser Leu Ile Ser Trp Asp Gly Gly Ser Thr Tyr Tyr Ala
625                 630                 635                 640

Asp Ser Val Lys Gly Arg Phe Thr Ile Ser Arg Asp Asn Ser Lys Asn
                645                 650                 655

Ser Leu Tyr Leu Gln Met Asn Ser Leu Arg Thr Glu Asp Thr Ala Leu
            660                 665                 670

Tyr Tyr Cys Ala Ser Ile Tyr Asp Pro Pro Pro Gly Ser Arg Ser Ala
        675                 680                 685

Leu Asp Ala Phe Asp Ile Trp Gly Gln Gly Thr Met Val Thr Val Ser
    690                 695                 700

Ser Ala
705
```

<210> SEQ ID NO 22
<211> LENGTH: 706
<212> TYPE: PRT
<213> ORGANISM: Artificial Sequence -continued
<220> FEATURE:
<223> OTHER INFORMATION: Anti-PD-L1-OX40 Ab-V5

<400> SEQUENCE: 22

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Arg Tyr
            20                  25                  30

Ser Ile Ser Trp Val Arg Gln Ala Pro Gly Gln Gly Leu Glu Trp Met
        35                  40                  45

Gly Gly Ile Ile Pro Val Phe Gly Ala Ala Lys Tyr Ala Gln Lys Phe
    50                  55                  60

Gln Gly Arg Val Thr Ile Thr Ala Asp Glu Phe Thr Ser Thr Ala Tyr
65                  70                  75                  80

Met Glu Leu Ser Ser Leu Thr Ser Glu Asp Thr Ala Val Tyr Tyr Cys
                85                  90                  95

Ala Leu Ser Gly Asp Ser Asp Ala Phe Asp Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400
```

-continued

```
Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Gly Gly Gly Gly
        435                 440                 445

Ser Gly Gly Gly Gly Ser Tyr Glu Leu Thr Gln Pro Pro Ser Val Ser
    450                 455                 460

Val Thr Pro Gly Gln Thr Ala Arg Ile Ala Cys Gly Gly Asn Asn Leu
465                 470                 475                 480

Glu Ser Lys Ile Val Ser Trp Tyr Gln Gln Lys Pro Gly Gln Ala Pro
                485                 490                 495

Val Leu Val Ile Phe Tyr Asp Thr Asp Arg Pro Ser Gly Ile Ser Glu
            500                 505                 510

Arg Phe Ser Gly Ser Asn Ser Gly Asn Thr Ala Thr Leu Thr Ile Ser
        515                 520                 525

Arg Val Glu Ala Gly Asp Glu Ala Asp Tyr Tyr Cys Gln Val Trp Asp
    530                 535                 540

Ser Asn Ser Asp His Val Ile Phe Gly Gly Gly Thr Lys Leu Thr Val
545                 550                 555                 560

Leu Gly Ser Thr Ser Gly Ser Gly Lys Pro Gly Ser Gly Glu Gly Ser
                565                 570                 575

Thr Lys Gly Glu Val Gln Leu Val Glu Ser Gly Gly Val Val Val Gln
            580                 585                 590

Pro Gly Gly Ser Leu Arg Leu Ser Cys Ala Ala Ser Gly Phe Thr Phe
        595                 600                 605

Asp Asp Tyr Thr Met His Trp Val Arg Gln Ala Pro Gly Lys Gly Leu
    610                 615                 620

Glu Trp Val Ser Leu Ile Ser Trp Asp Gly Gly Ser Thr Tyr Tyr Ala
625                 630                 635                 640

Asp Ser Val Lys Gly Arg Phe Thr Ile Ser Arg Asp Asn Ser Lys Asn
                645                 650                 655

Ser Leu Tyr Leu Gln Met Asn Ser Leu Arg Thr Glu Asp Thr Ala Leu
            660                 665                 670

Tyr Tyr Cys Ala Ser Ile Tyr Asp Pro Pro Pro Gly Ser Arg Ser Ala
        675                 680                 685

Leu Asp Ala Phe Asp Ile Trp Gly Gln Gly Thr Met Val Thr Val Ser
    690                 695                 700

Ser Ala
705


<210> SEQ ID NO 23
<211> LENGTH: 706
<212> TYPE: PRT
<213> ORGANISM: Artificial Sequence
<220> FEATURE:
<223> OTHER INFORMATION: Anti-PD-L1-OX40 Ab-V6

<400> SEQUENCE: 23

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Arg Tyr
            20                  25                  30

Ser Ile Ser Trp Val Arg Gln Ala Pro Gly Gln Gly Leu Glu Trp Met
        35                  40                  45
```

-continued

```
Gly Gly Ile Ile Pro Val Phe Gly Ala Ala Lys Tyr Ala Gln Lys Phe
    50                  55                  60

Gln Gly Arg Val Thr Ile Thr Ala Asp Glu Phe Thr Ser Thr Ala Tyr
65                  70                  75                  80

Met Glu Leu Ser Ser Leu Thr Ser Glu Asp Thr Ala Val Tyr Tyr Cys
                85                  90                  95

Ala Leu Ser Gly Asp Ser Asp Ala Phe Asp Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Gly Gly Gly Gly
        435                 440                 445

Ser Gly Gly Gly Gly Ser Tyr Val Leu Thr Gln Pro Pro Ser Val Ser
    450                 455                 460
```

-continued

```
Val Thr Pro Gly Glu Thr Ala Arg Ile Ala Cys Gly Gly Asn Asn Leu
465                 470                 475                 480

Glu Ser Lys Ile Val Ser Trp Tyr Gln Gln Lys Pro Gly Gln Ala Pro
                485                 490                 495

Val Leu Val Ile Phe Tyr Asp Thr Asp Arg Pro Ser Gly Ile Ser Glu
            500                 505                 510

Arg Phe Ser Gly Ser Asn Ser Gly Asn Thr Ala Thr Leu Thr Ile Ser
        515                 520                 525

Arg Val Glu Ala Gly Asp Glu Ala Asp Tyr Tyr Cys Gln Val Trp Asp
    530                 535                 540

Ser Asn Ser Asp His Val Val Phe Gly Gly Gly Thr Lys Leu Thr Val
545                 550                 555                 560

Leu Gly Ser Thr Ser Gly Ser Gly Lys Pro Gly Ser Gly Glu Gly Ser
                565                 570                 575

Thr Lys Gly Glu Val Gln Leu Val Glu Ser Gly Gly Gly Val Val Gln
            580                 585                 590

Pro Gly Gly Ser Leu Arg Leu Ser Cys Ala Ala Ser Gly Phe Thr Phe
        595                 600                 605

Asp Asp Tyr Thr Met His Trp Val Arg Gln Ala Pro Gly Lys Gly Leu
    610                 615                 620

Glu Trp Val Ser Leu Ile Ser Trp Asp Gly Gly Ser Thr Tyr Tyr Ala
625                 630                 635                 640

Asp Ser Val Lys Gly Arg Phe Thr Ile Ser Arg Asp Asn Ser Lys Asn
                645                 650                 655

Ser Leu Tyr Leu Gln Met Asn Ser Leu Arg Thr Glu Asp Thr Ala Leu
            660                 665                 670

Tyr Tyr Cys Ala Ser Ile Tyr Asp Pro Pro Pro Gly Ser Arg Ser Ala
        675                 680                 685

Leu Asp Ala Phe Asp Ile Trp Gly Gln Gly Thr Met Val Thr Val Ser
    690                 695                 700

Ser Ala
705


<210> SEQ ID NO 24
<211> LENGTH: 706
<212> TYPE: PRT
<213> ORGANISM: Artificial Sequence
<220> FEATURE:
<223> OTHER INFORMATION: Anti-PD-L1-OX40 Ab-V7

<400> SEQUENCE: 24

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Arg Tyr
            20                  25                  30

Ser Ile Ser Trp Val Arg Gln Ala Pro Gly Gln Gly Leu Glu Trp Met
        35                  40                  45

Gly Gly Ile Ile Pro Val Phe Gly Ala Ala Lys Tyr Ala Gln Lys Phe
    50                  55                  60

Gln Gly Arg Val Thr Ile Thr Ala Asp Glu Phe Thr Ser Thr Ala Tyr
65                  70                  75                  80

Met Glu Leu Ser Ser Leu Thr Ser Glu Asp Thr Ala Val Tyr Tyr Cys
                85                  90                  95

Ala Leu Ser Gly Asp Ser Asp Ala Phe Asp Ile Trp Gly Gln Gly Thr
            100                 105                 110
```

-continued

```
Met Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Gly Gly Gly Gly
        435                 440                 445

Ser Gly Gly Gly Gly Ser Tyr Val Leu Thr Gln Pro Pro Ser Val Ser
    450                 455                 460

Val Thr Pro Gly Gln Thr Ala Arg Ile Ala Cys Gly Gly Asn Asn Leu
465                 470                 475                 480

Glu Ser Lys Ile Val Ser Trp Tyr Gln Gln Lys Pro Gly Gln Ala Pro
                485                 490                 495

Val Leu Val Ile Phe Tyr Asp Thr Asp Arg Pro Ser Gly Ile Ser Glu
            500                 505                 510

Arg Phe Ser Gly Ser Asn Ser Gly Asn Thr Ala Thr Leu Thr Ile Ser
        515                 520                 525

Arg Val Glu Ala Gly Asp Glu Ala Asp Tyr Tyr Cys Gln Val Trp Asp
```

530 535 540

Ser Asn Ser Asp His Val Val Phe Gly Gly Gly Thr Lys Leu Thr Val
545 550 555 560

Leu Gly Ser Thr Ser Gly Ser Gly Lys Pro Gly Ser Gly Glu Gly Ser
565 570 575

Thr Lys Gly Glu Val Gln Leu Val Glu Ser Gly Gly Gly Val Val Gln
580 585 590

Pro Gly Gly Ser Leu Arg Leu Ser Cys Ala Ala Ser Gly Phe Thr Phe
595 600 605

Asp Asp Tyr Thr Met His Trp Val Arg Gln Ala Pro Gly Lys Gly Leu
610 615 620

Glu Trp Val Ser Leu Ile Ser Trp Asp Gly Gly Ser Thr Tyr Tyr Ala
625 630 635 640

Asp Ser Val Lys Gly Arg Phe Thr Ile Ser Arg Asp Asn Ser Lys Asn
645 650 655

Ser Leu Tyr Leu Gln Met Asn Ser Leu Arg Thr Glu Asp Thr Ala Leu
660 665 670

Tyr Tyr Cys Ala Ser Ile Tyr Asp Pro Pro Pro Gly Ser Arg Ser Ala
675 680 685

Leu Asp Ala Phe Asp Ile Trp Gly Gln Gly Thr Met Val Thr Val Ser
690 695 700

Ser Ala
705

<210> SEQ ID NO 25
<211> LENGTH: 706
<212> TYPE: PRT
<213> ORGANISM: Artificial Sequence
<220> FEATURE:
<223> OTHER INFORMATION: Anti-PD-L1-OX40 Ab-V8

<400> SEQUENCE: 25

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Arg Arg Tyr
20 25 30

Ser Ile Ser Trp Val Arg Gln Ala Pro Gly Gln Gly Leu Glu Trp Met
35 40 45

Gly Gly Ile Ile Pro Val Phe Gly Ala Ala Lys Tyr Ala Gln Lys Phe
50 55 60

Gln Gly Arg Val Thr Ile Thr Ala Asp Glu Phe Thr Ser Thr Ala Tyr
65 70 75 80

Met Glu Leu Ser Ser Leu Thr Ser Glu Asp Thr Ala Val Tyr Tyr Cys
85 90 95

Ala Leu Ser Gly Asp Ser Asp Ala Phe Asp Ile Trp Gly Gln Gly Thr
100 105 110

Met Val Thr Val Ser Ser Ala Ser Thr Lys Gly Pro Ser Val Phe Pro
115 120 125

Leu Ala Pro Cys Ser Arg Ser Thr Ser Glu Ser Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser

-continued

```
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Gly Gly Gly Gly
        435                 440                 445

Ser Gly Gly Gly Gly Ser Tyr Val Leu Thr Gln Pro Pro Ser Val Ser
    450                 455                 460

Val Ala Pro Gly Lys Thr Ala Arg Ile Thr Cys Gly Gly Asn Asn Leu
465                 470                 475                 480

Glu Ser Lys Ile Val Ser Trp Tyr Gln Gln Lys Pro Gly Gln Ala Pro
                485                 490                 495

Val Leu Val Ile Phe Tyr Asp Thr Asp Arg Pro Ser Gly Ile Pro Glu
            500                 505                 510

Arg Phe Ser Gly Ser Asn Ser Gly Asn Thr Ala Thr Leu Thr Ile Ser
        515                 520                 525

Arg Val Glu Ala Gly Asp Glu Ala Asp Tyr Tyr Cys Gln Val Trp Asp
    530                 535                 540

Ser Asn Ser Asp His Val Ile Phe Gly Gly Gly Thr Lys Leu Thr Val
545                 550                 555                 560

Leu Gly Ser Thr Ser Gly Ser Gly Lys Pro Gly Ser Gly Glu Gly Ser
                565                 570                 575

Thr Lys Gly Glu Val Gln Leu Val Glu Ser Gly Gly Ile Val Val Gln
            580                 585                 590

Pro Gly Gly Ser Leu Arg Leu Ser Cys Ala Ala Ser Gly Phe Thr Phe
        595                 600                 605
```

```
Asp Asp Tyr Thr Met His Trp Val Arg Gln Ala Pro Gly Lys Gly Leu
    610                 615                 620

Glu Trp Val Ser Leu Ile Ser Trp Asp Gly Gly Ser Thr Tyr Tyr Ala
625                 630                 635                 640

Asp Ser Val Lys Gly Arg Phe Thr Ile Ser Arg Asp Asn Ser Lys Asn
                645                 650                 655

Ser Leu Tyr Leu Gln Met Asn Ser Leu Arg Thr Glu Asp Thr Ala Leu
            660                 665                 670

Tyr Tyr Cys Ala Ser Ile Tyr Asp Pro Pro Pro Gly Ser Arg Ser Ala
        675                 680                 685

Leu Asp Ala Phe Asp Ile Trp Gly Gln Gly Thr Met Val Thr Val Ser
    690                 695                 700

Ser Ala
705


<210> SEQ ID NO 26
<211> LENGTH: 706
<212> TYPE: PRT
<213> ORGANISM: Artificial Sequence
<220> FEATURE:
<223> OTHER INFORMATION: Anti-PD-L1-OX40 Ab-V9

<400> SEQUENCE: 26

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Arg Tyr
            20                  25                  30

Ser Ile Ser Trp Val Arg Gln Ala Pro Gly Gln Gly Leu Glu Trp Met
        35                  40                  45

Gly Gly Ile Ile Pro Val Phe Gly Ala Ala Lys Tyr Ala Gln Lys Phe
    50                  55                  60

Gln Gly Arg Val Thr Ile Thr Ala Asp Glu Phe Thr Ser Thr Ala Tyr
65                  70                  75                  80

Met Glu Leu Ser Ser Leu Thr Ser Glu Asp Thr Ala Val Tyr Tyr Cys
                85                  90                  95

Ala Leu Ser Gly Asp Ser Asp Ala Phe Asp Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255
```

-continued

```
Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Gly Gly Gly Gly
        435                 440                 445

Ser Gly Gly Gly Gly Ser Tyr Val Leu Thr Gln Pro Pro Ser Val Ser
    450                 455                 460

Val Ala Pro Gly Lys Thr Ala Arg Ile Thr Cys Gly Gly Asn Asn Leu
465                 470                 475                 480

Glu Ser Lys Ile Val Ser Trp Tyr Gln Gln Lys Pro Gly Gln Ala Pro
                485                 490                 495

Val Leu Val Ile Phe Tyr Asp Thr Asp Arg Pro Ser Gly Ile Pro Glu
            500                 505                 510

Arg Phe Ser Gly Ser Asn Ser Gly Asn Thr Ala Thr Leu Thr Ile Ser
        515                 520                 525

Arg Val Glu Ala Gly Asp Glu Ala Asp Tyr Tyr Cys Gln Val Trp Asp
    530                 535                 540

Ser Asn Ser Asp His Val Val Phe Gly Gly Gly Thr Lys Leu Thr Val
545                 550                 555                 560

Leu Gly Ser Thr Ser Gly Ser Gly Lys Pro Gly Ser Gly Glu Gly Ser
                565                 570                 575

Thr Lys Gly Glu Val Gln Leu Val Glu Ser Gly Gly Gly Val Val Gln
            580                 585                 590

Pro Gly Gly Ser Leu Arg Leu Ser Cys Ala Ala Ser Gly Phe Thr Phe
        595                 600                 605

Asp Asp Tyr Thr Met His Trp Val Arg Gln Ala Pro Gly Lys Gly Leu
    610                 615                 620

Glu Trp Val Ser Leu Ile Ser Trp Asp Gly Gly Ser Thr Tyr Tyr Ala
625                 630                 635                 640

Asp Ser Val Lys Gly Arg Phe Thr Ile Ser Arg Asp Asn Ser Lys Asn
                645                 650                 655

Ser Leu Tyr Leu Gln Met Asn Ser Leu Arg Thr Glu Asp Thr Ala Leu
            660                 665                 670
```

```
Tyr Tyr Cys Ala Ser Ile Tyr Asp Pro Pro Pro Gly Ser Arg Ser Ala
        675                 680                 685

Leu Asp Ala Phe Asp Ile Trp Gly Gln Gly Thr Met Val Thr Val Ser
    690                 695                 700

Ser Ala
705


<210> SEQ ID NO 27
<211> LENGTH: 706
<212> TYPE: PRT
<213> ORGANISM: Artificial Sequence
<220> FEATURE:
<223> OTHER INFORMATION: Anti-PD-L1-OX40 Ab-V10

<400> SEQUENCE: 27

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Arg Tyr
            20                  25                  30

Ser Ile Ser Trp Val Arg Gln Ala Pro Gly Gln Gly Leu Glu Trp Met
        35                  40                  45

Gly Gly Ile Ile Pro Val Phe Gly Ala Ala Lys Tyr Ala Gln Lys Phe
    50                  55                  60

Gln Gly Arg Val Thr Ile Thr Ala Asp Glu Phe Thr Ser Thr Ala Tyr
65                  70                  75                  80

Met Glu Leu Ser Ser Leu Thr Ser Glu Asp Thr Ala Val Tyr Tyr Cys
                85                  90                  95

Ala Leu Ser Gly Asp Ser Asp Ala Phe Asp Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320
```

```
Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Gly Gly Gly Gly
        435                 440                 445

Ser Gly Gly Gly Gly Ser Tyr Val Leu Thr Gln Pro Pro Ser Val Ser
    450                 455                 460

Val Ala Pro Gly Gln Thr Ala Arg Ile Thr Cys Gly Gly Asn Asn Leu
465                 470                 475                 480

Glu Ser Lys Ile Val Ser Trp Tyr Gln Gln Lys Pro Gly Gln Ala Pro
                485                 490                 495

Val Leu Val Ile Phe Tyr Asp Thr Asp Arg Pro Ser Gly Ile Pro Glu
            500                 505                 510

Arg Phe Ser Gly Ser Asn Ser Gly Asn Thr Ala Thr Leu Thr Ile Ser
        515                 520                 525

Arg Val Glu Ala Gly Asp Glu Ala Asp Tyr Tyr Cys Gln Val Trp Asp
    530                 535                 540

Ser Asn Ser Asp His Val Val Phe Gly Gly Gly Thr Lys Leu Thr Val
545                 550                 555                 560

Leu Gly Ser Thr Ser Gly Ser Gly Lys Pro Gly Ser Gly Glu Gly Ser
                565                 570                 575

Thr Lys Gly Glu Val Gln Leu Val Glu Ser Gly Gly Gly Val Val Gln
            580                 585                 590

Pro Gly Gly Ser Leu Arg Leu Ser Cys Ala Ala Ser Gly Phe Thr Phe
        595                 600                 605

Asp Asp Tyr Thr Met His Trp Val Arg Gln Ala Pro Gly Lys Gly Leu
    610                 615                 620

Glu Trp Val Ser Leu Ile Ser Trp Asp Gly Gly Ser Thr Tyr Tyr Ala
625                 630                 635                 640

Asp Ser Val Lys Gly Arg Phe Thr Ile Ser Arg Asp Asn Ser Lys Asn
                645                 650                 655

Ser Leu Tyr Leu Gln Met Asn Ser Leu Arg Thr Glu Asp Thr Ala Leu
            660                 665                 670

Tyr Tyr Cys Ala Ser Ile Tyr Asp Pro Pro Pro Gly Ser Arg Ser Ala
        675                 680                 685

Leu Asp Ala Phe Asp Ile Trp Gly Gln Gly Thr Met Val Thr Val Ser
    690                 695                 700

Ser Ala
705

<210> SEQ ID NO 28
<211> LENGTH: 706
<212> TYPE: PRT
```

<213> ORGANISM: Artificial Sequence
<220> FEATURE:
<223> OTHER INFORMATION: Anti-PD-L1-OX40 Ab-V11

<400> SEQUENCE: 28

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Arg Tyr
            20                  25                  30

Ser Ile Ser Trp Val Arg Gln Ala Pro Gly Gln Gly Leu Glu Trp Met
        35                  40                  45

Gly Gly Ile Ile Pro Val Phe Gly Ala Ala Lys Tyr Ala Gln Lys Phe
    50                  55                  60

Gln Gly Arg Val Thr Ile Thr Ala Asp Glu Phe Thr Ser Thr Ala Tyr
65                  70                  75                  80

Met Glu Leu Ser Ser Leu Thr Ser Glu Asp Thr Ala Val Tyr Tyr Cys
                85                  90                  95

Ala Leu Ser Gly Asp Ser Asp Ala Phe Asp Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
```

-continued

```
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Gly Gly Gly Gly
        435                 440                 445

Ser Gly Gly Gly Gly Ser Tyr Val Leu Thr Gln Pro Pro Ser Val Ser
    450                 455                 460

Val Thr Pro Gly Glu Thr Ala Arg Ile Ala Cys Gly Gly Asn Asn Leu
465                 470                 475                 480

Glu Ser Lys Ile Val Ser Trp Tyr Gln Gln Lys Pro Gly Gln Ala Pro
                485                 490                 495

Val Leu Val Ile Phe Tyr Asp Thr Asp Arg Pro Ser Gly Ile Ser Glu
            500                 505                 510

Arg Phe Ser Gly Ser Asn Ser Gly Asn Thr Ala Thr Leu Thr Ile Ser
        515                 520                 525

Arg Val Glu Ala Gly Asp Glu Ala Asp Tyr Tyr Cys Gln Val Trp Asp
    530                 535                 540

Ser Asn Ser Asp His Val Ile Phe Gly Gly Gly Thr Lys Leu Thr Val
545                 550                 555                 560

Leu Gly Ser Thr Ser Gly Ser Gly Lys Pro Gly Ser Gly Glu Gly Ser
                565                 570                 575

Thr Lys Gly Glu Val Gln Leu Val Glu Ser Gly Gly Val Val Gln
            580                 585                 590

Pro Gly Gly Ser Leu Arg Leu Ser Cys Ala Ala Ser Gly Phe Thr Phe
        595                 600                 605

Asp Asp Tyr Thr Met His Trp Val Arg Gln Ala Pro Gly Lys Gly Leu
    610                 615                 620

Glu Trp Val Ser Leu Ile Ser Trp Asp Gly Gly Ser Thr Tyr Tyr Ala
625                 630                 635                 640

Asp Ser Val Lys Gly Arg Phe Thr Ile Ser Arg Asp Asn Ser Lys Asn
                645                 650                 655

Ser Leu Tyr Leu Gln Met Asn Ser Leu Arg Thr Glu Asp Thr Ala Leu
            660                 665                 670

Tyr Tyr Cys Ala Ser Ile Tyr Asp Pro Pro Pro Gly Ser Arg Ser Ala
        675                 680                 685

Leu Asp Ala Phe Asp Ile Trp Gly Gln Gly Thr Met Val Thr Val Ser
    690                 695                 700

Ser Ala
705


<210> SEQ ID NO 29
<211> LENGTH: 706
<212> TYPE: PRT
<213> ORGANISM: Artificial Sequence
<220> FEATURE:
<223> OTHER INFORMATION: Anti-PD-L1-OX40 Ab-V12

<400> SEQUENCE: 29

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Arg Tyr
            20                  25                  30

Ser Ile Ser Trp Val Arg Gln Ala Pro Gly Gln Gly Leu Glu Trp Met
```

-continued

```
        35                  40                  45

Gly Gly Ile Ile Pro Val Phe Gly Ala Ala Lys Tyr Ala Gln Lys Phe
    50                  55                  60

Gln Gly Arg Val Thr Ile Thr Ala Asp Glu Phe Thr Ser Thr Ala Tyr
65                  70                  75                  80

Met Glu Leu Ser Ser Leu Thr Ser Glu Asp Thr Ala Val Tyr Tyr Cys
                85                  90                  95

Ala Leu Ser Gly Asp Ser Asp Ala Phe Asp Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Gly Gly Gly Gly
        435                 440                 445

Ser Gly Gly Gly Gly Ser Tyr Val Leu Thr Gln Pro Pro Ser Val Ser
    450                 455                 460
```

Val Thr Pro Gly Gln Thr Ala Arg Ile Ala Cys Gly Gly Asn Asn Leu
465 470 475 480

Glu Ser Lys Ile Val Ser Trp Tyr Gln Gln Lys Pro Gly Gln Ala Pro
485 490 495

Val Leu Val Ile Phe Tyr Asp Thr Asp Arg Pro Ser Gly Ile Ser Glu
500 505 510

Arg Phe Ser Gly Ser Asn Ser Gly Asn Thr Ala Thr Leu Thr Ile Ser
515 520 525

Arg Val Glu Ala Gly Asp Glu Ala Asp Tyr Tyr Cys Gln Val Trp Asp
530 535 540

Ser Asn Ser Asp His Val Ile Phe Gly Gly Gly Thr Lys Leu Thr Val
545 550 555 560

Leu Gly Ser Thr Ser Gly Ser Gly Lys Pro Gly Ser Gly Glu Gly Ser
565 570 575

Thr Lys Gly Glu Val Gln Leu Val Glu Ser Gly Gly Val Val Val Gln
580 585 590

Pro Gly Gly Ser Leu Arg Leu Ser Cys Ala Ala Ser Gly Phe Thr Phe
595 600 605

Asp Asp Tyr Thr Met His Trp Val Arg Gln Ala Pro Gly Lys Gly Leu
610 615 620

Glu Trp Val Ser Leu Ile Ser Trp Asp Gly Gly Ser Thr Tyr Tyr Ala
625 630 635 640

Asp Ser Val Lys Gly Arg Phe Thr Ile Ser Arg Asp Asn Ser Lys Asn
645 650 655

Ser Leu Tyr Leu Gln Met Asn Ser Leu Arg Thr Glu Asp Thr Ala Leu
660 665 670

Tyr Tyr Cys Ala Ser Ile Tyr Asp Pro Pro Pro Gly Ser Arg Ser Ala
675 680 685

Leu Asp Ala Phe Asp Ile Trp Gly Gln Gly Thr Met Val Thr Val Ser
690 695 700

Ser Ala
705

<210> SEQ ID NO 30
<211> LENGTH: 176
<212> TYPE: PRT
<213> ORGANISM: Artificial Sequence
<220> FEATURE:
<223> OTHER INFORMATION: Anti-PD-L1-OX40 Ab-V4

<400> SEQUENCE: 30

Leu Ser Leu Gly Gly Gly Gly Gly Ser Gly Gly Gly Gly Ser Tyr Val
1 5 10 15

Leu Thr Gln Pro Pro Ser Val Ser Val Thr Pro Gly Lys Thr Ala Arg
20 25 30

Ile Ala Cys Gly Gly Asn Asn Leu Glu Ser Lys Ile Val Ser Trp Tyr
35 40 45

Gln Gln Lys Pro Gly Gln Ala Pro Val Leu Val Ile Phe Tyr Asp Thr
50 55 60

Asp Arg Pro Ser Gly Ile Ser Glu Arg Phe Ser Gly Ser Asn Ser Gly
65 70 75 80

Asn Thr Ala Thr Leu Thr Ile Ser Arg Val Glu Ala Gly Asp Glu Ala
85 90 95

Asp Tyr Tyr Cys Gln Val Trp Asp Ser Asn Ser Asp His Val Ile Phe
100 105 110

```
Gly Gly Gly Thr Lys Leu Thr Val Leu Gly Ser Thr Ser Gly Ser Gly
        115                 120                 125

Lys Pro Gly Ser Gly Glu Gly Ser Thr Lys Gly Glu Val Gln Leu Val
    130                 135                 140

Glu Ser Gly Gly Val Val Val Gln Pro Gly Gly Ser Leu Arg Leu Ser
145                 150                 155                 160

Cys Ala Ala Ser Gly Phe Thr Phe Asp Asp Tyr Thr Met His Trp Val
                165                 170                 175


<210> SEQ ID NO 31
<211> LENGTH: 176
<212> TYPE: PRT
<213> ORGANISM: Artificial Sequence
<220> FEATURE:
<223> OTHER INFORMATION: Anti-PD-L1-OX40 Ab-V5

<400> SEQUENCE: 31

Leu Ser Leu Gly Gly Gly Gly Gly Ser Gly Gly Gly Gly Ser Tyr Glu
1               5                   10                  15

Leu Thr Gln Pro Pro Ser Val Ser Val Thr Pro Gly Gln Thr Ala Arg
            20                  25                  30

Ile Ala Cys Gly Gly Asn Asn Leu Glu Ser Lys Ile Val Ser Trp Tyr
        35                  40                  45

Gln Gln Lys Pro Gly Gln Ala Pro Val Leu Val Ile Phe Tyr Asp Thr
    50                  55                  60

Asp Arg Pro Ser Gly Ile Ser Glu Arg Phe Ser Gly Ser Asn Ser Gly
65                  70                  75                  80

Asn Thr Ala Thr Leu Thr Ile Ser Arg Val Glu Ala Gly Asp Glu Ala
                85                  90                  95

Asp Tyr Tyr Cys Gln Val Trp Asp Ser Asn Ser Asp His Val Ile Phe
            100                 105                 110

Gly Gly Gly Thr Lys Leu Thr Val Leu Gly Ser Thr Ser Gly Ser Gly
        115                 120                 125

Lys Pro Gly Ser Gly Glu Gly Ser Thr Lys Gly Glu Val Gln Leu Val
    130                 135                 140

Glu Ser Gly Gly Val Val Val Gln Pro Gly Gly Ser Leu Arg Leu Ser
145                 150                 155                 160

Cys Ala Ala Ser Gly Phe Thr Phe Asp Asp Tyr Thr Met His Trp Val
                165                 170                 175


<210> SEQ ID NO 32
<211> LENGTH: 176
<212> TYPE: PRT
<213> ORGANISM: Artificial Sequence
<220> FEATURE:
<223> OTHER INFORMATION: Anti-PD-L1-OX40 Ab-V6

<400> SEQUENCE: 32

Leu Ser Leu Gly Gly Gly Gly Gly Ser Gly Gly Gly Gly Ser Tyr Val
1               5                   10                  15

Leu Thr Gln Pro Pro Ser Val Ser Val Thr Pro Gly Glu Thr Ala Arg
            20                  25                  30

Ile Ala Cys Gly Gly Asn Asn Leu Glu Ser Lys Ile Val Ser Trp Tyr
        35                  40                  45

Gln Gln Lys Pro Gly Gln Ala Pro Val Leu Val Ile Phe Tyr Asp Thr
    50                  55                  60

Asp Arg Pro Ser Gly Ile Ser Glu Arg Phe Ser Gly Ser Asn Ser Gly
```

```
65                  70                  75                  80

Asn Thr Ala Thr Leu Thr Ile Ser Arg Val Glu Ala Gly Asp Glu Ala
                85                  90                  95

Asp Tyr Tyr Cys Gln Val Trp Asp Ser Asn Ser Asp His Val Val Phe
            100                 105                 110

Gly Gly Gly Thr Lys Leu Thr Val Leu Gly Ser Thr Ser Gly Ser Gly
        115                 120                 125

Lys Pro Gly Ser Gly Glu Gly Ser Thr Lys Gly Glu Val Gln Leu Val
    130                 135                 140

Glu Ser Gly Gly Gly Val Val Gln Pro Gly Gly Ser Leu Arg Leu Ser
145                 150                 155                 160

Cys Ala Ala Ser Gly Phe Thr Phe Asp Asp Tyr Thr Met His Trp Val
                165                 170                 175


<210> SEQ ID NO 33
<211> LENGTH: 176
<212> TYPE: PRT
<213> ORGANISM: Artificial Sequence
<220> FEATURE:
<223> OTHER INFORMATION: Anti-PD-L1-OX40 Ab-V7

<400> SEQUENCE: 33

Leu Ser Leu Gly Gly Gly Gly Gly Ser Gly Gly Gly Gly Ser Tyr Val
1               5                   10                  15

Leu Thr Gln Pro Pro Ser Val Ser Val Thr Pro Gly Gln Thr Ala Arg
            20                  25                  30

Ile Ala Cys Gly Gly Asn Asn Leu Glu Ser Lys Ile Val Ser Trp Tyr
        35                  40                  45

Gln Gln Lys Pro Gly Gln Ala Pro Val Leu Val Ile Phe Tyr Asp Thr
    50                  55                  60

Asp Arg Pro Ser Gly Ile Ser Glu Arg Phe Ser Gly Ser Asn Ser Gly
65                  70                  75                  80

Asn Thr Ala Thr Leu Thr Ile Ser Arg Val Glu Ala Gly Asp Glu Ala
                85                  90                  95

Asp Tyr Tyr Cys Gln Val Trp Asp Ser Asn Ser Asp His Val Val Phe
            100                 105                 110

Gly Gly Gly Thr Lys Leu Thr Val Leu Gly Ser Thr Ser Gly Ser Gly
        115                 120                 125

Lys Pro Gly Ser Gly Glu Gly Ser Thr Lys Gly Glu Val Gln Leu Val
    130                 135                 140

Glu Ser Gly Gly Gly Val Val Gln Pro Gly Gly Ser Leu Arg Leu Ser
145                 150                 155                 160

Cys Ala Ala Ser Gly Phe Thr Phe Asp Asp Tyr Thr Met His Trp Val
                165                 170                 175


<210> SEQ ID NO 34
<211> LENGTH: 176
<212> TYPE: PRT
<213> ORGANISM: Artificial Sequence
<220> FEATURE:
<223> OTHER INFORMATION: Anti-PD-L1-OX40 Ab-V8

<400> SEQUENCE: 34

Leu Ser Leu Gly Gly Gly Gly Gly Ser Gly Gly Gly Gly Ser Tyr Val
1               5                   10                  15

Leu Thr Gln Pro Pro Ser Val Ser Val Ala Pro Gly Lys Thr Ala Arg
            20                  25                  30
```

-continued

```
Ile Thr Cys Gly Gly Asn Asn Leu Glu Ser Lys Ile Val Ser Trp Tyr
        35                  40                  45

Gln Gln Lys Pro Gly Gln Ala Pro Val Leu Val Ile Phe Tyr Asp Thr
    50                  55                  60

Asp Arg Pro Ser Gly Ile Pro Glu Arg Phe Ser Gly Ser Asn Ser Gly
65                  70                  75                  80

Asn Thr Ala Thr Leu Thr Ile Ser Arg Val Glu Ala Gly Asp Glu Ala
                85                  90                  95

Asp Tyr Tyr Cys Gln Val Trp Asp Ser Asn Ser Asp His Val Ile Phe
            100                 105                 110

Gly Gly Gly Thr Lys Leu Thr Val Leu Gly Ser Thr Ser Gly Ser Gly
        115                 120                 125

Lys Pro Gly Ser Gly Glu Gly Ser Thr Lys Gly Glu Val Gln Leu Val
    130                 135                 140

Glu Ser Gly Gly Ile Val Val Gln Pro Gly Gly Ser Leu Arg Leu Ser
145                 150                 155                 160

Cys Ala Ala Ser Gly Phe Thr Phe Asp Asp Tyr Thr Met His Trp Val
                165                 170                 175


<210> SEQ ID NO 35
<211> LENGTH: 176
<212> TYPE: PRT
<213> ORGANISM: Artificial Sequence
<220> FEATURE:
<223> OTHER INFORMATION: Anti-PD-L1-OX40 Ab-V9

<400> SEQUENCE: 35

Leu Ser Leu Gly Gly Gly Gly Gly Ser Gly Gly Gly Gly Ser Tyr Val
1               5                   10                  15

Leu Thr Gln Pro Pro Ser Val Ser Val Ala Pro Gly Lys Thr Ala Arg
            20                  25                  30

Ile Thr Cys Gly Gly Asn Asn Leu Glu Ser Lys Ile Val Ser Trp Tyr
        35                  40                  45

Gln Gln Lys Pro Gly Gln Ala Pro Val Leu Val Ile Phe Tyr Asp Thr
    50                  55                  60

Asp Arg Pro Ser Gly Ile Pro Glu Arg Phe Ser Gly Ser Asn Ser Gly
65                  70                  75                  80

Asn Thr Ala Thr Leu Thr Ile Ser Arg Val Glu Ala Gly Asp Glu Ala
                85                  90                  95

Asp Tyr Tyr Cys Gln Val Trp Asp Ser Asn Ser Asp His Val Val Phe
            100                 105                 110

Gly Gly Gly Thr Lys Leu Thr Val Leu Gly Ser Thr Ser Gly Ser Gly
        115                 120                 125

Lys Pro Gly Ser Gly Glu Gly Ser Thr Lys Gly Glu Val Gln Leu Val
    130                 135                 140

Glu Ser Gly Gly Gly Val Val Gln Pro Gly Gly Ser Leu Arg Leu Ser
145                 150                 155                 160

Cys Ala Ala Ser Gly Phe Thr Phe Asp Asp Tyr Thr Met His Trp Val
                165                 170                 175


<210> SEQ ID NO 36
<211> LENGTH: 176
<212> TYPE: PRT
<213> ORGANISM: Artificial Sequence
<220> FEATURE:
<223> OTHER INFORMATION: Anti-PD-L1-OX40 Ab-V10

<400> SEQUENCE: 36
```

```
Leu Ser Leu Gly Gly Gly Gly Gly Ser Gly Gly Gly Gly Ser Tyr Val
1               5                   10                  15

Leu Thr Gln Pro Pro Ser Val Ser Val Ala Pro Gly Gln Thr Ala Arg
            20                  25                  30

Ile Thr Cys Gly Gly Asn Asn Leu Glu Ser Lys Ile Val Ser Trp Tyr
        35                  40                  45

Gln Gln Lys Pro Gly Gln Ala Pro Val Leu Val Ile Phe Tyr Asp Thr
    50                  55                  60

Asp Arg Pro Ser Gly Ile Pro Glu Arg Phe Ser Gly Ser Asn Ser Gly
65                  70                  75                  80

Asn Thr Ala Thr Leu Thr Ile Ser Arg Val Glu Ala Gly Asp Glu Ala
                85                  90                  95

Asp Tyr Tyr Cys Gln Val Trp Asp Ser Asn Ser Asp His Val Val Phe
            100                 105                 110

Gly Gly Gly Thr Lys Leu Thr Val Leu Gly Ser Thr Ser Gly Ser Gly
        115                 120                 125

Lys Pro Gly Ser Gly Glu Gly Ser Thr Lys Gly Glu Val Gln Leu Val
    130                 135                 140

Glu Ser Gly Gly Gly Val Val Gln Pro Gly Gly Ser Leu Arg Leu Ser
145                 150                 155                 160

Cys Ala Ala Ser Gly Phe Thr Phe Asp Asp Tyr Thr Met His Trp Val
                165                 170                 175


<210> SEQ ID NO 37
<211> LENGTH: 176
<212> TYPE: PRT
<213> ORGANISM: Artificial Sequence
<220> FEATURE:
<223> OTHER INFORMATION: Anti-PD-L1-OX40 Ab-V11

<400> SEQUENCE: 37

Leu Ser Leu Gly Gly Gly Gly Gly Ser Gly Gly Gly Gly Ser Tyr Val
1               5                   10                  15

Leu Thr Gln Pro Pro Ser Val Ser Val Thr Pro Gly Glu Thr Ala Arg
            20                  25                  30

Ile Ala Cys Gly Gly Asn Asn Leu Glu Ser Lys Ile Val Ser Trp Tyr
        35                  40                  45

Gln Gln Lys Pro Gly Gln Ala Pro Val Leu Val Ile Phe Tyr Asp Thr
    50                  55                  60

Asp Arg Pro Ser Gly Ile Ser Glu Arg Phe Ser Gly Ser Asn Ser Gly
65                  70                  75                  80

Asn Thr Ala Thr Leu Thr Ile Ser Arg Val Glu Ala Gly Asp Glu Ala
                85                  90                  95

Asp Tyr Tyr Cys Gln Val Trp Asp Ser Asn Ser Asp His Val Ile Phe
            100                 105                 110

Gly Gly Gly Thr Lys Leu Thr Val Leu Gly Ser Thr Ser Gly Ser Gly
        115                 120                 125

Lys Pro Gly Ser Gly Glu Gly Ser Thr Lys Gly Glu Val Gln Leu Val
    130                 135                 140

Glu Ser Gly Gly Val Val Val Gln Pro Gly Gly Ser Leu Arg Leu Ser
145                 150                 155                 160

Cys Ala Ala Ser Gly Phe Thr Phe Asp Asp Tyr Thr Met His Trp Val
                165                 170                 175


<210> SEQ ID NO 38
```

<211> LENGTH: 176
<212> TYPE: PRT
<213> ORGANISM: Artificial Sequence
<220> FEATURE:
<223> OTHER INFORMATION: Anti-PD-L1-OX40 Ab-V12

<400> SEQUENCE: 38

Leu Ser Leu Gly Gly Gly Gly Gly Ser Gly Gly Gly Gly Ser Tyr Val
1 5 10 15

Leu Thr Gln Pro Pro Ser Val Ser Val Thr Pro Gly Gln Thr Ala Arg
20 25 30

Ile Ala Cys Gly Gly Asn Asn Leu Glu Ser Lys Ile Val Ser Trp Tyr
35 40 45

Gln Gln Lys Pro Gly Gln Ala Pro Val Leu Val Ile Phe Tyr Asp Thr
50 55 60

Asp Arg Pro Ser Gly Ile Ser Glu Arg Phe Ser Gly Ser Asn Ser Gly
65 70 75 80

Asn Thr Ala Thr Leu Thr Ile Ser Arg Val Glu Ala Gly Asp Glu Ala
85 90 95

Asp Tyr Tyr Cys Gln Val Trp Asp Ser Asn Ser Asp His Val Ile Phe
100 105 110

Gly Gly Gly Thr Lys Leu Thr Val Leu Gly Ser Thr Ser Gly Ser Gly
115 120 125

Lys Pro Gly Ser Gly Glu Gly Ser Thr Lys Gly Glu Val Gln Leu Val
130 135 140

Glu Ser Gly Gly Val Val Val Gln Pro Gly Gly Ser Leu Arg Leu Ser
145 150 155 160

Cys Ala Ala Ser Gly Phe Thr Phe Asp Asp Tyr Thr Met His Trp Val
165 170 175

<210> SEQ ID NO 39
<211> LENGTH: 15
<212> TYPE: PRT
<213> ORGANISM: Artificial Sequence
<220> FEATURE:
<223> OTHER INFORMATION: linker

<400> SEQUENCE: 39

Gly Gly Gly Gly Ser Gly Gly Gly Gly Ser Gly Gly Gly Gly Ser
1 5 10 15

<210> SEQ ID NO 40
<211> LENGTH: 19
<212> TYPE: PRT
<213> ORGANISM: Artificial Sequence
<220> FEATURE:
<223> OTHER INFORMATION: linker

<400> SEQUENCE: 40

Ser Ser Gly Gly Gly Gly Ser Gly Gly Gly Gly Gly Gly Ser Ser Arg
1 5 10 15

Ser Ser Leu

<210> SEQ ID NO 41
<211> LENGTH: 20
<212> TYPE: PRT
<213> ORGANISM: Artificial Sequence
<220> FEATURE:
<223> OTHER INFORMATION: linker

<400> SEQUENCE: 41

-continued

```
Gly Gly Lys Gly Ser Gly Gly Lys Gly Thr Gly Gly Lys Gly Ser Gly
1               5                   10                  15

Gly Lys Gly Ser
            20


<210> SEQ ID NO 42
<211> LENGTH: 13
<212> TYPE: PRT
<213> ORGANISM: Artificial Sequence
<220> FEATURE:
<223> OTHER INFORMATION: linker

<400> SEQUENCE: 42

Gly Ser Ala Ser Ala Pro Thr Leu Phe Pro Leu Val Ser
1               5                   10


<210> SEQ ID NO 43
<211> LENGTH: 18
<212> TYPE: PRT
<213> ORGANISM: Artificial Sequence
<220> FEATURE:
<223> OTHER INFORMATION: linker

<400> SEQUENCE: 43

Gly Ser Thr Ser Gly Ser Gly Lys Pro Gly Ser Gly Glu Gly Ser Thr
1               5                   10                  15

Lys Gly
```